(12) United States Patent
Juliano et al.

(10) Patent No.: US 11,040,056 B2
(45) Date of Patent: Jun. 22, 2021

(54) BENZIMIDAZOLES THAT ENHANCE THE ACTIVITY OF OLIGONUCLEOTIDES

(71) Applicant: The University of North Carolina at Chapel Hill, Chapel Hill, NC (US)

(72) Inventors: Rudolph L. Juliano, Chapel Hill, NC (US); Silvia M. Kreda, Mebane, NC (US); Ling Wang, Chapel Hill, NC (US); Xin Ming, Chapel Hill, NC (US); Lindsey Ingerman James, Chapel Hill, NC (US); Ranathunga Arachchillage Yamuna Kumari Ariyarathna, Carrboro, NC (US)

(73) Assignee: THE UNIVERSITY OF NORTH CAROLINA AT CHAPEL HILL, Chapel Hill, NC (US)

( * ) Notice: Subject to any disclaimer, the term of this patent is extended or adjusted under 35 U.S.C. 154(b) by 0 days.

(21) Appl. No.: 16/409,173

(22) Filed: May 10, 2019

(65) Prior Publication Data

US 2019/0343868 A1 Nov. 14, 2019

Related U.S. Application Data

(60) Provisional application No. 62/670,431, filed on May 11, 2018.

(51) Int. Cl.
| | | |
|---|---|---|
| *A61K 31/7125* | (2006.01) | |
| *C12N 15/113* | (2010.01) | |
| *A61K 31/4184* | (2006.01) | |
| *A61K 31/4985* | (2006.01) | |
| *C07D 235/30* | (2006.01) | |
| *A61P 11/00* | (2006.01) | |

(52) U.S. Cl.
CPC ...... *A61K 31/7125* (2013.01); *A61K 31/4184* (2013.01); *A61K 31/4985* (2013.01); *A61P 11/00* (2018.01); *C07D 235/30* (2013.01); *C12N 15/113* (2013.01); *C12N 2310/314* (2013.01); *C12N 2310/3233* (2013.01); *C12N 2320/31* (2013.01); *C12N 2320/33* (2013.01)

(58) Field of Classification Search
CPC .............. C12N 15/113; C12N 2320/33; C12N 2310/11; C12N 2320/50; A61K 31/4184; A61K 31/4985
See application file for complete search history.

(56) References Cited

U.S. PATENT DOCUMENTS

| | | | | |
|---|---|---|---|---|
| 10,266,823 B2* | 4/2019 | Juliano | ................ | C12N 15/113 |
| 2017/0130222 A1 | 5/2017 | Juliano et al. | | |

FOREIGN PATENT DOCUMENTS

WO 2016003816 A1 1/2016

OTHER PUBLICATIONS

Sobczak et al (J. Gene Med 11:813-823, 2009) (Year: 2009).*
Sazani et al (Nature Biotechnology 20: 1228-1233, 2002) (Year: 2002).*
Althaus, Mike. 2013. "ENaC Inhibitors and Airway Re-hydration in Cystic Fibrosis: State of the Art." Current Molecular Pharmacology. vol. 6, 3-12.
Bonser, Luke R., and Erle, David J. 2017. "Airway Mucus and Asthma: The Role of MUC5AC and MUC5B." Journal of Clinical Medicine. vol. 6, 112, 1-17 (published Nov. 29, 2017).
Chung, Felicity et al. 2018. "Novel Oligonucleotide and small molecule-mediated correction of CF splicing mutations." Research Frontiers abstracts (Jun. 18-21, 2018).
Gao, Wei et al. 2015. "Bronchial epithelial cells: The key effector cells in the pathogenesis of chronic obstructive pulmonary disease." Respirology. vol. 20, 722-729.
Kole, Ryszard et al. 2012. "RNA therapeutics: beyond RNA interference and antisense oligonucleotides." Nature Reviews. vol. 11, 2, 125-140.
Martin, S. Lorraine et al. 2018. "Ion channels as targets to treat cystic fibrosis lung disease." vol. 17, S22-S27 (available online Nov. 6, 2017).
Sonneville, Florence et al. 2017. "MicroRNA-9 downregulates the ANO1 chloride channel and contributes to cystic fibrosis lung pathology." Nature Communications. vol. 8, 710 (available online Sep. 27, 2017).
Wang, Ling et al. 2017. "A Novel Family of Small Molecules that Enhance the Intracellular Delivery and Pharmacological Effectiveness of Antisense and Splice Switching Oligonucleotides." ACS Chmical Biology. vol. 12, 1999-2007 (published Jul. 13, 2017).
Yang, B. et al. 2015. "High-throughput screening identifies small molecules that enhance the pharmacological effects of oligonucleotides." Nucleic Acids Research. vol. 43, No. 4, 1987-1996.
Bennett, C., et al. "RNA Targeting Therapeutics: Molecular Mechanisms of Antisense Oligonucleotides as a Therapeutic Platform." Annu. Rev. Pharmacol. Toxicol., Feb. 2010, 259-93, 50, Annual Reviews, Palo Alto, California.
Bennett, C., et al. "Pharmacology of Antisense Drugs." Annu. Rev. Pharmacol. Toxicol., Jan. 2017, 81-105, 57, Annual Reviews, Palo Alto, California.
Cai, H., et al. "Coats, Tethers, Rabs, and SNAREs Work Together to Mediate the Intracellular Destination of a Transport Vesicle." Developmental Cell, May 2007, 671-682, 12 (5), Elsevier Inc., Amsterdam.
Doherty, G., et al. "Mechanisms of Endocytosis." Annu. Rev. Biochem.,Jul. 2009, 31.1-31.46, 78, Annual Reviews, Palo Alto, California.
Dunn, K., et. al. "A practical guide to evaluating colocalization in biological microscopy." Am J Physiol Cell Physiol, Apr. 2011, C723-C742, 300 (4), American Physiological Society (APS) Publications, Rockville, Maryland.

(Continued)

*Primary Examiner* — Richard A Schnizer
(74) *Attorney, Agent, or Firm* — Olive Law Group PLLC; Nathan P. Letts

(57) ABSTRACT

This disclosure is directed to methods, compounds and compositions for delivering nucleic acids to a cell of interest. In particular, it provides salts that are particularly effective in delivering nucleic acids to cells in the lung for disorders such as cystic fibrosis (CF).

23 Claims, 17 Drawing Sheets

Figure 1A:
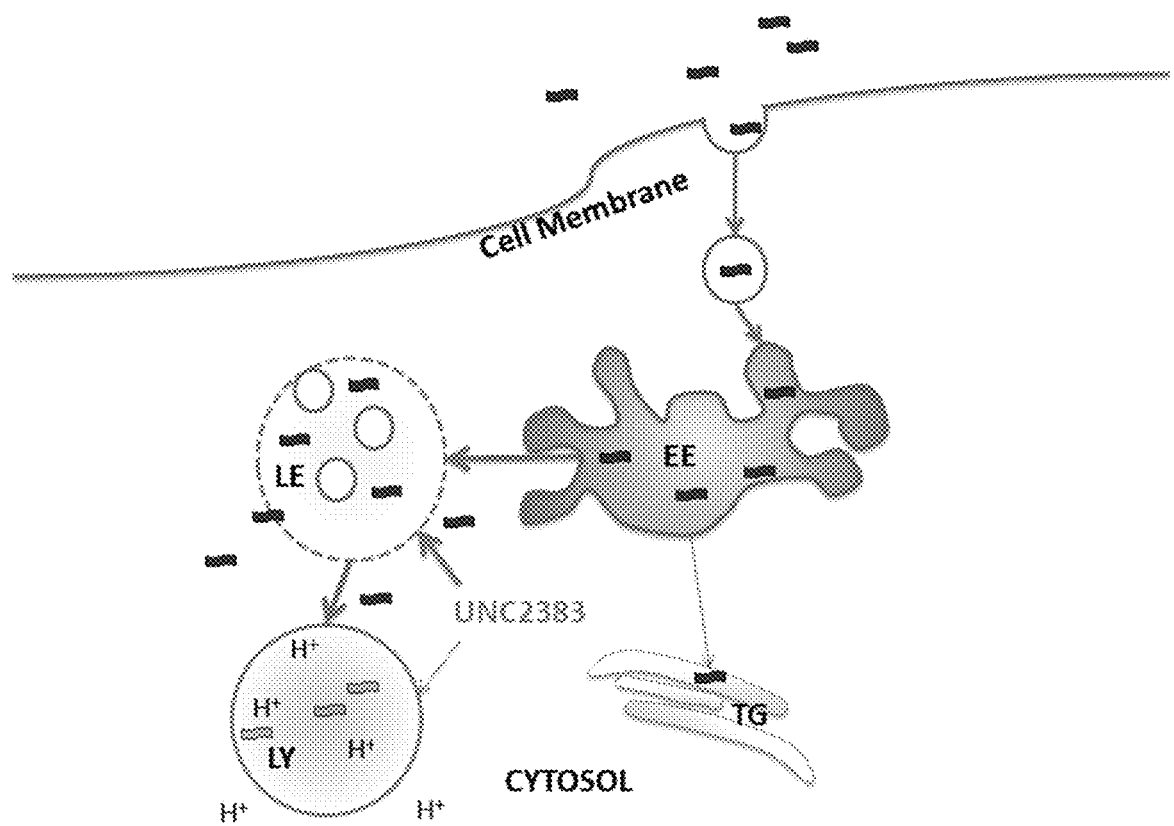

Specification includes a Sequence Listing.

(56) References Cited

OTHER PUBLICATIONS

Gilleron, J., et al. "Identification of siRNA delivery enhancers by a chemical library screen." Nucleic Acids Res., Sep. 2015, 7984-8001, 43 (16), Oxford University Press, United Kingdom.
Juliano, R., et al. "The Chemistry and Biology of Oligonucleotide Conjugates." Acc. Chem. Res., Feb. 2012, 1067-1076, 45 (7), American Chemical Society (ACS) Publications, Washington, D.C.
Juliano, R., et al. "Mechanisms and strategies for effective delivery of antisense and siRNA oligonucleotides." Nucleic Acids Res., Jul. 2008, 4158-4171, 36 (12), Oxford University Press, United Kingdom.
Juliano, R., et al. "The delivery of therapeutic oligonucleotides." Nucleic Acids Res., Aug. 2016, 6518-6548, 44 (14), Oxford University Press, United Kingdom.
Juliano, R., et al. "Cellular Uptake and Intracellular Trafficking of Antisense and siRNA Oligonucleotides." Bioconjug Chem., Feb. 2012, 147-157, 23 (2), ACS Publications, Washington, D.C.
Kang, H., et al. "Inhibition of MDR1 gene expression by chimeric HNA antisense oligonucleotides." Nucleic Acids Res., Aug. 2004, 4411-4419, 32 (14), Oxford University Press, United Kingdom.
Keri, R., et al. "Comprehensive Review in Current Developments of Benzimidazole-Based Medicinal Chemistry." Chem Biol Drug Des, 2015, 19-65, 86, John Wiley & Sons A/S, John Wiley & Sons Ltd, United States.
Kreda, S., et al. "Imaging CFTR Protein Localization in Cultured Cells and Tissues." Methods Mol Biol., Apr. 2011, 15-33, 742, Springer Science+Business Media, LLC, New York City.
Kreda, S., et al. "G-protein-coupled receptors as targets for gene transfer vectors using natural small-molecule ligands." Nature Biotechnology, Jun. 2000, 635-640, 18, Nature America Inc., New York City.
Kummel, D., et al. "Principles of membrane tethering and fusion in endosome and lysosome biogenesis." Current Opinion in Cell Biology, Aug. 2014, 61-66, 29, Elsevier Inc., Amsterdam.
Manoharan, Muthiah. "RNA interference and chemically modified small interfering RNAs." Current Opinion in Cell Biology, Dec. 2004, 570-579, 8 (6), Elsevier Inc., Amsterdam.
Mellman, I., et al. "A Nobel Prize for Membrane Traffic: Vesicles Find Their Journey's End." J Cell Biol, Nov. 2013, 559-561, 203 (4), The Rockefeller University Press, New York City.
Ming, X., et al. "Transport of Dicationic Drugs Pentamidine and Furamidine by Human Organic Cation Transporters." Drug Metabolism and Disposition, Feb. 2009, 424-430, 37 (2), The American Society for Pharmacology and Experimental Therapeutics (ASPET), Rockville, Maryland.
Ming, X., et al. "The small molecule Retro-1 enhances the pharmacological actions of antisense and splice switching oligonucleotides." Nucleic Acids Res., Apr. 2013, 3673-3687, 41 (6), Oxford University Press, United Kingdom.
Osborn, M. et al. "Guanabenz (WytensinTM) selectively enhances uptake and efficacy of hydrophobically modified siRNAs." Nucleic Acids Res., Oct. 2015, 8664-8672, 43 (18), Oxford University Press, United Kingdom.
Pfeffer, Suzanne R. "Rab GTPase regulation of membrane identity." Current Opinion in Cell Biology, Aug. 2013, 414-419, 35 (4), Elsevier Inc., Amsterdam.
Quon, B., et al. "New and emerging targeted therapies for cystic fibrosis." BMJ, Mar. 2016, 352 (14 pages), BMJ Publishing Group Ltd, London.
Roberts, J., et al. "Efficient and Persistent Splice Switching by Systemically Delivered LNA Oligonucleotides in Mice." Molecular Therapy, Oct. 2006, 471-475, 14 (4), The American Society of Gene Therapy (ASGCT), Milwaukee, Wisconsin.
Sazani, P., et al. "Systemically delivered antisense oligomers upregulate gene expression in mouse tissues." Nature Biotechnology, Nov. 2002, 1228-1233, 20, Nature America Inc., New York City.
Tse, Man T. "Antisense approval provides boost to the field." Nature Reviews, Mar. 2013, 179, 12, Macmillan Publishers Limited, New York City.
Varkouhi, Amir K. "Nanoparticulate Systems for Nucleic Acid Delivery." Thesis published in 2011, 188 pages. Meditrans, J.E. Jurriaanse Stichting, Rotterdam, The Netherlands, Utrecht Institute for Pharmaceutical Sciences.
Von Kleist, L., et al. "At the Crossroads of Chemistry and Cell Biology: Inhibiting Membrane Traffic by Small Molecules." Traffic, Sep. 2011, 495-504, 13, John Wiley & Sons A/S, John Wiley & Sons Ltd, United States.
Wang, T., et al. "Lipid Mixing and Content Release in Single-Vesicle, SNARE-Driven Fusion Assay with 1-5 ms Resolution." Biophysical Journal, May 2009, 4122-4131, 96 (10), Cell Press, Cambridge, Massachusetts.
Watts, J., et al. "Gene silencing by siRNAs and antisense oligonucleotides in the laboratory and the clinic." J Pathol., Jan. 2012, 365-379, 226 (2), John Wiley & Sons Ltd, United States.
Wu, S., et al. "RNAi Therapies: Drugging the Undruggable." Science Translational Medicine, Jun. 2014, 7 pages, 6 (240), American Association for the Advancement of Science (AAAS), Washington, D.C.
Xu, S., et al. "Targeting receptor-mediated endocytotic pathways with nanoparticles: rationale and advances." Adv Drug Deliv Rev., Jan. 2013, 121-138, 65 (1), Elsevier Inc., Amsterdam.

* cited by examiner

Oligonucleotides (ribbons) enter the cell by endocytosis and then traffic to early endosomes (EE), late endosomes (LE), lysosomes (LY) and trans-Golgi (TG).

Fig. 2. Structure of Analogs
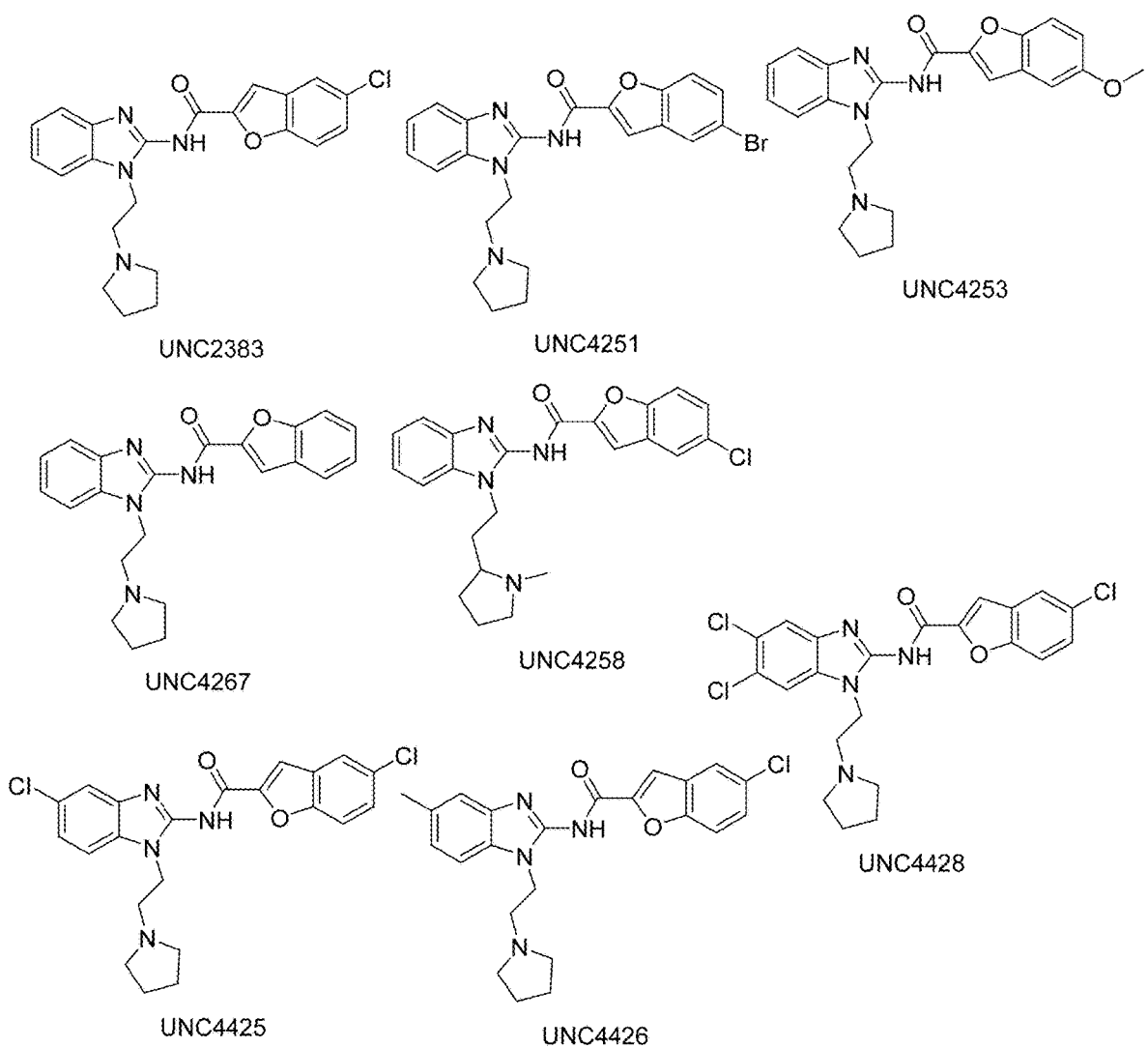

Fig. 3. Effect and Cytotoxicity of Analogs
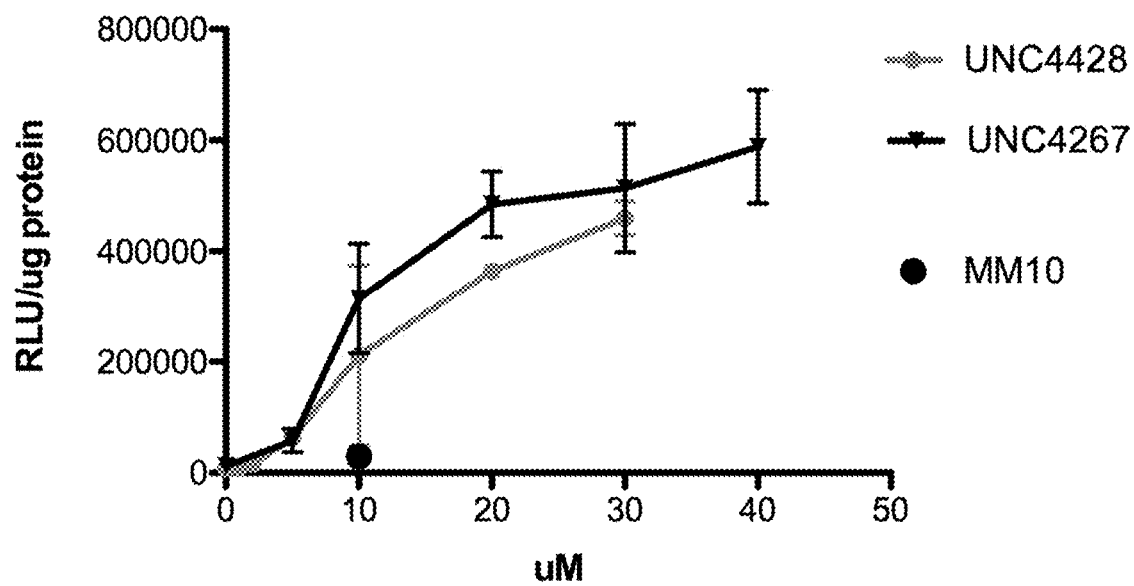
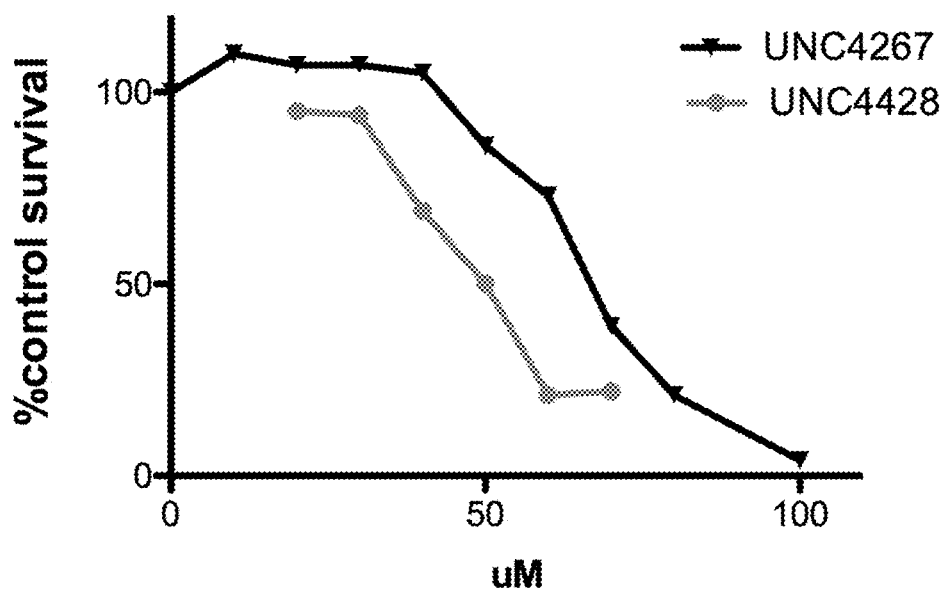

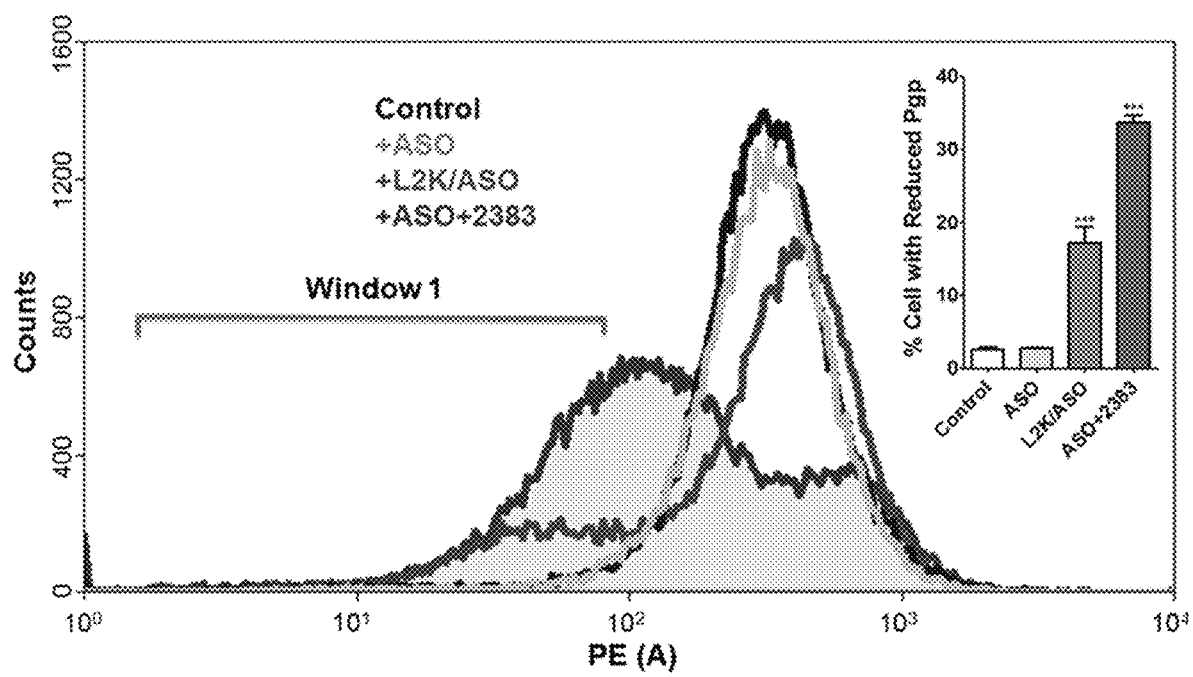
Fig. 4. Effects with ASOs. Reduction of Pgp expression.

Fig. 5A. Effect on Endomembrane Permeability.
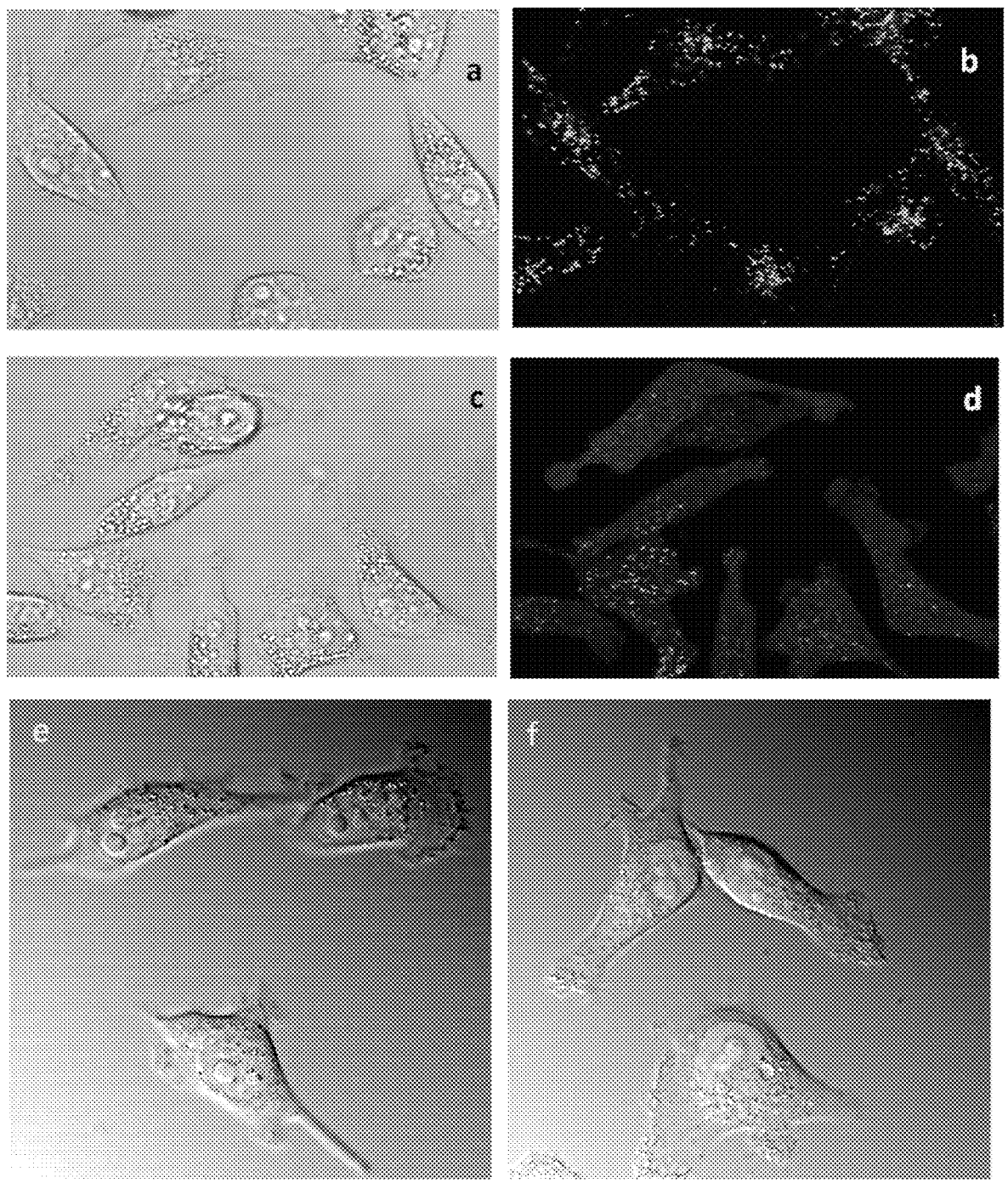

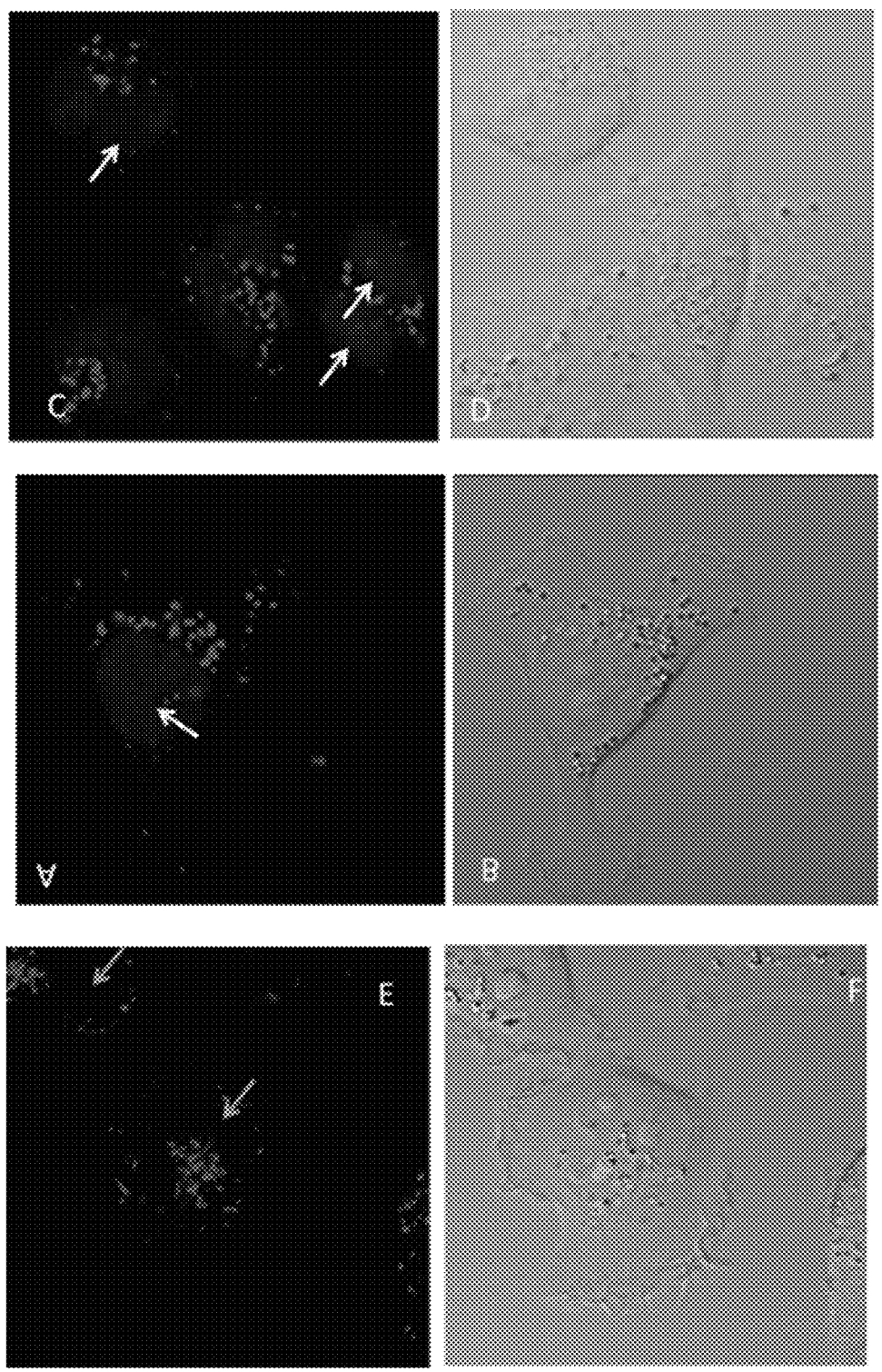
Fig 6. Confocal images of analog effects on subcellular distribution of a fluorescent oligonucleotide.

Fig. 7A. Effects on subcellular localization of oligonucleotide
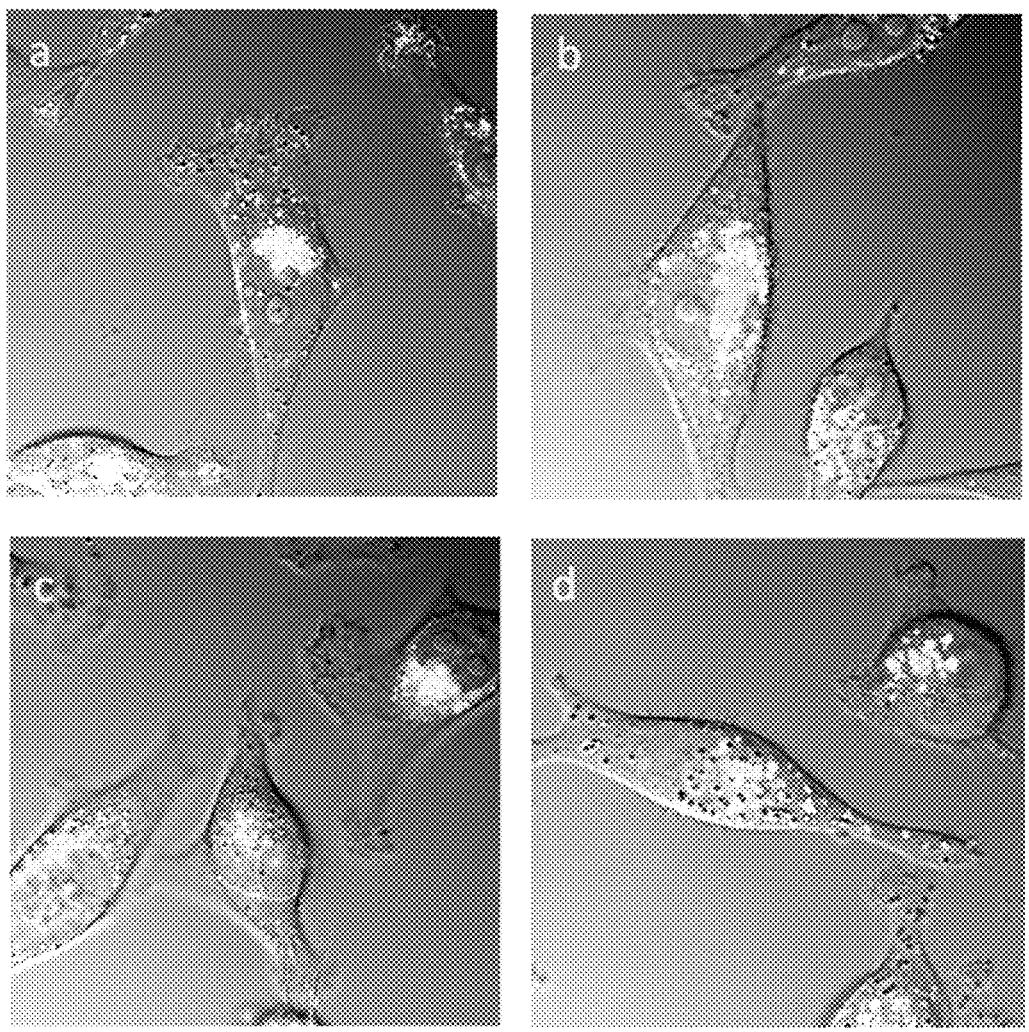
Fig. 7B.
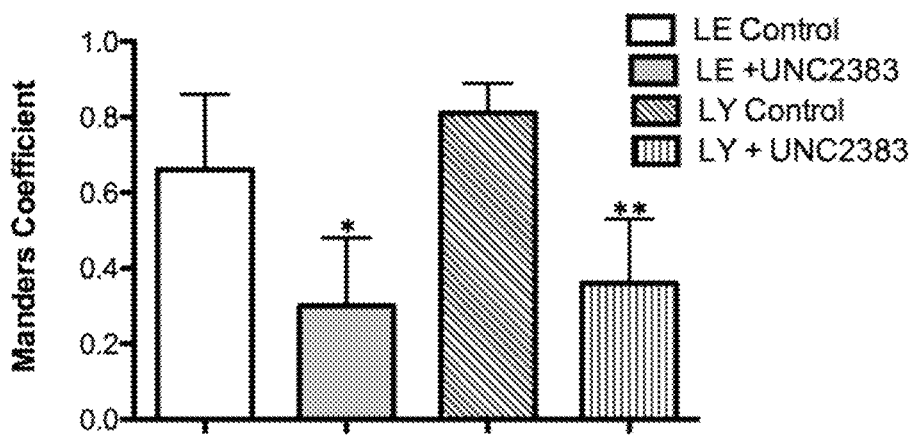

Fig 8. Confocal images of analog effects on subcellular distribution of a fluorescent oligonucleotide.
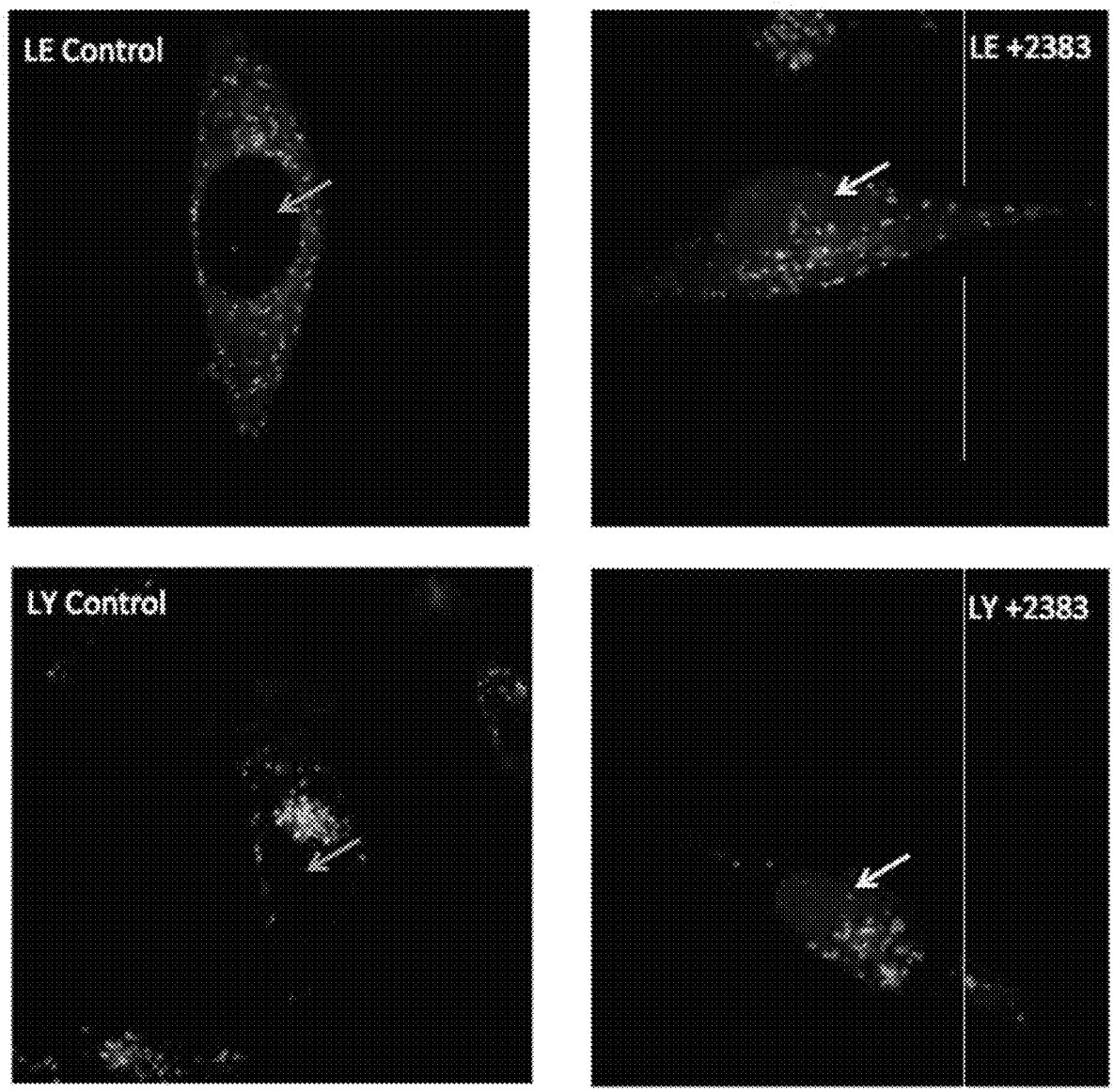

Fig. 9A Effects on lysosomes
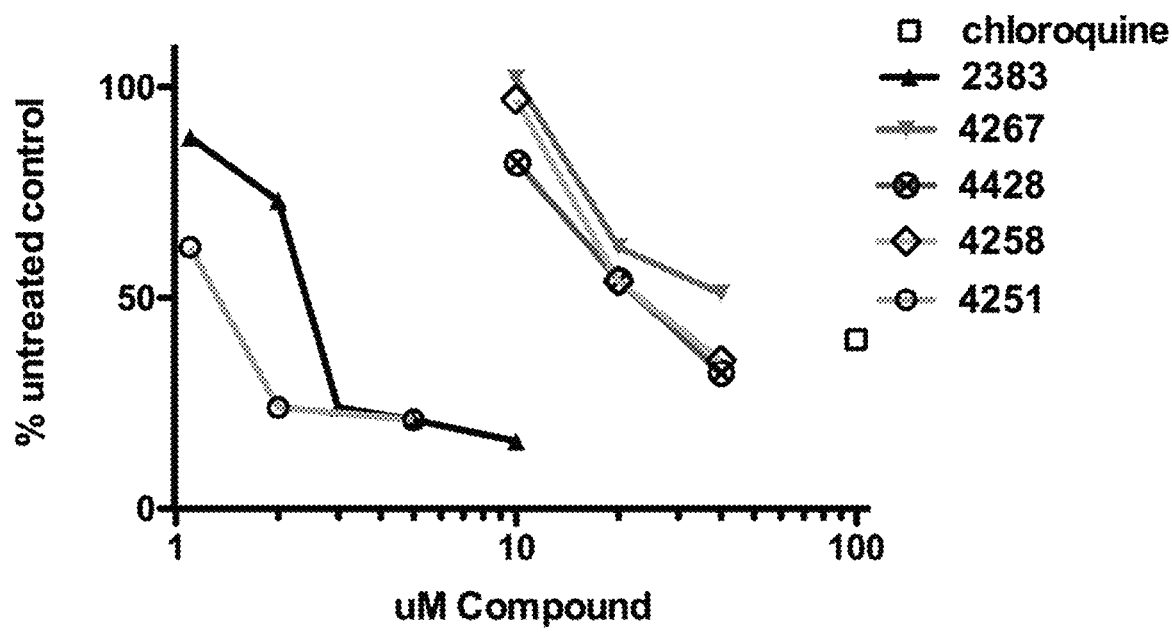
Fig. 9B
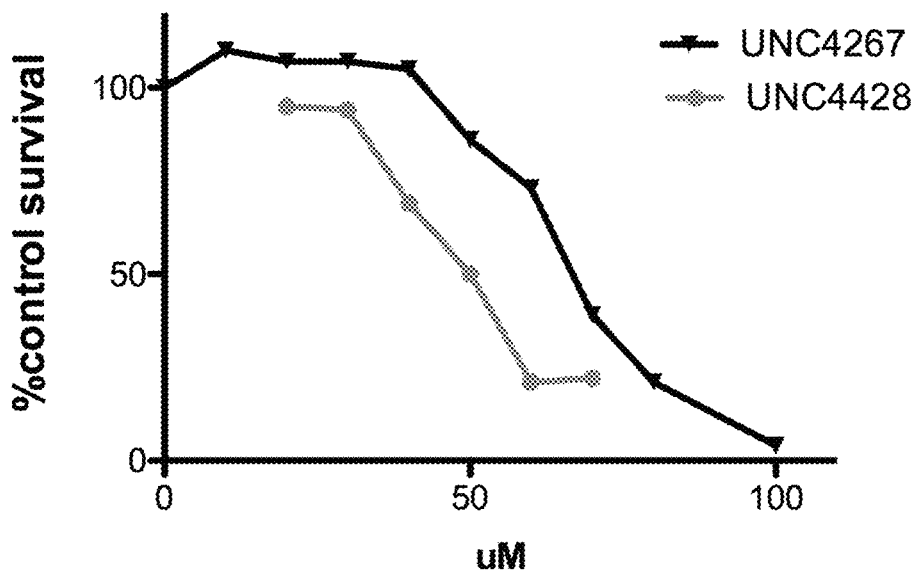

Fig. 10A-10F. In vivo effects-mRNA and protein expression correction
Fig. 10A
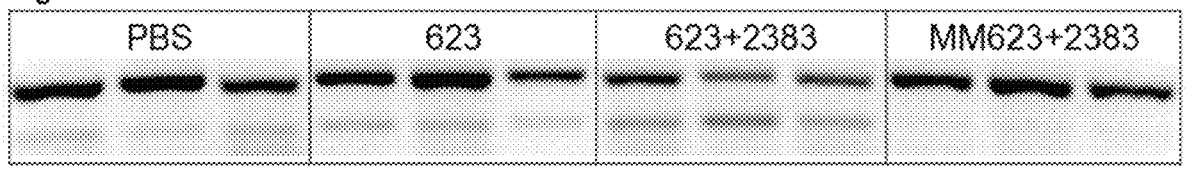
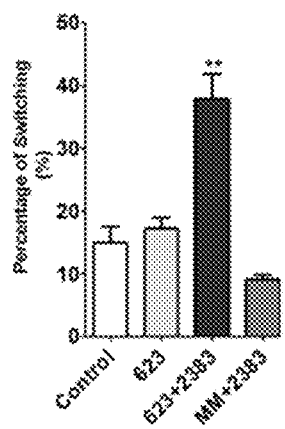
Fig. 10B
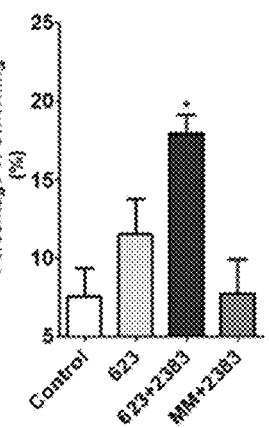
Fig. 10C
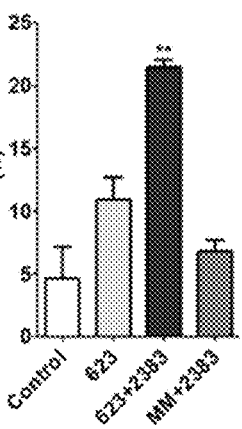
Fig. 10D
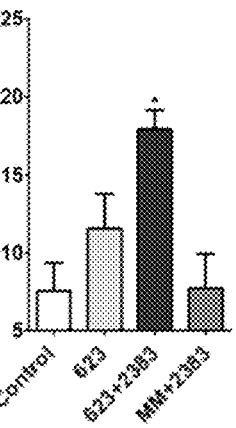
Fig. 10E
Fig. 10F
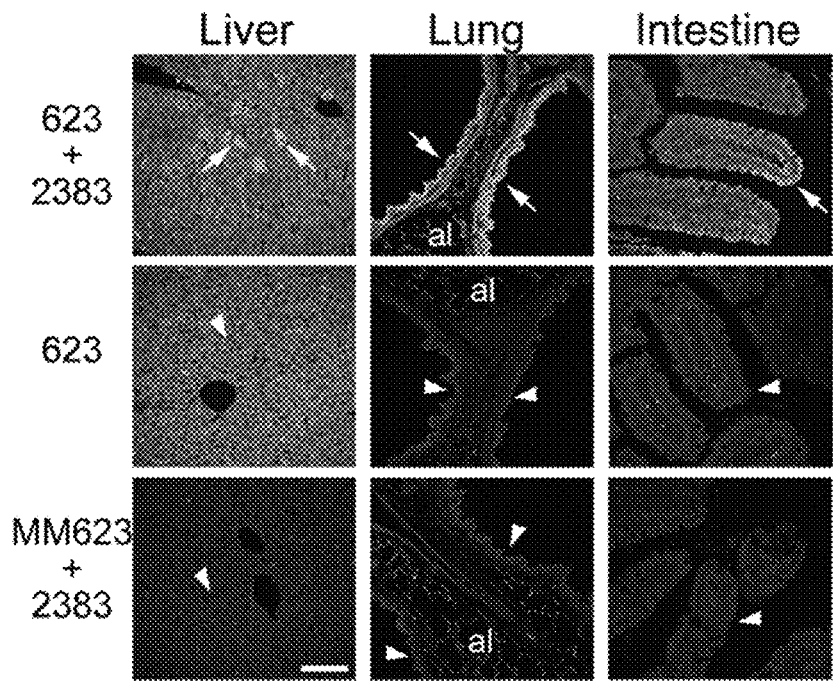

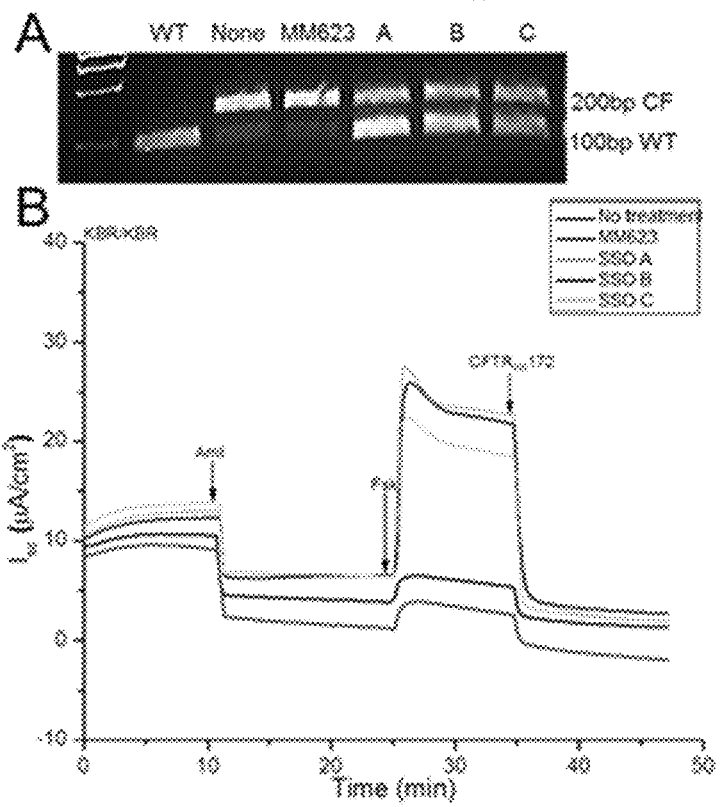
Fig. 11. CFTR activity restored to CF splicing mutation 3849+10kbC-T
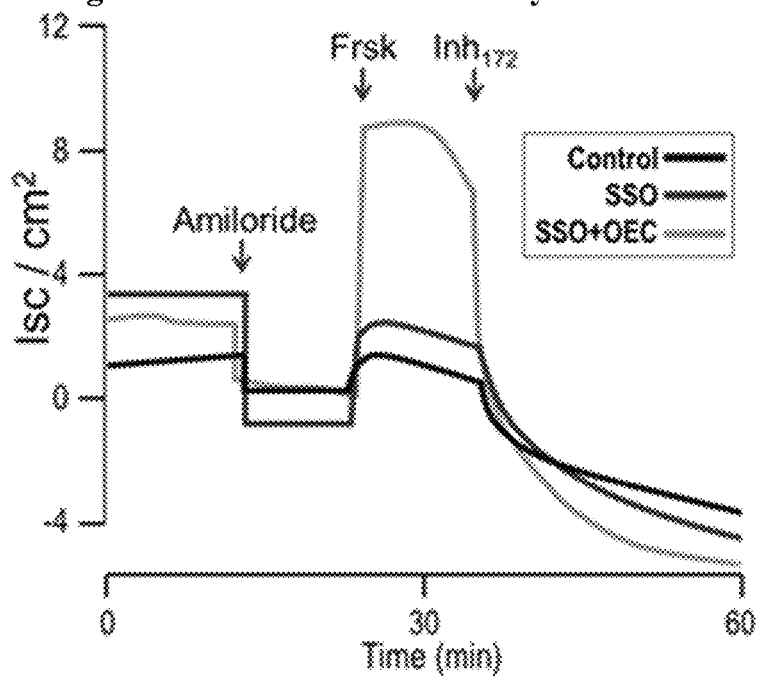
Fig. 12. OEC Mediated Delivery of a SSO Fig. 13. Protein expression correction in EGFP654 mouse-derived well-differentiated tracheal cells.
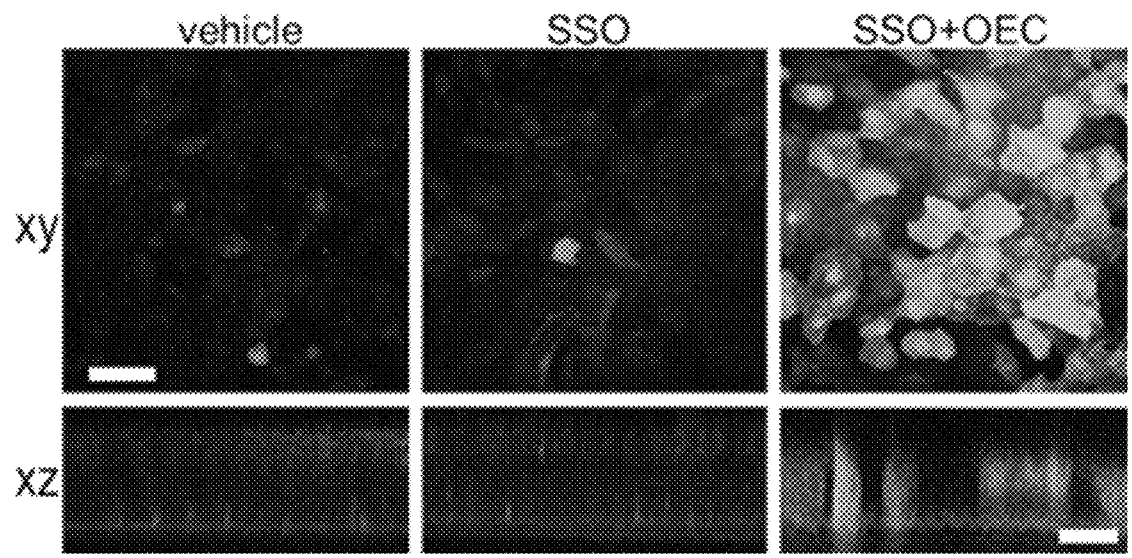
Fig. 14. Confocal images of OEC effects on subcellular distribution of a fluorescent oligonucleotide in well-differentiated primary human bronchial cells.
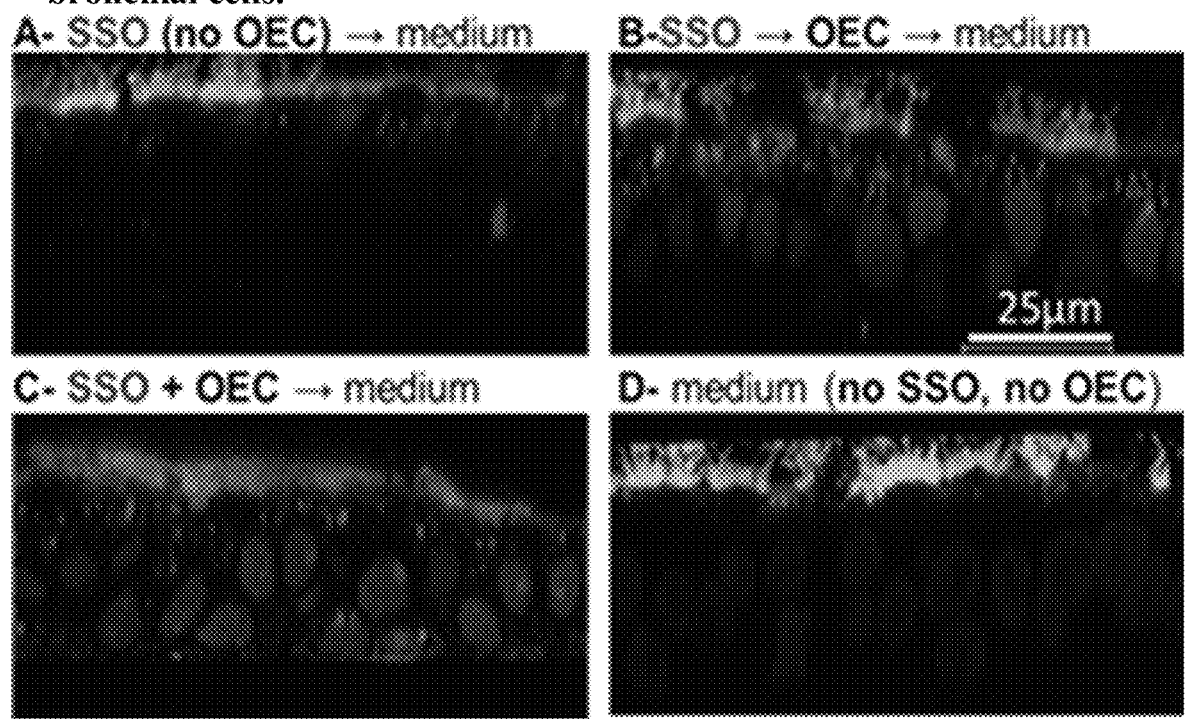

Splicing mutation correction with SSO P-PMO in combination with OEC
Fig.15A. P-PMO & OEC correction of 654EGFP expressed in HeLa cells
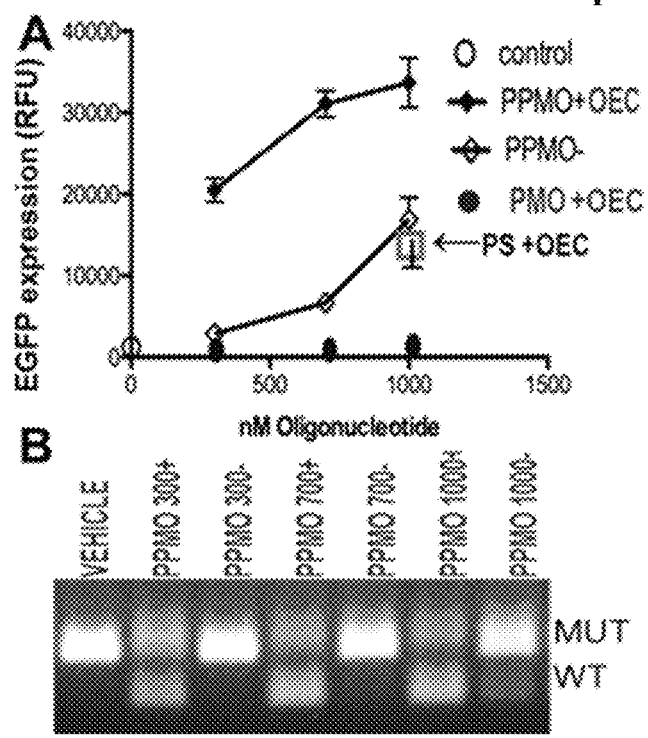

Fig. 15B. P-PMO & OEC correction of 654EGFP in primary cultures of tracheal epithelial cells (MTEC) derived from the 654EGFP mouse.
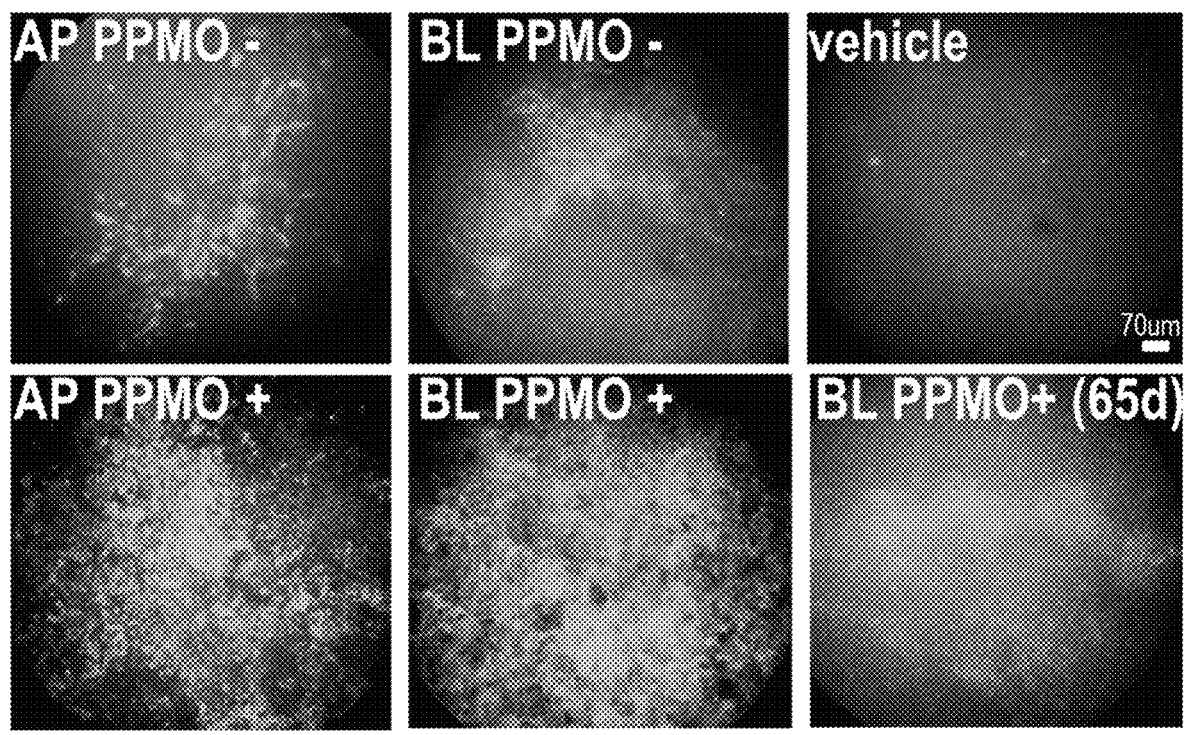

BENZIMIDAZOLES THAT ENHANCE THE ACTIVITY OF OLIGONUCLEOTIDES

CROSS REFERENCE TO RELATED APPLICATIONS

This application claims the benefit of U.S. Provisional Application No. 62/670,431 filed May 11, 2018, Kreda et al., which is hereby incorporated by reference in its entirety.

STATEMENT REGARDING FEDERALLY SPONSORED RESEARCH OR DEVELOPMENT

This invention was made with government support under Grant No. CA151964, CA170332 and TR001330 awarded by the National Institutes of Health. The United States Government has certain rights in the invention.

1. FIELD

The present disclosure provides methods, compounds and compositions for delivering nucleic acids to a cell of interest. In particular, it provides salts that are particularly effective in delivering nucleic acids to cells in the lung for disorders such as cystic fibrosis (CF).

2. BACKGROUND

2.1. Introduction

There have been numerous clinical trials involving various types of oligonucleotides including 'classic' antisense (AS), siRNAs, and splice switching oligonucleotides (SSOs), testifying to the immense interest in this broad therapeutic approach. Nonetheless, oligonucleotide-based therapies face a key problem regarding the inefficient access of oligonucleotides to their sites of action in the nucleus or cytosol of tissue cells. This problem has meant that large doses must be given to attain therapeutic effects thus risking drug-related toxicities, or that complex delivery systems such as cationic lipid or polymer nanoparticles must be used thus creating toxicity and biodistribution problems associated with the delivery system itself. Therefore it is clear that the discovery of alternative strategies to enhance the access of oligonucleotides to their intracellular targets will have substantial value for oligonucleotide-based pharmacology and therapeutics.

Oligonucleotides are usually internalized via endocytosis and then traffic through various membrane-bound vesicular compartments. Cells employ multiple distinct endocytotic uptake mechanisms including the 'classic' clathrin pit pathway, the caveolar pathway, one or more caveolin and clathrin-independent pathways, and macropinocytosis. Initial uptake is followed by trafficking into a variety of endomembrane compartments including early/sorting endosomes, late endosomes/multi-vesicular bodies, lysosomes, and the trans-Golgi network (TGN). Most of the oligonucleotide accumulated in cells remains sequestered in endomembrane vesicles and is pharmacologically inert, but a small fraction escapes to the cytosol and nucleus to permit activity. Recent reports have found that the route of uptake and pathway of intracellular trafficking can have a strong effect on the pharmacological activity of the oligonucleotide; there are productive and less productive pathways. These observations suggest that if it were possible to influence the intracellular trafficking of oligonucleotides, and their release from endomembrane compartments, one might be able to substantially enhance their pharmacological effects and/or the physiological activity thereof. See, e.g., R. Juliano et al., *Small Molecules that Enhance the Activity of Oligonucleotides*, PCT Application WO 2013/123217 (22 Aug. 2013).

It is clear that siRNA, antisense oligonucleotides (ASOs) and splice switching oligonucleotides (SSOs) have the potential to treat multiple diseases, particularly those that are not addressable with small molecule drugs. Importantly, the last few years have seen FDA approval of several oligonucleotide-based therapeutics most notably the ASO mipomersen for familial hypercholesterolemia and the SSOs eteplirsen and nusinersen for DMD and SMA respectively. A siRNA therapeutic (patisiran, ONPATTRO®) was approved in 2018 for treatment of hereditary transthyretin-mediated amyloidosis in adults.

3. SUMMARY OF THE DISCLOSURE

The disclosure provides a compound having the Formula I:

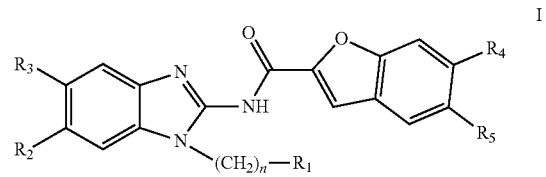

wherein: $R_1$ is $-NR_6R_7$, an N-containing heterocycle or an N-containing heterocycloalkyl; $R_2$-$R_5$ are each independently $C_{1-8}$ alkyl, $C_{1-8}$ alkoxy, $C_{2-8}$ alkenyl, $C_{3-8}$ alkynyl, $C_{3-8}$ cycloalkyl, H or halogen; $R_6$ and $R_7$ are each independently $C_{1-8}$ alkyl or H; or $R_6$ and $R_7$ together make a 4-8-member ring which may be substituted with one or more nitrogens; and n is an integer between 1 and 8; or a pharmaceutically acceptable salt thereof.

In some embodiments, n may be 2-4 and the N-containing heterocycle or N-containing heterocycloalkyl may be an imidazole, a morpholine, a piperidine, a piperidone, a piperazine, or a pyrrolidine group.

In other embodiments n may be 2-4 and $R_2$-$R_5$ each independently may be $C_{1-4}$ alkyl, $C_{1-4}$ alkoxy, H or halogen. The halogen may be bromine or chorine.

The disclosure also provides composition comprising the compound of Formula I above, wherein the composition further comprises a compound having the Formula II:

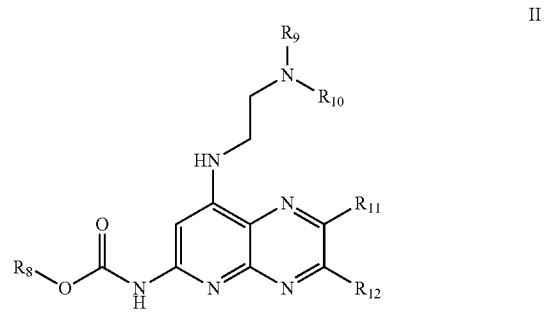

wherein: $R_8$ is $C_{1-8}$ alkyl or a linking group; $R_9$ is $C_{1-8}$ alkyl or a linking group; $R_{10}$ is $C_{1-8}$ alkyl; $R_{11}$ and $R_{12}$ are each independently aryl, $C_{1-8}$ alkyl, $C_{1-8}$ alkoxy, amino, H, halogen, or heteroaryl; or a pharmaceutically acceptable salt thereof. Compounds of Formula II and their synthesis are disclosed in U.S. Patent Publication US2017/0130222, the contents of which are hereby incorporated by reference in its entirety.

In some embodiments, the compound of Formula II has the structure:

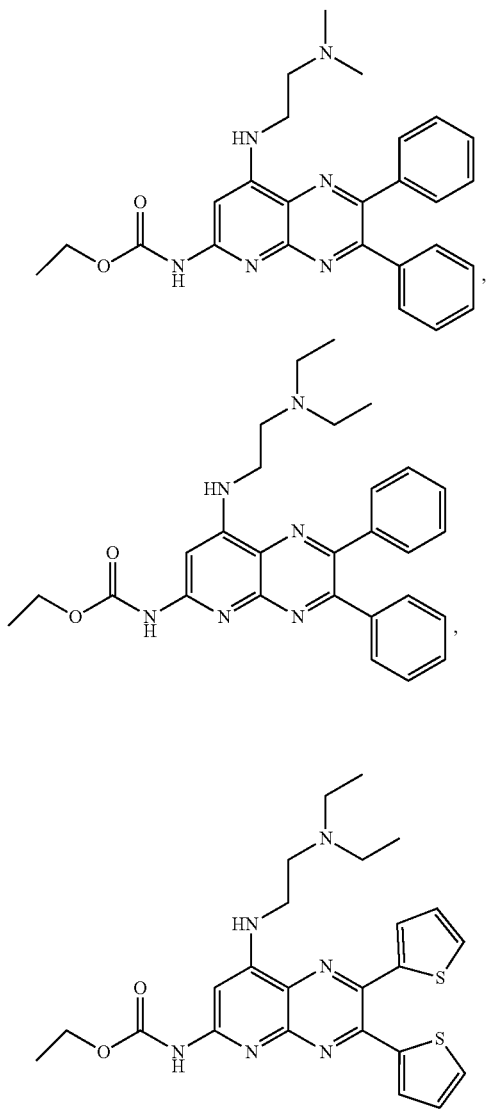

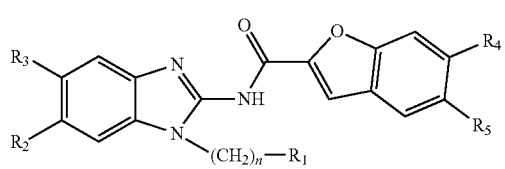

or a pharmaceutically acceptable salt thereof.

The disclosure also provides a composition comprising an oligonucleotide and a compound having the Formula I:

wherein: $R_1$ is $-NR_6R_7$, an N-containing heterocycle or an N-containing heterocycloalkyl; $R_2$-$R_5$ are each independently $C_{1-8}$ alkyl, $C_{1-8}$ alkoxy, $C_{2-8}$ alkenyl, $C_{3-8}$ alkynyl, $C_{3-8}$ cycloalkyl, H or halogen; $R_6$ and $R_7$ are each independently $C_{1-8}$ alkyl or H; or $R_6$ and $R_7$ together make a 4-8-member ring which may be substituted with one or more nitrogens; and a pharmaceutically acceptable carrier.

The composition above may further comprises a compound having the Formula II:

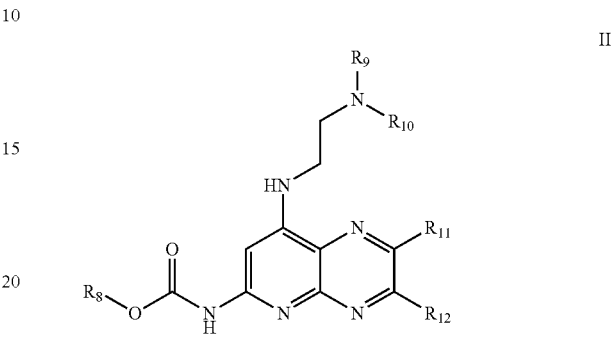

wherein: $R_8$ is $C_{1-8}$ alkyl or a linking group; $R_9$ is $C_{1-8}$ alkyl or a linking group;

$R_{10}$ is $C_{1-8}$ alkyl; $R_{11}$ and $R_{12}$ are each independently aryl, $C_{1-8}$ alkyl, $C_{1-8}$ alkoxy, amino, H, halogen, or heteroaryl; or a pharmaceutically acceptable salt thereof.

In the composition above, the compound of Formula II may have the structure:

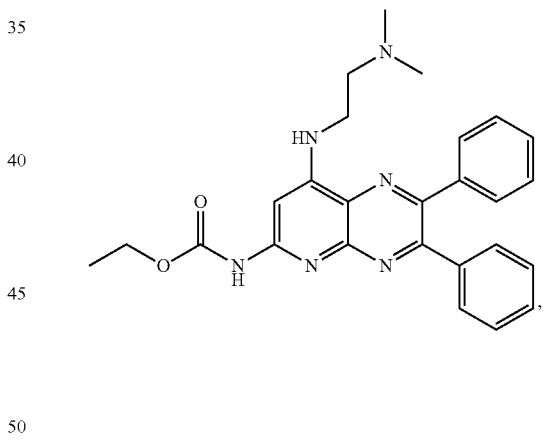

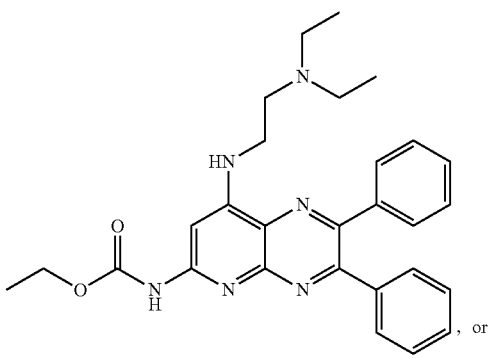

-continued

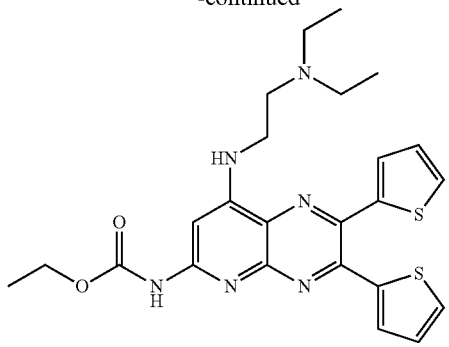

or a pharmaceutically acceptable salt thereof.

In the composition above, the oligonucleotide may be a phosphorodiamidate morpholino oligomer (PMO) or a peptide-conjugated PMO.

The disclosure also provides a method of administering an oligonucleotide of interest to a cell which comprises administering to the cell the oligonucleotide and a compound of Formula I:

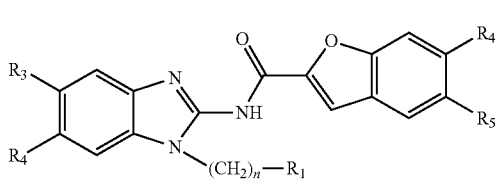

wherein: $R_1$ is —$NR_6R_7$, an N-containing heterocycle or an N-containing heterocycloalkyl; $R_2$-$R_5$ are each independently $C_{1-8}$ alkyl, $C_{1-8}$ alkoxy, $C_{2-8}$ alkenyl, $C_{3-8}$ alkynyl, $C_{3-8}$ cycloalkyl, H or halogen; $R_6$ and $R_7$ are each independently $C_{1-8}$ alkyl or $R_6$ and $R_7$ together make a 4-8-member ring which may be substituted with one or more nitrogens; or a pharmaceutically acceptable salt thereof.

The method may further comprise administering to the cell a compound having the Formula II:

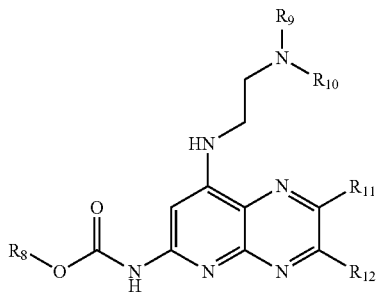

wherein: $R_8$ is $C_{1-8}$ alkyl or a linking group; $R_9$ is $C_{1-8}$ alkyl or a linking group; $R_{10}$ is $C_{1-8}$ alkyl; $R_{11}$ and $R_{12}$ are each independently aryl, $C_{1-8}$ alkyl, $C_{1-8}$ alkoxy, amino, H, halogen, or heteroaryl; or a pharmaceutically acceptable salt thereof.

In the method above, the oligonucleotide may be a phosphorodiamidate morpholino oligomer (PMO) or a peptide-conjugated PMO. The cell may be a mammalian cell. The method is carried out in vitro or in vivo.

In one embodiment, the method is carried out by administering the oligonucleotide to the cell, and concurrently administering the compound having formula I to the cell. In another embodiment, the compound having formula I is administered after the oligonucleotide is administered to the cell.

For the methods above, the oligonucleotide may be single stranded. In some embodiments, the oligonucleotide may be from 2, 4, 6 or 8 to 100 or 200 nucleotides in length. The oligonucleotide may be an antisense oligonucleotide. Alternatively, the oligonucleotide may be a splice switching oligonucleotide or an siRNA.

In some embodiments of the methods described herein, the cell may be a lung cell or an airway cell, e.g., a human bronchial epithelial cell (HBEC), a human nasal epithelial cell (HNEC), a mouse tracheal epithelial cell (MTEC), a human alveolar type I or type II cell, a human lung submucosal gland cell, a human lung leucocyte, or a human lung inflammatory cell.

The disclosure also provides a method of treating a disorder in a subject by administering an oligonucleotide of interest to the subject and a pharmaceutically acceptable salt of compound of Formula I:

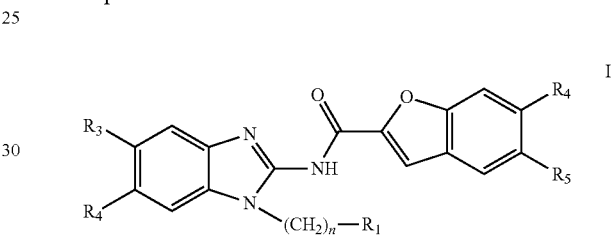

wherein: $R_1$ is —$NR_6R_7$, an N-containing heterocycle or an N-containing heterocycloalkyl; $R_2$-$R_5$ are each independently $C_{1-8}$ alkyl, $C_{1-8}$ alkoxy, $C_{2-8}$ alkenyl, $C_{3-8}$ alkynyl, $C_{3-8}$ cycloalkyl, H or halogen; $R_6$ and $R_7$ are each independently $C_{1-8}$ alkyl or H; or $R_6$ and $R_7$ together make a 4-8-member ring which may be substituted with one or more nitrogens.

The method of treatment may further comprise administering to the subject a compound having the Formula II:

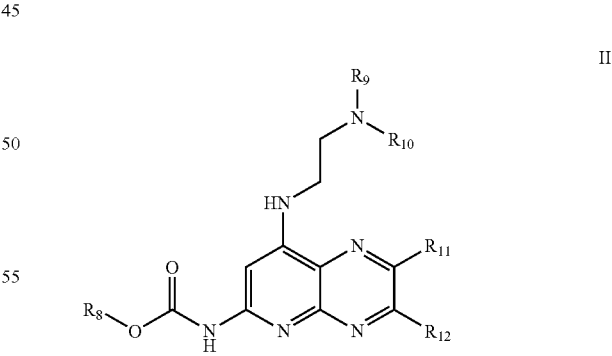

wherein: $R_8$ is $C_{1-8}$ alkyl or a linking group; $R_9$ is $C_{1-8}$ alkyl or a linking group;

$R_{10}$ is $C_{1-8}$ alkyl; $R_{11}$ and $R_{12}$ are each independently aryl, $C_{1-8}$ alkyl, $C_{1-8}$ alkoxy, amino, H, halogen, or heteroaryl; or a pharmaceutically acceptable salt thereof.

In some embodiments the oligonucleotide is a phosphorodiamidate morpholino oligomer (PMO) or a peptide-conjugated PMO.

In the methods above the disorder may be a lung disorder. The disorder may be cystic fibrosis (CF). The oligonucleotide may specifically hybridize with a cystic fibrosis transmembrane conductance regulator (CFTR) gene. The oligonucleotide also may be a splice switching oligonucleotide specific for a mutation in a cystic fibrosis transmembrane conductance regulator (CFTR) gene. The mutation in the CFTR gene may be a CF-causing CFTR splicing mutation such as the 3849+10 kbC→T mutation or other CF-causing splicing mutations.

Alternatively, the oligonucleotide may be an antisense oligonucleotide that specifically targets an epithelial sodium channel (ENaC) gene.

The lung disorder may also be chronic obstructive pulmonary disease (COPD), asthma, idiopathic pulmonary fibrosis (IPF). For IPF the oligonucleotide may be an antisense oligonucleotide that specifically targets MUC5AC or MUC5B. The disorder may also be other diseases with excessive production of MUC5AC or MUC5B, including pathologies in ear, eye and nose with excessive mucin production))

The disorder may also be primary ciliary dyskinesia, targeting with oligonucleotides mutations specific for different ciliary genes.

The invention is well suited to improve the delivery of ASOs or SSOs to human bronchial airway and alveolar epithelial cells and other cellular types associated with the airways, the nose and the lung. Examples include basal epithelial cells, bronchial epithelial cells (HBEC), ciliated epithelial cells, club cells, or goblet cells.

In addition, the compounds and methods of the disclosure may be useful for adenocarcinoma or other cancers associated with mucins, using antisense oligonucleotide that specifically targets MUC5AC or MUC5B.

4. BRIEF DESCRIPTION OF THE FIGURES

FIG. 1A. Schematic summary. Oligonucleotides (red ribbons) enter the cell by endocytosis and then traffic to the early endosomes (EE), late endosomes (LE), lysosomes (LY) and trans-Golgi (TG). The compounds disclosed herein such as UNC2383 cause partial release of oligos from LEs and leakage of protons from LYs.

Figure 1B:
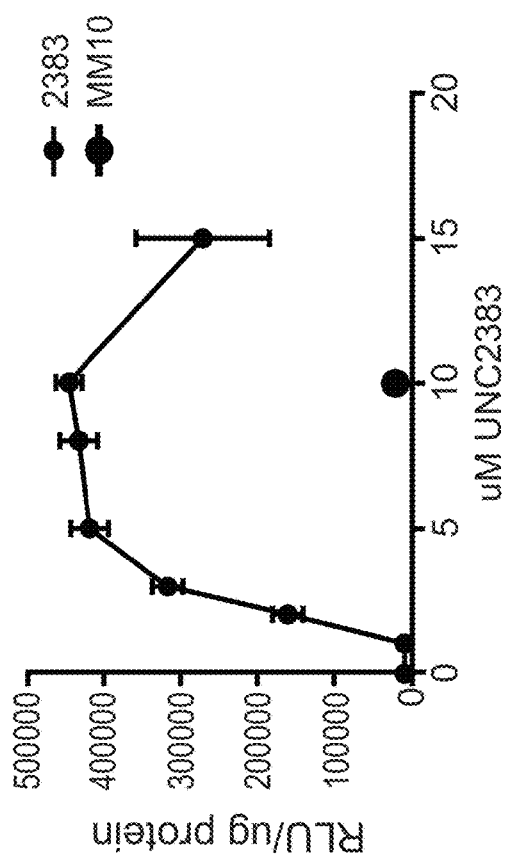
Figure 1C:
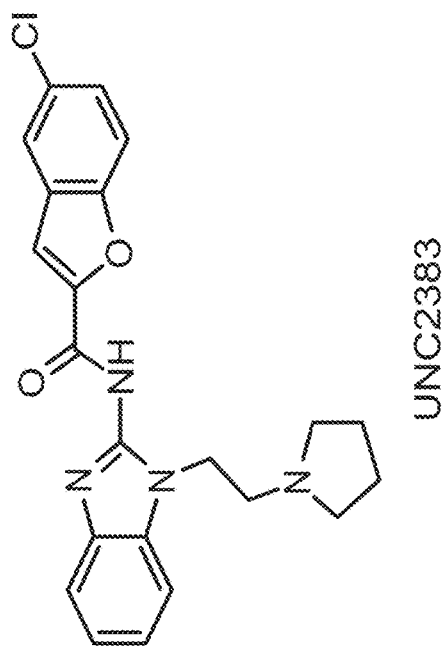
Figure 1E:
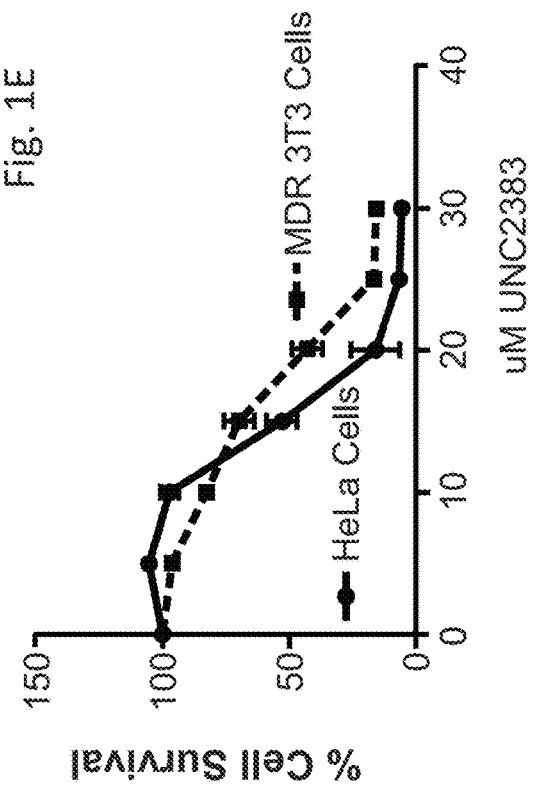
Figure 1D:
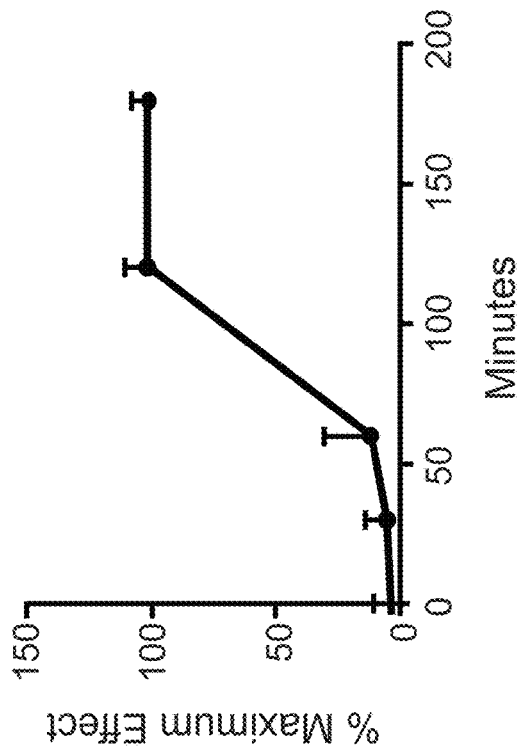

FIG. 1B-1E. Effects with SSOs. FIG. 1B Structure of UNC2383. FIG. 1C Compound 2383 enhances SSO effects. Cells were incubated in 24-well plates with 100 nM SSO623 or its mismatched control (MM) for 16 h in DMEM+10% FBS, rinsed and then treated with various concentrations of 2383 for 2 h. The cells were then rinsed and incubation continued for an additional 4 h in DMEM+10% FBS. Cells were rinsed twice in PBS and luciferase activity (RLU) and cell protein determined. The larger round symbol indicates the MM oligonucleotide. Means+/−SE. N=3. FIG. 1D Kinetics of 2383 action. Cells were preloaded with 100 nM SSO623 and then exposed to 2383 for various periods after which the compound was removed. The cells were further incubated and then luciferase and protein determined. The total time of incubation in each case was 6 h. FIG. 1E Cytotoxicity of 2383. HeLa Luc705 or NIH-3T3-MDR cells were exposed to 2383 as in (FIG. 1C) then incubated for 24 h in DMEM plus 10% FBS and tested using the Alamar Blue cytotoxicity assay. Means+/−SE. N=3.

FIG. 2. Structure of UNC2383 Analogs.

FIG. 3. Effect and Cytotoxicity of Analogs. The effect of selected UNC2383 analogs on luciferase induction by SSO623 was measured as described in Methods and in the legend of FIG. 1B-1E. Cytotoxicity was measured using the Alamar Blue method as in FIG. 1E. MM10 is the effect of 10 uM compound in the presence of a mismatched oligonucleotide. Means and SE. N=3.

FIG. 4. Effects with ASOs. Reduction of Pgp expression. NIH 3T3-MDR cells were incubated with 100 nM anti-MDR1 ASO or a mismatched (MM) control for 16 h in DMEM+1% FBS. Cells were rinsed and then treated with 10 μM UNC2383 for 2 h. The compound was removed, and the cells further incubated for 48 h. Expression of Pgp on the cell surface was determined by treating cells with Alexa 488 labeled anti-Pgp monoclonal antibody and binding quantitated by flow cytometry (PE(A)=units of fluorescence intensity). Treatment with ASO complexed with Lipofectamine 2000 (L2K) was a positive control. Y axis, cell counts; X axis, Alexa 488 fluorescence. In the inset, the ordinate is the percentage of cells in Window 1 (reduced Pgp expression). Means±SE, N=3.

Figure 5B:
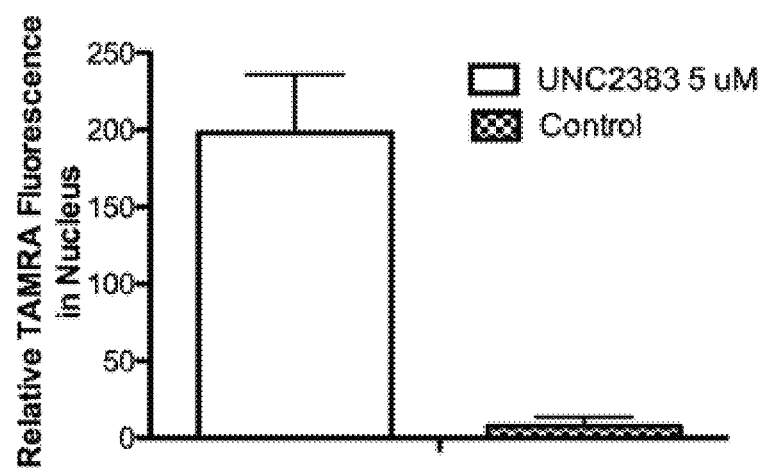

FIG. 5A-5B. Effect on endomembrane permeability. FIG. 5A: HeLa Luc 705 cells (50 000) were seeded into glass-bottom dishes and incubated at 37° C. for attachment. Alexa 488-Dextran 10K (200 μg/mL) or TAMRA SSO 623 (2.5 μM) were added into the medium and the cells incubated for 24 h. Cells were washed with PBS and then placed back in the medium and treated with UNC2383 for 2 h or maintained as controls. Cells were rinsed after drug treatment. Live cells were imaged with an Olympus FV1200 or a Zeiss LSM710 confocal microscope. For the studies with Alexa 488 Dextran, the controls are shown in image panels a and b while cells treated with 10 μM UNC2383 are in image panels c and d. For studies with TAMRA SSO 623, the control is image panel e, while image panel f shows cells treated with 5 μM UNC2383. Images e and f are composites of TAMRA, Hoechst, and DIC images, and the pink coloration in f indicates overlap of the TAMRA and Hoechst fluorescence. Images are typical of three independent assays. Intensity settings were identical for fluorescence images with or without UNC2383. FIG. 5B quantitates the TAMRA fluorescence in the nucleus for controls versus cells treated with 5 μM UNC2383, as measured using Fiji software, with Hoechst stain used to delineate the nucleus (N=12).

FIG. 6. Confocal images of compound effects on nuclear distribution of a fluorescent oligonucleotide. Methods were similar to those used in FIG. 5A-5B. Nuclei showing accumulation of fluorescent oligonucleotide (a TAMRA labeled SSO) are indicated with bright arrows. Nuclei lacking fluorescence are indicated with gray arrows. Panels A, B UNC4267 30 μM; Panels C, D UNC4258 30 uM; Panels E, F controls FIG. 7A-7B. Effects on subcellular localization of oligonucleotide. FIG. 7A: HeLa Luc 705 cells were dually labeled with TAMRA SSO and, by using baculovirus vectors, with GFP-Rab7 or GFP-LAMP1 as markers for late endosomes (LE) or lysosomes (LY), respectively. Subsequently, cells were treated for 2 h with 5 μM UNC2383 or maintained as controls. Composite images showing TAMRA fluorescence, GFP, and DIC are provided. Overlap is indicated in white. Panel (a) GFP-LAMP1 plus TAMRA, control; (b) GFP-LAMP1 plus TAMRA with 5 μM UNC2383; (c) GFP-Rab7 plus TAMRA, control; (d) GFP-Rab7 plus TAMRA with 5 μM UNC2383. FIG. 7B shows a plot of the Manders' Correlation Coefficients for TAMRA versus GFP in control cells and cells treated with 5 μM UNC2383 (N=12). The differences in Manders' Coefficient in control versus treated cells were significant at the 5% level for LE and at the 1% level for LY, both using the paired t-test.

FIG. 8. Confocal images of compound effects on overlap of a fluorescent oligonucleotide with GFP marker proteins for late endosomes (LE) or lysosomes (LY). Methods were similar to those used in FIG. 7A-7B. Overlap of TAMRA-SSO and GFP is seen as gray. Control cells and cells treated with 5 uM UNC2383 are shown. White arrows indicate nuclei showing TAMRA fluorescence; gray arrows indicate 'empty' nuclei. DIC images have been removed for clarity.

Figure 9C:
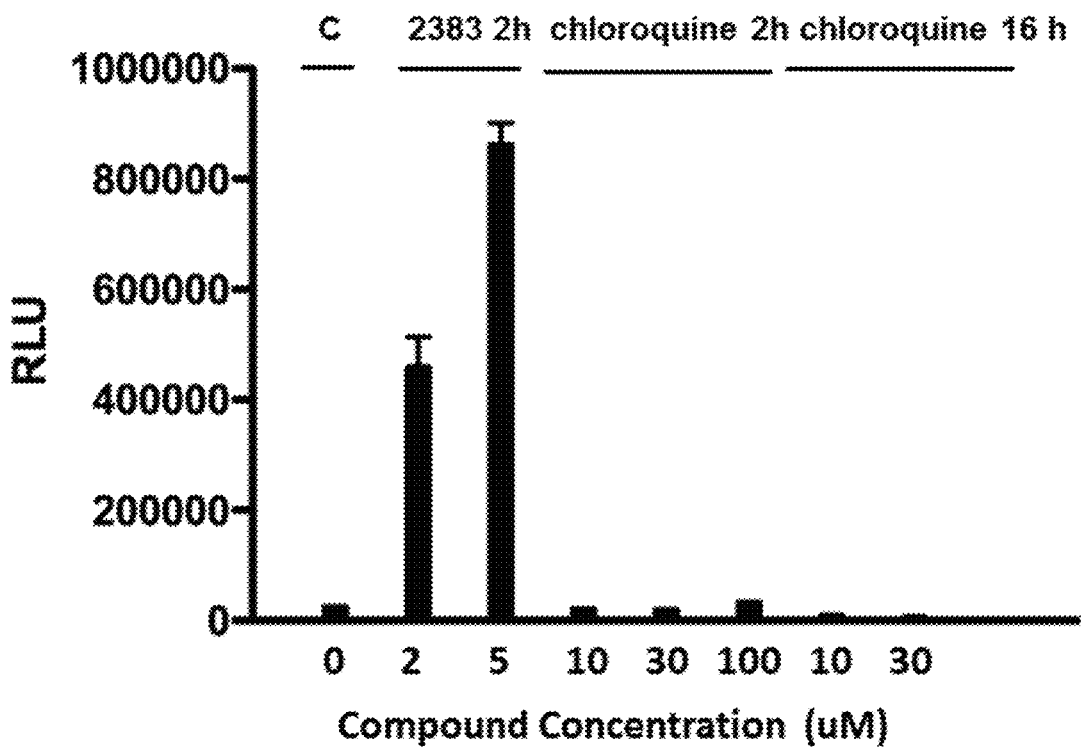
Figure 9D:
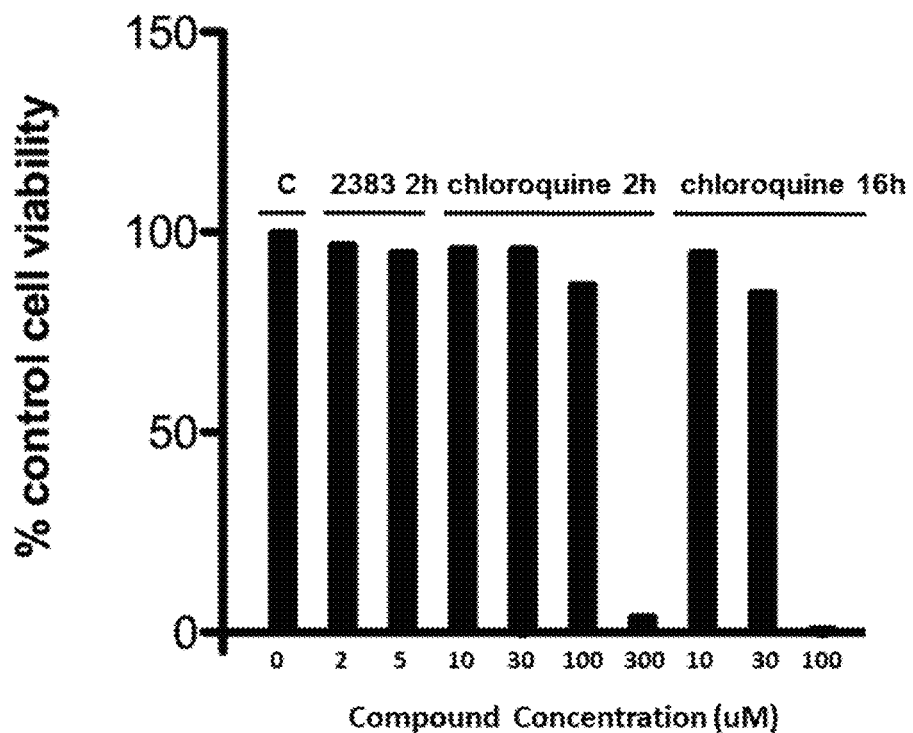

FIG. 9A-9D. Effects on lysosomes. FIG. 9A: Lysotracker uptake. Accumulation of Lysotracker Red in HeLa Luc 705 cells was measured after a 2 h exposure of cells to the indicated concentrations of various analogs. The lysosomotropic compound chloroquine was included as a positive control. Means of triplicate determinations are shown. The color-coded numbers refer to the fold increase in luciferase induction attained by the concentration of analog associated with the adjacent symbol on the graph. The numbers are taken from the data of FIG. 1C for UNC2383 and FIG. 4 for UNC4267, UNC4258, and UNC4428. FIG. 9B: LT50 vs TC50. The plot shows the ratio of the concentration of analog required for 50% inhibition of Lysotracker Red uptake (LT50) to the concentration required for 50% cell killing (TC50) under the same conditions of exposure. Nonlinear regression was calculated using Prism software. The $R^2$ value for the plot is 0.91. FIG. 9C: 2383 vs chloroquine; luciferase induction. HeLa Luc705 cells were exposed to SSO623 and then treated with various concentrations of UNC2383 or chloroquine for 2 h and then tested for luciferase induction following the methods described in FIG. 1B-FIG. 1E. In a subset of the experiment, cells were exposed to chloroquine for 16 h rather than 2 h. Means±SE, N=3. FIG. 9D: UNC2383 vs chloroquine; cytotoxicity. After treatment as in c, the cells were tested for viability using the Alamar Blue assay. Means, N=3.

FIG. 10A-10E. In vivo effects-RNA. EGFP654 mice were treated with SSO623 or a mismatched control (MM) and then received UNC2383 or diluent (N=3). RT-PCR with gel analysis was used to detect correctly or incorrectly spliced EGFP mRNA. The gel images were quantitated using Fiji software. Gel image for liver FIG. 10A. The lower band (87 bp) is correctly spliced EGFP mRNA, while the upper band (160 bp) is uncorrected. FIG. 10B-10E Quantitation of splice correction in liver FIG. 10B, kidney FIG. 10C, intestine FIG. 10D, and lung FIG. 10E. The bars indicate the ratio of correctly spliced to incorrectly spliced mRNA×100. The differences between the SSO623-only samples and the SSO623 plus UNC2383 samples are statistically significant. FIG. 10F In vivo effects-protein. EGFP immunostaining was performed in liver, lung, and intestine tissue and analyzed by confocal microscopy. Increased EGFP signal was seen in groups of liver cells, epithelial cells lining the bronchi, and epithelial cells in the colonic crypts in mice treated with both SSO623 and UNC2383 (arrows) compared to matching tissues from control mice (arrowheads in control mouse tissues point to equivalent structures indicated by arrows in tissues from the SSO623 plus UNC2383 treated mice). Some nonspecific fluorescence signal was observed in the alveoli (al) in the lung tissue sections of all mouse groups. Nuclei were counter-stained with DAPI. Bar=70 um.

FIG. 11. CFTR activity restored to CF splicing mutation 3849+10 kbC-T using SSOs. SSOs were delivered in vitro by electroporation (~100% efficiency), CF primary cells were differentiated on permeable supports and tested. Panel A. PCR analysis. The lower band is the correctly spliced CFTR. Panel B. Functional correction by Ussing chamber analysis. Note, Ivactafor®/Kalydeco® treatment have minimal effect on these patient cells tested in parallel experiments.

FIG. 12. OEC Mediated Delivery of a SSO in 3849+10 kbC-T HBEC. Well-differentiated human bronchial epithelial cells (HBEC) derived from a 3849+10 kbC-T homozygous patient were incubated with corrective (LNA) SSO A from FIG. 1 (1 uM, overnight). Cells were then incubated with OEC UNC2383 in the luminal or serosal bath (4 uM, 2 hs). Both the SSO and OEC were added in cell growing medium. Seventy two hour later, HBEC were analyzed in Ussing chamber for CFTR function. Orkambi® was tested in parallel inserts. A significant enhancement of CFTR channel activity was observed only in cells treated with SSO+OEC (apical or basolateral); Orkambi® did not elicit correction; (n=3).

FIG. 13. EGFP654 Mouse tracheal cells. Well-differentiated tracheal epithelial cells derived from the EGFP654 mouse were treated basolaterally with 1 uM SSO PS623 (overnight) and apically with 3 uM OEC2383 (2 hr) or vehicle. Confocal microscopy images (xy, xz planes), bar=20 um. EGFP was notably expressed only in MTECs receiving SSO & (apical) OEC.

FIG. 14. SSO uptake in well-differentiated primary human bronchial cells. A & B, WD-HBEC were incubated basolaterally with TAMRA-SSO (100 nM) overnight, followed by 3 h incubation with vehicle (Panel A), or OEC7938 (10 M) (Panel B). In Panel C, HBEC were incubated overnight with both SSO+OEC. Panel D, HBEC with no SSO or OEC. In all conditions, HBEC were cultured further for 12 h, fixed in 4% paraformaldehyde and stained with Alexa Fluor 488®-wheat germen agglutinin to label cilia and plasma membrane, and DAPI (only D) to label nuclei, as a control. HBEC were examined by xz confocal microscopy with constant acquisition settings. SSO accumulated in intracellular vesicles, but localized at significant levels in the nuclei only in HBEC treated with OEC. Note the absence of WGA staining in lateral plasma membranes, indicating epithelial cell layer integrity.

FIG. 15A: Use of peptide-morpholino oligonucleotide conjugate (P-PMO) & OEC for splicing correction in EGFP654 HeLa cells. EGFP654 HeLa cells in 96 well plates were incubated overnight with SSOs P-PMO"654" (peptide conjugate), PMO "654" (no peptide conjugate) or PS654 (same nucleotide sequence as PM0654 but with phosphorothioate, 2' 0-Methyl chemical backbone) at concentrations specified in the figures. Then, cells were treated for 2 hs with 10 uM OEC7938 or OEC2383 (+) or vehicle (−). All compounds were added in cell growing media. After 24 h, cells were analyzed: A) EGFP fluorescence intensity measurements in live cells using a Tecan plate fluorimeter, n=3 (Values for PMO (−) or PMO (+) were at baseline). B) mRNA levels by RT-PCR showing expression of the mutant and corrected (wild type=wt) bands. Note, this is not quantitative PCR. The SSO morpholinos peptide conjugate and the OEC primarily act at two successive steps of the delivery process, namely cell uptake and endosomal escape. Thus, these compounds exhibit synergistic action on the delivery and pharmacological effect of the oligonucleotide.

FIG. 15B: P-PMO+OEC mediated splicing correction in EGFP654 MTEC. Well-differentiated cultures of primary tracheal cells (MTEC) derived from the EGFP654 mouse were treated with only one dose of P-PMO"654" (0.5 uM, overnight) followed by vehicle (−) or OEC2383 or OEC7938 (+), (10 uM, 2 hs). Both the SSO and OEC were added in cell medium either into the basolateral (BL, 400 ul) or the apical (AP, 30 ul) sides. MTEC were imaged in face at low mag. with a 10× lens in a fluorescence microscope, after 48 hs and 65 days post-treatment. All wells had the same total cell numbers. Vehicle controls<10 cells/well; n=3, bar=70 um. 1) Basolateral delivery of one treatment of P-PMO and OEC corrected>70% MTEC/well at 48 hs post-treatment. EGFP expression was still evident in large groups of cells after 65 days. 2) Apical delivery of one treatment of P-PMO followed by OEC also displayed remarkable splicing correction and thus, EGFP expression.

5. DETAILED DESCRIPTION OF THE DISCLOSURE

The present disclosure will now be described more fully hereinafter. This disclosure may, however, be embodied in different forms and should not be construed as limited to the embodiments set forth herein. Rather, these embodiments are provided so that this disclosure will be thorough and complete, and will fully convey the scope to those skilled in the art.

The terminology used in the description of the disclosure herein is for the purpose of describing particular embodiments only and is not intended to be limiting. As used in this disclosure and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this disclosure belongs. All publications, patent applications, patents and other references mentioned herein are incorporated by reference in their entirety.

5.1. Definitions

"Alkenyl" refers to an unsaturated branched, straight-chain or cyclic alkyl group having at least one carbon-carbon double bond derived by the removal of one hydrogen atom from a single carbon atom of a parent alkene. The group may be in either the Z- and E-forms (or cis or trans conformation) about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. The alkenyl group may be substituted or unsubstituted. In certain embodiments, an alkenyl group has from 2 to 20 carbon atoms. Alternatively, an alkenyl group may comprise from 2 to 5 carbon atoms, 5 to 9 carbon atoms, 9 to 12 carbon atoms, or 12 to 20 carbon atoms. Where the alkenyl group is attached to a nitrogen or other heteroatom, the first two carbons of the chain will be saturated, e.g., $N(CH_2)_2CH=CCHR$.

"Alkoxy" refers to a radical —OR where R represents an alkyl, alkenyl, cycloalkyl, aryl, or heteroaryl group as defined herein. Representative examples include, but are not limited to, methoxy, ethoxy, propoxy, butoxy, cyclohexyloxy, and the like.

"Alkyl" refers to a saturated, branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl, propan-2-yl, and cyclopropan-1-yl, butyls such as butan-1-yl, butan-2-yl, 2-methyl-propan-1-yl, 2-methyl-propan-2-yl, cyclobutan-1-yl, tert-butyl, and the like. The alkyl group may be substituted or unsubstituted; for example with one or more halogens, e.g., trifluoromethyl. In certain embodiments, an alkyl group comprises from 1 to 20 carbon atoms. Alternatively, an alkyl group may comprise from 1 to 3 carbon atoms, 3 to 6 carbon atoms, 6 to 9 carbon atoms, 9 to 12 carbon atoms, or 12 to 20 carbon atoms.

"Alkyl(aryl)" refers to an acyclic alkyl group in which one of the hydrogen atoms bonded to a carbon atom, typically a terminal or $sp^3$ carbon atom, is replaced with an aryl group. Typical alkyl(aryl) groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. In certain embodiments, an alkyl(aryl) group can be $(C_{6-20})$ alkyl(aryl) e.g., the alkyl group may be $(C_{1-10})$ and the aryl moiety may be $(C_{5-10})$.

"Alkoxy(aryl)" refers to an acyclic alkoxy group in which one of the hydrogen atoms bonded to a carbon atom, typically a terminal or $sp^3$ carbon atom, is replaced with an aryl group. Typical alkoxy(aryl) groups include, but are not limited to, benzyloxy, 2-phenylethanoxy and the like. In certain embodiments, an alkoxy(aryl) group can be $(C_{6-20})$ alkoxyl(aryl) e.g., the alkoxy group may be $(C_{1-10})$ and the aryl moiety may be $(C_{5-10})$.

"Alkynyl" refers to an unsaturated branched or straight-chain having at least one carbon-carbon triple bond derived by the removal of one hydrogen atom from a single carbon atom of a parent alkyne. Typical alkynyl groups include, but are not limited to, propynyl, butenyl, 2-pentynyl, 3-pentynyl, 2-hexynyl, 3-hexynyl and the like. The alkynyl group may be substituted or unsubstituted. In certain embodiments, an alkynyl group has from 3 to 20 carbon atoms. Alternatively, an alkynyl group may comprise from 2 to 5 carbon atoms, 5 to 9 carbon atoms, 9 to 12 carbon atoms, or 12 to 20 carbon atoms. Where the alkynyl group is attached to a nitrogen or other heteroatom, the first two carbons of the chain will be saturated, e.g., $N(CH_2)_2CH\equiv CCHR$.

"Aryl" refers to a monovalent aromatic hydrocarbon group derived by the removal of one hydrogen atom from a single carbon atom of a parent aromatic ring system. Aryl encompasses 5- and 6-membered carbocyclic aromatic rings, for example, benzene or cyclopentadiene; bicyclic ring systems wherein at least one ring is carbocyclic and aromatic, for example, naphthalene, indane; or two aromatic ring systems, for example benzyl phenyl, biphenyl, diphenylethane, diphenylmethane. The aryl group may be substituted or unsubstituted, for example with a halogen. The aryl group may be mono-, di- or tri-substituted.

"Concurrently" as used herein means sufficiently close in time to produce a combined effect (that is, concurrently may be simultaneously, or it may be two or more events occurring sequentially in time, typically within a short time period before or after each other). Thus active agents or compounds may be administered before, simultaneously with, or after said oligonucleotide, so long as the intended effect on the oligonucleotide activity or delivery is achieved.

"Cycloalkoxy" refers to a saturated or unsaturated cyclic alkyl group containing one or more oxygen atoms in the ring. Typical cycloalkoxy groups include, but are not limited to, groups derived from cyclopropane, cyclobutane, cyclopentane, cyclohexane, and the like such as dioxolane, oxetane, oxirane, tetrahydrofuran. The cycloalkoxy group may be substituted or unsubstituted. In certain embodiments, the cycloalkyl group can be $C_{2-10}$ cycloalkoxy, such as, for example, $C_4$ cycloalkoxy.

"Cycloalkyl" refers to a saturated or unsaturated cyclic alkyl group. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane, and the like. The cycloalkyl group may be substituted or unsubstituted. In certain embodiments, the cycloalkyl group can be $C_{3-10}$ cycloalkyl, such as, for example, $C_6$ cycloalkyl.

"Disease" refers to any disease, disorder, condition, symptom, or indication.

"Enhance the activity" as used herein refers to, for example, any administration of a intracellular trafficking route modulator effective to increase the activity of an antisense oligonucleotide (ASO) that acts on pre-mRNA via RNase H in the nucleus, on a siRNA that acts via the RISC complex in the cytosol, and/or (for SSOs) increase the alteration of pre-mRNA splicing, as reflected by an increase in the desired splice variant (which can be measured by any suitable technique, such as by a reporter gene readout; amelioration or treatment of symptoms in a subject, etc.), or (for antisense oligonucleotides) reduced levels of the corresponding target mRNA and/or protein, or of an siRNA (which can be measured by any suitable technique, such by flow cytometry for protein levels, treatment or amelioration of symptoms in a subject, etc.) (e.g., as compared to that found without concurrent administration of the active agents described herein).

"Enhance the delivery" as used herein refers to any administration of a intracellular trafficking route modulator effective to increase the cytosolic and/or nuclear concentration, accumulation, and/or half-life of the oligonucleotide (e.g., as compared to that found without concurrent administration of the active agents described herein)

"Halogen" refers to a fluoro, chloro, bromo, or iodo group.

"Heteroaryl" refers to a monovalent heteroaromatic group derived by the removal of one hydrogen atom from a single atom of a parent heteroaromatic ring system. Heteroaryl encompasses: 5- to 7-membered aromatic, monocyclic rings containing one or more, for example, from 1 to 4, or in certain embodiments, from 1 to 3, heteroatoms chosen from N, O, and S, with the remaining ring atoms being carbon; and polycyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. The heteroaryl group may be substituted or unsubstituted.

For example, heteroaryl includes a 5- to 7-membered heteroaromatic ring fused to a 5- to 7-membered cycloalkyl ring and a 5- to 7-membered heteroaromatic ring fused to a saturated 5- to 7-membered heterocycle. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, the S and O heteroatoms are not adjacent to one another. In certain embodiments, the total number of S and O atoms in the heteroaryl group is not more than 2. In certain embodiments, the total number of S and O atoms in the aromatic heterocycle is not more than 1. Typical heteroaryl groups include, but are not limited to, groups derived from acridine, arsindole, benzodioxin, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, piperidine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, the heteroaryl group can be between 5 to 20 membered heteroaryl, such as, for example, a 5 to 10 membered heteroaryl. In certain embodiments, heteroaryl groups can be those derived from thiophene, pyrrole, benzothiophene, benzofuran, indole, pyridine, quinoline, imidazole, oxazole, and pyrazine.

"Heterocycloalkyl" refers to a non-aromatic monocyclic ring or fused non-aromatic polycyclic rings with one or more heteroatom(s) independently selected from N, S and O, with the remaining ring atoms being carbon and wherein at least one heteroatom is present in each non-aromatic ring. The heterocycle group may be a three-member ring, a four member ring, a five member ring, a six member ring or a seven member ring. In certain embodiments, the heterocycloalkyl group is 1,4-dioxane, 1,3-dioxolane, 1,4-dithiane, imidazolidine, morpholine, piperidine, piperidone, piperazine, pyrolidone, pyrrolidine, or 1,3,5-trithiane. It may contain an imide. The heterocycloalkyl group may be bicyclic such as an heterospiro compound, e.g., heterospiro [3.3] heptanyl, heterospiro [3.4] octanyl, or heterospiro [5.5] undecanyl. The heterocycloalkyl group may be substituted or unsubstituted. Thus, heterocycloalkyl group encompasses heterocycloalkyl groups substituted with one or more halogens. In addition, the heterocycloalkyl group may be substituted with a $C_1$-$C_4$ alkyl or $C_1$-$C_4$ halo alkyl group such as a —$CF_3$ group.

"Oligonucleotide" or "Oligo" herein refers to polymers of deoxyribonucleotides or ribonucleotides in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid. Examples of such analogs include, without limitation, phosphorothioates, phosphoramidates, methyl phosphonates, chiral-methyl phosphonates, 2-O-methyl ribonucleotides, peptide-nucleic acids (PNAs). The phosporamidate analog may be a phosphorodiamidate morpholino oligomer (PMO) or a peptide-conjugated PMO (PPMO). The oligonucleotide may be of any suitable length, e.g., from 2, 3, 4, 5, 6, 8 or 10 nucleotides in length, up to 50, 60, 80, 100, 150 or 200 nucleotides in length, or more. Suitable oligonucleotides include, but are not limited to, short hairpin RNA (shRNA), microRNAs, antisense oligonucleotides (including splice switching oligonucleotides or "SSOs"), small double stranded interference RNA (siRNA)s, and ribozymes. Antisense oligonucleotides are known. Examples include, but are not limited to, those described in U.S. Pat. Nos. 8,067,571; 7,910,563; 7,563,778; 7,393,951; 7,307,069; 6,972,171; 6,417,169; 6,339,071; 6,312,900; 6,277,832; 5,985,558; and many others.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient," "pharmaceutically acceptable carrier," or "pharmaceutically acceptable adjuvant" refer, respectively, to an excipient, carrier or adjuvant with which at least one compound of the present disclosure is administered. "Pharmaceutically acceptable vehicle" refers to any of a diluent, adjuvant, excipient or carrier with which at least one compound of the present disclosure is administered.

"Splice switching oligonucleotides" (or "SSOs") are known and described in, for example, U.S. Pat. Nos. 8,067,569; 7,888,012; 7,884,194; 7,785,834; 6,727,355; 6,653,467; 6,653,466; and 5,976,879, and in US Patent Application No. 20100130591 to Sazani and Kole (May 27, 2010), the disclosures of all of which are incorporated by reference herein in their entirety. See also J. Bauman et al., *Oligonucleotides* 19, 1-14 (2009); P. Sazani and R. Kole, *J. Clin. Invest* 12, 481-486 (2003).

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereoisomers."

"Subjects" with which the present disclosure is concerned are primarily human subjects, but may also be carried out on animal subjects, particularly mammalian subjects such as dogs, cats, livestock and horses for veterinary purposes. While subjects may be of any suitable age, the subjects are in some embodiments neonatal, infant, juvenile, adolescent, adult, or geriatric subjects.

"Substituted" refers to a group in which one or more hydrogen atoms are each independently replaced with the same or different substituent(s). Typical substituents include, but are not limited to, $CO_2H$, halogen (e.g., chloro, fluoro), hydroxyl, $-N_3$, $-NH_2$, $-SO_{(1-3)}H$, or $-SH$.

"Therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^3H$ or $^{14}C$ are incorporated, are useful in drug and/or substrate tissue distribution studies. Tritiated and carbon-14, i.e., $^{14}C$, isotopes are particularly preferred for their ease of preparation and detectability. Substitution with positron emitting isotopes, such as $^{11}C$, $^{18}F$, $^{15}O$ and $^{13}N$, can be useful in Positron Emission Topography (PET) studies.

Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents. In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art.

Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4$/$D_2O$. Alternatively, deuterium may be also incorporated into a compound using methods such as through reduction such as using $LiAlD_4$ or $NaBD_3$, catalytic hydrogenation or acidic or basic isotopic exchange using appropriate deuterated reagents such as deuterides, $D_2$ and $D_2O$. In addition to the above, PCT publications, WO2014/169280; WO2015/058067; U.S. Pat. Nos. 8,354,557; 8,704,001 and US Patent Application Publication Nos.; 2010/0331540; 2014/0081019; 2014/0341994; 2015/0299166, the methods are hereby incorporated by reference.

Throughout the present specification, the terms "about" and/or "approximately" may be used in conjunction with numerical values and/or ranges. The term "about" is understood to mean those values near to a recited value. For example, "about 40 [units]" may mean within ±25% of 40

(e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or there below. Alternatively, depending on the context, the term "about" may mean±one half a standard deviation, ±one standard deviation, or ±two standard deviations. Furthermore, the phrases "less than about [a value]" or "greater than about [a value]" should be understood in view of the definition of the term "about" provided herein. The terms "about" and "approximately" may be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

As used herein, the verb "comprise" as used in this description and in the claims and its conjugations are used in its non-limiting sense to mean that items following the word are included, but items not specifically mentioned are not excluded.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Unless defined otherwise, all technical and scientific terms used herein have the same meanings as commonly understood by one of ordinary skill in the art to which this disclosure belongs. Preferred methods, devices, and materials are described, although any methods and materials similar or equivalent to those described herein can be used in the practice or testing of the present disclosure. All references cited herein are incorporated by reference in their entirety.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Unless defined otherwise, all technical and scientific terms used herein have the same meanings as commonly understood by one of ordinary skill in the art to which this disclosure belongs. Preferred methods, devices, and materials are described, although any methods and materials similar or equivalent to those described herein can be used in the practice or testing of the present disclosure. All references cited herein are incorporated by reference in their entirety.

The following Examples further illustrate the disclosure and are not intended to limit the scope. In particular, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

5.2. Active Agents

Active agents of the present disclosure are, in general, compounds of Formula I:

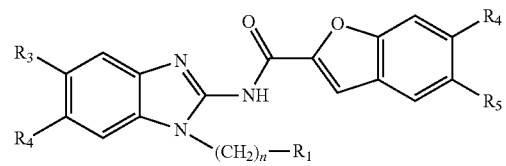

wherein $R_1$ is —$NR_6R_7$, an N-containing heterocycle or an N-containing heterocycloalkyl; $R_2$-$R_8$ are independently $C_{1-8}$ alkyl, $C_{1-8}$ alkoxy, $C_{2-8}$ alkenyl, $C_{3-8}$ alkynyl, $C_{3-8}$ cycloalkyl, H or halogen; $R_6$ and $R_7$ are independently $C_{1-8}$ alkyl or $R_6$ and $R_7$ together make a 4-8-member ring which may be substituted with one or more nitrogens; n is an integer between 1 and 8; and or a pharmaceutically acceptable salt thereof.

Compounds as described above can be made in accordance with known techniques or variations thereof that will be apparent to those skilled in the art in light of the teachings set forth in PCT Application WO 2016/003816, the disclosures of which are incorporated by reference herein in their entirety.

The active agents described herein can be used alone or in combination with other compounds that enhance the activity of oligonucleotides, examples of which include but are not limited to the intracellular trafficking inhibitors and retro compounds described in R. Juliano et al., Small Molecules that Enhance the Activity of Oligonucleotides, PCT Application WO 2013/123217 (22 Aug. 2013).

5.3. Oligonucleotide Compounds

Any suitable oligonucleotide may be employed, including but not limited to those described in U.S. Pat. No. 7,674,778, the disclosure of which is incorporated by reference herein in its entirety.

The oligonucleotide may include chemical modifications. Specific oligonucleotide chemical modifications are described below. It is not necessary for all positions in a given compound to be uniformly modified, and in fact more than one of the following modifications may be incorporated in a single siRNA compound or even in a single nucleotide thereof. The oligonucleotide may optionally be conjugated to a ligand by any suitable technique, including, but not limited to, those described in PCT Applications WO2011/126937 to Juliano et al. and WO2009/045536 to Juliano et al.

Some modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylpho sphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included. Representative United States Patents that teach the preparation of the above phosphorus atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference. In one embodiment, modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other oligonucleotide mimetics, both the sugar and the internucleoside linkage, i.e., the backbone, of the nucleoside units are replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497.

The active compounds disclosed herein can, as noted above, be prepared in the form of their salts, including pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

5.4. Compositions

The invention pertains to uses of the above-described active agents (including both active compounds and oligonucleotides) for methods and treatments as described below. Accordingly, the modulators of the present invention can be incorporated into pharmaceutical compositions suitable for administration. See, e.g., U.S. Pat. No. 7,459,547. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. Although compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 (i.e., the concentration of the test compound which achieves a half-maximal response) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

5.5. Methods of Use

As noted above, the present invention provides a method of introducing an oligonucleotide of interest into a cell, comprising (a) contacting an oligonucleotide compound as described above to the cell in an amount effective to introduce said oligonucleotide into said cell, (b) concurrently with (that is, before, after, or simultaneously with) contacting an active agent to the cell in an amount effective to enhance the activity of said oligonucleotide in said cell. The method may be carried out in vitro or in vivo with any type of cell, particularly animal cells. Animal cells may be mammalian cells, such as human, monkey, cat, dog, rat, mouse, or rabbit cells. The methods may be utilized for any purpose in which it is desired to introduce an oligonucleotide into a cell, including but not limited to those oligonucleotides (including polynucleotides and RNAi agents) for those purposes described in U.S. Pat. Nos. 7,682,626; 7,674,778; 7,473,419; 7,459,547; and 7,015,040, the disclosures of which are incorporated by reference herein in their entirety.

In some embodiments, the oligonucleotides are splice switching oligonucleotides (SSOs). Examples of suitable SSOs include, but are not limited to, those described in: Kole R, Krainer A R, Altman S., *RNA therapeutics: beyond RNA interference and antisense oligonucleotides*, Nat Rev Drug Discov. 11(2): 125-40 (Jan. 20, 2012); S. Cirak et al., *Exon skipping and dystrophin restoration in patients with Duchenne muscular dystrophy after systemic phosphorodiamidate morpholino oligomer treatment: an open-label, phase 2, dose-escalation study*, Lancet 378(9791):595-605 (Aug. 13, 2011); and NM Goemans et al., *Systemic administration of PRO051 in Duchenne's muscular dystrophy* N Engl J Med, 364, 1513-1522 (2011).

Non-limiting examples of phosphorodiamidate morpholino oligomers (PMOs), or peptide-conjugated PMOs (PPMOs) are found in FIG. 2 of Kole et al. 2012.

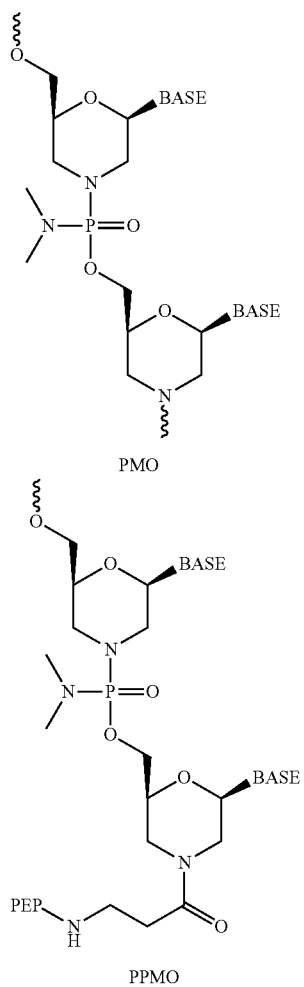

In particular embodiments, the oligonucleotide is eteplirsen or drisapersen, administered to the subject for the treatment of Duchenne muscular dystrophy. See, e.g., J. Mendell et al., *Ann. Neurol.* 74, 637-647 (2013); K. Flanigan et al., *Neuromuscular Disorders* 24, 16-24 (2014).

In some embodiments, the invention may be used to deliver the oligonucleotides for silencing (in whole or part) the genes described in U.S. Pat. No. 7,674,778, the disclosure of which is incorporated by reference herein in its entirety.

In some embodiments, the invention relates to a method of treating a subject at risk for or afflicted with unwanted cell proliferation, e.g., malignant or nonmalignant cell proliferation. The method comprises providing a ligand-conjugated oligonucleotide agent, wherein the oligonucleotide is homologous to and can silence, e.g., by cleavage, a gene which promotes unwanted cell proliferation; and administering a therapeutically effective dose of the ligand-conjugated oligonucleotide agent to a subject, preferably a human subject.

In an embodiment the gene is a growth factor or growth factor receptor gene, a kinase, e.g., a protein tyrosine, serine or threonine kinase gene, an adaptor protein gene, a gene encoding a G protein superfamily molecule, or a gene encoding a transcription factor.

In an embodiment the oligonucleotide agent silences the PDGF beta gene, and thus can be used to treat a subject having or at risk for a disorder characterized by unwanted PDGF beta expression, e.g., testicular and lung cancers.

In an embodiment the oligonucleotide agent silences the Erb-B gene, and thus can be used to treat a subject having or at risk for a disorder characterized by unwanted Erb-B expression, e.g., breast cancer.

In an embodiment the oligonucleotide agent silences the Src gene, and thus can be used to treat a subject having or at risk for a disorder characterized by unwanted Src expression, e.g., colon cancers.

In an embodiment the oligonucleotide agent silences the CRK gene, and thus can be used to treat a subject having or at risk for a disorder characterized by unwanted CRK expression, e.g., colon and lung cancers.

In an embodiment the oligonucleotide agent silences the GRB2 gene, and thus can be used to treat a subject having or at risk for a disorder characterized by unwanted GRB2 expression, e.g., squamous cell carcinoma.

In an embodiment the oligonucleotide agent silences the RAS gene, and thus can be used to treat a subject having or at risk for a disorder characterized by unwanted RAS expression, e.g., pancreatic, colon and lung cancers, and chronic leukemia.

In an embodiment the oligonucleotide agent silences the MEKK gene, and thus can be used to treat a subject having or at risk for a disorder characterized by unwanted MEKK expression, e.g., squamous cell carcinoma, melanoma or leukemia.

In an embodiment the oligonucleotide agent silences the JNK gene, and thus can be used to treat a subject having or at risk for a disorder characterized by unwanted JNK expression; e.g., pancreatic or breast cancers.

In an embodiment the oligonucleotide agent silences the RAF gene, and thus can be used to treat a subject having or at risk for a disorder characterized by unwanted RAF expression, e.g., lung cancer or leukemia.

In an embodiment the oligonucleotide agent silences the Erk1/2 gene, and thus can be used to treat a subject having or at risk for a disorder characterized by unwanted Erk1/2 expression, e.g., lung cancer.

In an embodiment the oligonucleotide agent silences the PCNA(p21) gene, and thus can be used to treat a subject having or at risk for a disorder characterized by unwanted PCNA expression, e.g., lung cancer.

In an embodiment the oligonucleotide agent silences the MYB gene, and thus can be used to treat a subject having or at risk for a disorder characterized by unwanted MYB expression, e.g., colon cancer or chronic myelogenous leukemia.

In an embodiment the oligonucleotide agent silences the c-MYC gene, and thus can be used to treat a subject having or at risk for a disorder characterized by unwanted c-MYC expression, e.g., Burkitt's lymphoma or neuroblastoma.

In an embodiment the oligonucleotide agent silences the JUN gene, and thus can be used to treat a subject having or at risk for a disorder characterized by unwanted JUN expression, e.g., ovarian, prostate or breast cancers.

In an embodiment the oligonucleotide agent silences the FOS gene, and thus can be used to treat a subject having or at risk for a disorder characterized by unwanted FOS expression, e.g., skin or prostate cancers.

In an embodiment the oligonucleotide agent silences the BCL-2 gene, and thus can be used to treat a subject having or at risk for a disorder characterized by unwanted BCL-2 expression, e.g., lung or prostate cancers or Non-Hodgkin lymphoma.

In an embodiment the oligonucleotide agent silences the Cyclin D gene, and thus can be used to treat a subject having or at risk for a disorder characterized by unwanted Cyclin D expression, e.g., esophageal and colon cancers.

In an embodiment the oligonucleotide agent silences the VEGF gene, and thus can be used to treat a subject having or at risk for a disorder characterized by unwanted VEGF expression, e.g., esophageal and colon cancers.

In an embodiment the oligonucleotide agent silences the EGFR gene, and thus can be used to treat a subject having or at risk for a disorder characterized by unwanted EGFR expression, e.g., breast cancer.

In an embodiment the oligonucleotide agent silences the Cyclin A gene, and thus can be used to treat a subject having or at risk for a disorder characterized by unwanted Cyclin A expression, e.g., lung and cervical cancers.

In an embodiment the oligonucleotide agent silences the Cyclin E gene, and thus can be used to treat a subject having or at risk for a disorder characterized by unwanted Cyclin E expression, e.g., lung and breast cancers.

In an embodiment the oligonucleotide agent silences the WNT-1 gene, and thus can be used to treat a subject having or at risk for a disorder characterized by unwanted WNT-1 expression, e.g., basal cell carcinoma.

In an embodiment the oligonucleotide agent silences the beta-catenin gene, and thus can be used to treat a subject having or at risk for a disorder characterized by unwanted beta-catenin expression, e.g., adenocarcinoma or hepatocellular carcinoma.

In an embodiment the oligonucleotide agent silences the c-MET gene, and thus can be used to treat a subject having or at risk for a disorder characterized by unwanted c-MET expression, e.g., hepatocellular carcinoma.

In an embodiment the oligonucleotide agent silences the PKC gene, and thus can be used to treat a subject having or at risk for a disorder characterized by unwanted PKC expression, e.g., breast cancer.

In an embodiment the oligonucleotide agent silences the NFKB gene, and thus can be used to treat a subject having or at risk for a disorder characterized by unwanted NFKB expression, e.g., breast cancer.

In an embodiment the oligonucleotide agent silences the STAT3 gene, and thus can be used to treat a subject having or at risk for a disorder characterized by unwanted STAT3 expression, e.g., prostate cancer.

In an embodiment the oligonucleotide agent silences the survivin gene, and thus can be used to treat a subject having or at risk for a disorder characterized by unwanted survivin expression, e.g., cervical or pancreatic cancers.

In an embodiment the oligonucleotide agent silences the Her2/Neu gene, and thus can be used to treat a subject having or at risk for a disorder characterized by unwanted Her2/Neu expression, e.g., breast cancer.

In an embodiment the oligonucleotide agent silences the topoisomerase I gene, and thus can be used to treat a subject having or at risk for a disorder characterized by unwanted topoisomerase I expression, e.g., ovarian and colon cancers.

In an embodiment the oligonucleotide agent silences the topoisomerase II alpha gene, and thus can be used to treat a subject having or at risk for a disorder characterized by unwanted topoisomerase II expression, e.g., breast and colon cancers.

In an embodiment the oligonucleotide agent silences mutations in the p73 gene, and thus can be used to treat a subject having or at risk for a disorder characterized by unwanted p73 expression, e.g., colorectal adenocarcinoma.

In an embodiment the oligonucleotide agent silences mutations in the p21(WAF1/CIP1) gene, and thus can be used to treat a subject having or at risk for a disorder characterized by unwanted p21(WAF1/CIP1) expression, e.g., liver cancer.

In an embodiment the oligonucleotide agent silences mutations in the p27(KIP1) gene, and thus can be used to treat a subject having or at risk for a disorder characterized by unwanted p27(KIP1) expression, e.g., liver cancer.

In an embodiment the oligonucleotide agent silences mutations in the PPM1D gene, and thus can be used to treat a subject having or at risk for a disorder characterized by unwanted PPM1D expression, e.g., breast cancer.

In an embodiment the oligonucleotide agent silences mutations in the RAS gene, and thus can be used to treat a subject having or at risk for a disorder characterized by unwanted RAS expression, e.g., breast cancer.

In an embodiment the oligonucleotide agent silences mutations in the caveolin I gene, and thus can be used to treat a subject having or at risk for a disorder characterized by unwanted caveolin I expression, e.g., esophageal squamous cell carcinoma.

In an embodiment the oligonucleotide agent silences mutations in the MIB I gene, and thus can be used to treat a subject having or at risk for a disorder characterized by unwanted MIB I expression, e.g., male breast carcinoma (MBC).

In an embodiment the oligonucleotide agent silences mutations in the MTAI gene, and thus can be used to treat a subject having or at risk for a disorder characterized by unwanted MTAI expression, e.g., ovarian carcinoma.

In an embodiment the oligonucleotide agent silences mutations in the M68 gene, and thus can be used to treat a subject having or at risk for a disorder characterized by unwanted M68 expression, e.g., human adenocarcinomas of the esophagus, stomach, colon, and rectum.

In preferred embodiments the oligonucleotide agent silences mutations in tumor suppressor genes, and thus can be used as a method to promote apoptotic activity in combination with chemotherapeutics.

In an embodiment the oligonucleotide agent silences mutations in the p53 tumor suppressor-gene, and thus can be used to treat a subject having or at risk for a disorder characterized by unwanted p53 expression, e.g., gall bladder, pancreatic and lung cancers.

In an embodiment the oligonucleotide agent silences mutations in the p53 family member DN-p63, and thus can be used to treat a subject having or at risk for a disorder characterized by unwanted DN-p63 expression, e.g., squamous cell carcinoma.

In an embodiment the oligonucleotide agent silences mutations in the pRb tumor suppressor gene, and thus can be used to treat a subject having or at risk for a disorder characterized by unwanted pRb expression, e.g., oral squamous cell carcinoma.

In an embodiment the oligonucleotide agent silences mutations in the APC1 tumor suppressor gene, and thus can be used to treat a subject having or at risk for a disorder characterized by unwanted APC1 expression, e.g., colon cancer.

In an embodiment the oligonucleotide agent silences mutations in the BRCA1 tumor suppressor gene, and thus can be used to treat a subject having or at risk for a disorder characterized by unwanted BRCA1 expression, e.g., breast cancer.

In an embodiment the oligonucleotide agent silences mutations in the PTEN tumor suppressor gene, and thus can be used to treat a subject having or at risk for a disorder characterized by unwanted PTEN expression, e.g., hamartomas, gliomas, and prostate and endometrial cancers.

In an embodiment the oligonucleotide agent silences MLL fusion genes, e.g., MLL-AF9, and thus can be used to treat a subject having or at risk for a disorder characterized by unwanted MLL fusion gene expression, e.g., acute leukemias.

In an embodiment the oligonucleotide agent silences the BCR/ABL fusion gene, and thus can be used to treat a subject having or at risk for a disorder characterized by unwanted BCR/ABL fusion gene expression, e.g., acute and chronic leukemias.

In an embodiment the oligonucleotide agent silences the TEL/AML1 fusion gene, and thus can be used to treat a subject having or at risk for a disorder characterized by unwanted TEL/AML1 fusion gene expression, e.g., childhood acute leukemia.

In an embodiment the oligonucleotide agent silences the EWS/FLI1 fusion gene, and thus can be used to treat a subject having or at risk for a disorder characterized by unwanted EWS/FLI1 fusion gene expression, e.g., Ewing Sarcoma.

In an embodiment the oligonucleotide agent silences the TLS/FUS 1 fusion gene, and thus can be used to treat a subject having or at risk for a disorder characterized by unwanted TLS/FUS 1 fusion gene expression, e.g., Myxoid liposarcoma.

In an embodiment the oligonucleotide agent silences the PAX3/FKHR fusion gene, and thus can be used to treat a subject having or at risk for a disorder characterized by unwanted PAX3/FKHR fusion gene expression, e.g., Myxoid liposarcoma.

In an embodiment the oligonucleotide agent silences the AML1/ETO fusion gene, and thus can be used to treat a subject having or at risk for a disorder characterized by unwanted AML1/ETO fusion gene expression, e.g., acute leukemia.

Another aspect of the invention relates to a method of treating a subject, e.g., a human, at risk for or afflicted with a disease or disorder that may benefit by angiogenesis inhibition e.g., cancer. The method comprises providing a ligand-conjugated oligonucleotide agent, wherein said oligonucleotide agent is homologous to and can silence, e.g., by cleavage, a gene which mediates angiogenesis; and administering a therapeutically effective dosage of said ligand-conjugated oligonucleotide agent to a subject, preferably a human.

In an embodiment the oligonucleotide agent silences the alpha v-integrin gene, and thus can be used to treat a subject having or at risk for a disorder characterized by unwanted alpha V integrin, e.g., brain tumors or tumors of epithelial origin.

In an embodiment the oligonucleotide agent silences the Flt-1 receptor gene, and thus can be used to treat a subject having or at risk for a disorder characterized by unwanted Flt-1 receptors, e.g., cancer and rheumatoid arthritis.

In an embodiment the oligonucleotide agent silences the tubulin gene, and thus can be used to treat a subject having or at risk for a disorder characterized by unwanted tubulin, e.g., cancer and retinal neovascularization.

In an embodiment the oligonucleotide agent silences a SNARE gene (e.g., VAMP8) or genes encoding other regulatory proteins associated with the exocytosis of secretory granules of mucins or the exocytosis of secretory granules containing inflammation/allergy mediators"

Another aspect of the invention relates to a method of treating a subject infected with a virus or at risk for or afflicted with a disorder or disease associated with a viral infection. The method comprises providing a ligand-conjugated oligonucleotide agent, wherein said oligonucleotide agent is homologous to and can silence, e.g., by cleavage, a viral gene of a cellular gene which mediates viral function, e.g., entry or growth; and administering a therapeutically effective dose of said ligand-conjugated oligonucleotide agent to a subject, preferably a human subject.

Thus, the invention provides for a method of treating patients infected by the Human Papilloma Virus (HPV) or at risk for or afflicted with a disorder mediated by HPV, e.g., cervical cancer. HPV is linked to 95% of cervical carcinomas and thus an antiviral therapy is an attractive method to treat these cancers and other symptoms of viral infection.

In an embodiment, the expression of a HPV gene is reduced. In an embodiment, the HPV gene is one of the group of E2, E6, or E7.

In an embodiment the expression of a human gene that is required for HPV replication is reduced.

The invention also includes a method of treating patients infected by the Human Immunodeficiency Virus (HIV) or at risk for or afflicted with a disorder mediated by HIV, e.g., Acquired Immune Deficiency Syndrome (AIDS). In an embodiment, the expression of a HIV gene is reduced. In an embodiment, the HIV gene is CCR5, Gag, or Rev. In an embodiment the expression of a human gene that is required for HIV replication is reduced. In an embodiment, the gene is CD4 or Tsg101.

The invention also includes a method for treating patients infected by the Hepatitis B Virus (HBV) or at risk for or afflicted with a disorder mediated by HBV, e.g., cirrhosis and heptocellular carcinoma. In an embodiment, the expression of a HBV gene is reduced. In an embodiment, the targeted HBV gene encodes one of the group of the tail region of the HBV core protein, the pre-cregious (pre-c) region, or the cregious (c) region. In an embodiment, a targeted HBV-RNA sequence is comprised of the poly(A) tail.

In preferred embodiment the expression of a human gene that is required for HBV replication is reduced.

The invention also provides for a method of treating patients infected by the Hepatitis A Virus (HAV), or at risk for or afflicted with a disorder mediated by HAV. In an embodiment the expression of a human gene that is required for HAV replication is reduced.

The present invention provides for a method of treating patients infected by the Hepatitis C Virus (HCV), or at risk for or afflicted with a disorder mediated by HCV, e.g., cirrhosis. In an embodiment, the expression of a HCV gene is reduced. In an embodiment the expression of a human gene that is required for HCV replication is reduced.

The present invention also provides for a method of treating patients infected by the any of the group of Hepatitis Viral strains comprising hepatitis D, E, F, G, or H, or patients at risk for or afflicted with a disorder mediated by any of these strains of hepatitis. In an embodiment, the expression of a Hepatitis, D, E, F, G, or H gene is reduced. In an embodiment the expression of a human gene that is required for hepatitis D, E, F, G or H replication is reduced.

Methods of the invention also provide for treating patients infected by the Respiratory Syncytial Virus (RSV) or at risk for or afflicted with a disorder mediated by RSV, e.g., lower respiratory tract infection in infants and childhood asthma, pneumonia and other complications, e.g., in the elderly. In an embodiment, the expression of a RSV gene is reduced. In an embodiment, the targeted HBV gene encodes one of the group of genes N, L, or P. In an embodiment the expression of a human gene that is required for RSV replication is reduced.

Methods of the invention provide for treating patients infected by the Herpes Simplex Virus (HSV) or at risk for or afflicted with a disorder mediated by HSV, e.g., genital herpes and cold sores as well as life-threatening or sight-impairing disease mainly in immunocompromised patients. In an embodiment, the expression of a HSV gene is reduced. In an embodiment, the targeted HSV gene encodes DNA polymerase or the helicase-primase. In an embodiment the expression of a human gene that is required for HSV replication is reduced.

The invention also provides a method for treating patients infected by the herpes Cytomegalovirus (CMV) or at risk for or afflicted with a disorder mediated by CMV, e.g., congenital virus infections and morbidity in immunocompromised patients. In an embodiment, the expression of a CMV gene is reduced. In an embodiment the expression of a human gene that is required for CMV replication is reduced.

Methods of the invention also provide for a method of treating patients infected by the herpes Epstein Barr Virus (EBV) or at risk for or afflicted with a disorder mediated by EBV, e.g., NK/T-cell lymphoma, non-Hodgkin lymphoma, and Hodgkin disease. In an embodiment, the expression of a EBV gene is reduced. In an embodiment the expression of a human gene that is required for EBV replication is reduced.

Methods of the invention also provide for treating patients infected by Kaposi's Sarcoma-associated Herpes Virus (KSHV), also called human herpesvirus 8, or patients at risk for or afflicted with a disorder mediated by KSHV, e.g., Kaposi's sarcoma, multicentric Castleman's disease and AIDS-associated primary effusion lymphoma. In an embodiment, the expression of a KSHV gene is reduced. In an embodiment the expression of a human gene that is required for KSHV replication is reduced.

The invention also includes a method for treating patients infected by the JC Virus (JCV) or a disease or disorder associated with this virus, e.g., progressive multifocal leukoencephalopathy (PML). In an embodiment, the expression of a JCV gene is reduced. In preferred embodiment the expression of a human gene that is required for JCV replication is reduced.

Methods of the invention also provide for treating patients infected by the myxovirus or at risk for or afflicted with a disorder mediated by myxovirus, e.g., influenza. In an embodiment, the expression of a myxovirus gene is reduced. In an embodiment the expression of a human gene that is required for myxovirus replication is reduced.

Methods of the invention also provide for treating patients infected by the rhinovirus or at risk for of afflicted with a disorder mediated by rhinovirus, e.g., the common cold. In an embodiment, the expression of a rhinovirus gene is reduced. In preferred embodiment the expression of a human gene that is required for rhinovirus replication is reduced.

Methods of the invention also provide for treating patients infected by the coronavirus or at risk for of afflicted with a disorder mediated by coronavirus, e.g., the common cold. In an embodiment, the expression of a coronavirus gene is reduced. In preferred embodiment the expression of a human gene that is required for coronavirus replication is reduced.

Methods of the invention also provide for treating patients infected by the flavivirus West Nile or at risk for or afflicted with a disorder mediated by West Nile Virus. In an embodiment, the expression of a West Nile Virus gene is reduced. In an embodiment, the West Nile Virus gene is one of the group comprising E, NS3, or NS5. In an embodiment the expression of a human gene that is required for West Nile Virus replication is reduced.

Methods of the invention also provide for treating patients infected by the St. Louis Encephalitis flavivirus, or at risk for or afflicted with a disease or disorder associated with this virus, e.g., viral hemorrhagic fever or neurological disease. In an embodiment, the expression of a St. Louis Encephalitis gene is reduced. In an embodiment the expression of a human gene that is required for St. Louis Encephalitis virus replication is reduced.

Methods of the invention also provide for treating patients infected by the Tick-borne encephalitis flavivirus, or at risk for or afflicted with a disorder mediated by Tick-borne encephalitis virus, e.g., viral hemorrhagic fever and neurological disease. In an embodiment, the expression of a Tick-borne encephalitis virus gene is reduced. In an embodiment the expression of a human gene that is required for Tick-borne encephalitis virus replication is reduced.

Methods of the invention also provide for methods of treating patients infected by the Murray Valley encephalitis flavivirus, which commonly results in viral hemorrhagic fever and neurological disease. In an embodiment, the expression of a Murray Valley encephalitis virus gene is reduced. In an embodiment the expression of a human gene that is required for Murray Valley encephalitis virus replication is reduced.

The invention also includes methods for treating patients infected by the dengue flavivirus, or a disease or disorder associated with this virus, e.g., dengue hemorrhagic fever. In an embodiment, the expression of a dengue virus gene is reduced. In an embodiment the expression of a human gene that is required for dengue virus replication is reduced.

Methods of the invention also provide for treating patients infected by the Simian Virus 40 (SV40) or at risk for or afflicted with a disorder mediated by SV40, e.g., tumorigenesis. In an embodiment, the expression of a SV40 gene is reduced. In an embodiment the expression of a human gene that is required for SV40 replication is reduced.

The invention also includes methods for treating patients infected by the Human T Cell Lymphotropic Virus (HTLV), or a disease or disorder associated with this virus, e.g., leukemia and myelopathy. In an embodiment, the expression of a HTLV gene is reduced. In an embodiment the HTLV1 gene is the Tax transcriptional activator. In an embodiment the expression of a human gene that is required for HTLV replication is reduced.

Methods of the invention also provide for treating patients infected by the Moloney-Murine Leukemia Virus (Mo-MuLV) or at risk for or afflicted with a disorder mediated by Mo-MuLV, e.g., T-cell leukemia. In an embodiment, the expression of a Mo-MuLV gene is reduced. In an embodiment the expression of a human gene that is required for Mo-MuLV replication is reduced.

Methods of the invention also provide for treating patients infected by the encephalomyocarditis virus (EMCV) or at risk for or afflicted with a disorder mediated by EMCV, e.g., myocarditis. EMCV leads to myocarditis in mice and pigs and is capable of infecting human myocardial cells. This virus is therefore a concern for patients undergoing xenotransplantation. In an embodiment, the expression of a EMCV gene is reduced. In an embodiment the expression of a human gene that is required for EMCV replication is reduced.

The invention also includes a method for treating patients infected by the measles virus (MV) or at risk for or afflicted with a disorder mediated by MV, e.g., measles. In an embodiment, the expression of a MV gene is reduced. In an embodiment the expression of a human gene that is required for MV replication is reduced.

The invention also includes a method for treating patients infected by the Vericella zoster virus (VZV) or at risk for or afflicted with a disorder mediated by VZV, e.g., chicken pox or shingles (also called zoster). In an embodiment, the expression of a VZV gene is reduced. In an embodiment the expression of a human gene that is required for VZV replication is reduced.

The invention also includes a method for treating patients infected by an adenovirus or at risk for or afflicted with a disorder mediated by an adenovirus, e.g., respiratory tract infection. In an embodiment, the expression of an adenovirus gene is reduced. In an embodiment the expression of a human gene that is required for adenovirus replication is reduced.

The invention includes a method for treating patients infected by a yellow fever virus (YFV) or at risk for or afflicted with a disorder mediated by a YFV, e.g., respiratory tract infection. In an embodiment, the expression of a YFV gene is reduced. In an embodiment, the preferred gene is one of a group that includes the E, NS2A, or NS3 genes. In an embodiment the expression of a human gene that is required for YFV replication is reduced.

Methods of the invention also provide for treating patients infected by the poliovirus or at risk for or afflicted with a disorder mediated by poliovirus, e.g., polio. In an embodiment, the expression of a poliovirus gene is reduced. In an embodiment the expression of a human gene that is required for poliovirus replication is reduced.

Methods of the invention also provide for treating patients infected by a poxvirus or at risk for or afflicted with a disorder mediated by a poxvirus, e.g., smallpox. In an embodiment, the expression of a poxvirus gene is reduced. In an embodiment the expression of a human gene that is required for poxvirus replication is reduced.

In another aspect the invention features methods of treating a subject infected with a pathogen, e.g., a bacterial, amoebic, parasitic, or fungal pathogen. The method comprises providing a ligand-conjugated oligonucleotide agent, wherein said oligonucleotide is homologous to and can silence, e.g., by cleavage of a pathogen gene; and administering a therapeutically effective dose of said ligand-conjugated oligonucleotide agent to a subject, preferably a human subject.

The target gene can be one involved in growth, cell wall synthesis, protein synthesis, transcription, energy metabolism, e.g., the Krebs cycle, or toxin production. Thus, the present invention provides for a method of treating patients infected by a *plasmodium* that causes malaria. In an embodiment, the expression of a *plasmodium* gene is reduced. In an embodiment, the gene is apical membrane antigen 1 (AMA1). In an embodiment the expression of a human gene that is required for *plasmodium* replication is reduced.

The invention also includes methods for treating patients infected by the *Mycobacterium ulcerans*, or a disease or disorder associated with this pathogen, e.g., Buruli ulcers. In an embodiment, the expression of a *Mycobacterium ulcerans* gene is reduced. In an embodiment the expression of a human gene that is required for *Mycobacterium ulcerans* replication is reduced.

The invention also includes methods for treating patients infected by the *Mycobacterium tuberculosis*, or a disease or disorder associated with this pathogen, e.g., tuberculosis. In an embodiment, the expression of a *Mycobacterium tuberculosis* gene is reduced. In an embodiment the expression of a human gene that is required for *Mycobacterium* tuberculos is replication is reduced.

The invention also includes methods for treating patients infected by the *Mycobacterium leprae*, or a disease or disorder associated with this pathogen, e.g., leprosy. In an embodiment, the expression of a *Mycobacterium leprae* gene is reduced. In an embodiment the expression of a human gene that is required for *Mycobacterium leprae* replication is reduced.

The invention also includes methods for treating patients infected by the bacteria *Staphylococcus aureus*, or a disease or disorder associated with this pathogen, e.g., infections of the skin and mucous membranes. In an embodiment, the expression of a *Staphylococcus aureus* gene is reduced. In an embodiment the expression of a human gene that is required for *Staphylococcus aureus* replication is reduced.

The invention also includes methods for treating patients infected by the bacteria *Streptococcus pneumoniae*, or a disease or disorder associated with this pathogen, e.g., pneumonia or childhood lower respiratory tract infection. In an embodiment, the expression of a *Streptococcus pneumoniae* gene is reduced. In an embodiment the expression of a human gene that is required for *Streptococcus pneumoniae* replication is reduced.

The invention also includes methods for treating patients infected by the bacteria *Streptococcus pyogenes*, or a disease or disorder associated with this pathogen, e.g., Strep throat or Scarlet fever. In an embodiment, the expression of a *Streptococcus pyogenes* gene is reduced. In an embodiment the expression of a human gene that is required for *Streptococcus pyogenes* replication is reduced.

The invention also includes methods for treating patients infected by the bacteria *Chlamydia pneumoniae*, or a disease or disorder associated with this pathogen, e.g., pneumonia or childhood lower respiratory tract infection. In an embodiment, the expression of a *Chlamydia pneumoniae* gene is reduced. In an embodiment the expression of a human gene that is required for *Chlamydia pneumoniae* replication is reduced.

The invention also includes methods for treating patients infected by the bacteria *Mycoplasma pneumoniae*, or a disease or disorder associated with this pathogen, e.g., pneumonia or childhood lower respiratory tract infection. In an embodiment, the expression of a *Mycoplasma pneumoniae* gene is reduced. In an embodiment the expression of a human gene that is required for *Mycoplasma pneumoniae* replication is reduced.

Another aspect of the invention relates to a method of treating a subject, e.g., a human, at risk for or afflicted with a disease or disorder characterized by an unwanted immune response, e.g., an inflammatory disease or disorder, or an autoimmune disease or disorder. The method comprises providing a ligand-conjugated oligonucleotide agent, wherein said oligonucleotide agent is homologous to and can silence, e.g., by cleavage, a gene which mediates an unwanted immune response; and administering said ligand-conjugated oligonucleotide agent to a subject, preferably a human subject. In an embodiment the disease or disorder is an ischemia or reperfusion injury, e.g., ischemia or reperfusion injury associated with acute myocardial infarction, unstable angina, cardiopulmonary bypass, surgical intervention e.g., angioplasty, e.g., percutaneous transluminal coronary angioplasty, the response to a transplanted organ or tissue, e.g., transplanted cardiac or vascular tissue; or thrombolysis. In an embodiment the disease or disorder is restenosis, e.g., restenosis associated with surgical intervention e.g., angioplasty, e.g., percutaneous transluminal coronary angioplasty. In a preferred embodiment the disease or disorder is Inflammatory Bowel Disease, e.g., Crohn Disease or Ulcerative Colitis. In a preferred embodiment the disease or disorder is inflammation associated with an infection or injury. In a preferred embodiment the disease or disorder is asthma, lupus, multiple sclerosis, diabetes, e.g., type II diabetes, arthritis, e.g., rheumatoid or psoriatic. In particularly preferred embodiments the oligonucleotide agent silences an integrin or co-ligand thereof, e.g., VLA4, VCAM, ICAM. In particularly preferred embodiments the oligonucleotide agent silences a selectin or co-ligand thereof, e.g., P-selectin, E-selectin (ELAM), I-selectin, P-selectin glycoprotein-1 (PSGL-1). In particularly preferred embodiments the oligonucleotide agent silences a component of the complement system, e.g., C3, C5, C3aR, C5aR, C3 convertase, C5 convertase.

In particularly preferred embodiments the oligonucleotide agent silences a chemokine or receptor thereof, e.g., TNFI, TNFJ, IL-1a, IL-1b, IL-1 I, IL-1J, IL-2, IL-2R, IL-4, IL-4R, IL-5, IL-6, IL-8, IL-13, TNFRI, TNFRII, IgE, SCYA11, CCR3.

In other embodiments the oligonucleotide agent silences GCSF, Gro1, Gro2, Gro3, PF4, MIG, Pro-Platelet Basic Protein (PPBP), MIP-1I, MIP-1J, RANTES, MCP-1, MCP-2, MCP-3, CMBKR1, CMBKR2, CMBKR3, CMBKR5, AIF-1, I-309.

Another aspect of the invention features, a method of treating a subject, e.g., a human, at risk for or afflicted with an acute or a chronic lung (or systemic) disorder such as cystic fibrosis (CF), asthma, chronic obstructive pulmonary disease (COPD), primary ciliary dyskinesia (PCD). In the case of CF, the method may involve a SSO targeting 3849+10 kbC→T. Alternatively, the invention includes SSO targeting other CF-causing CFTR splicing mutations; other methods involve CF and other lung diseases that could benefit from oligonucleotide-based therapies (oligonucleotides may be SSOs, ASO, etc).

The Cystic Fibrosis Mutation Data Base maintained at the Hospital for Sick Children in Toronto, reports that splicing accounts for 11.2% of all CFTR mutations. The details about the pathophysiological importance of many of these mutations are limited. For example—here are some splicing mutations nearby (in introns 21-23) to 3849+10 kb C-T (see the Example section). Note: the old terminology is used herein.

TABLE 1

Examples of CFTR mutations associated with splicing

| New terminology | Old terminology | | | |
|---|---|---|---|---|
| c.3468 + 5G > A | 3600 + 5G –> A | intron 21 | G to A at 3600 + 5 | mRNA splicing defect? |
| c.3468 + 2 3468 + 3insT | 3600 + 2insT | intron 21 | insertion of T after 3600 + 2 | mRNA splicing defect? |
| c.3468G > A | 3600G –> A | exon 21 | G to A at 3600 | mRNA splicing defect |
| c.3469 – 2A > G | 3601 – 2A –> G | intron 21 | A to G at 3601 – 2 | mRNA splicing defect |
| c.3469 – 17T > C | 3601 – 17T –> C | intron 21 | T to C at 3601 – 17 | mRNA splicing defect? |
| c.3469 – 20T > C | 3601 – 20T –> C | intron 21 | T to C at 3601 – 20 | mRNA splicing mutant? |
| c.3717 + 12191C > T | 3849 + 10kbC –> T | intron 22 | C toTina 6.2 kb EcoRI fragment 10 kb from 19 | creation of splice acceptor site |
| c.3717 + 45G > A | 3849 + 45G –> A | intron 22 | G to A at 3849 + 45 | Splicing |
| c.3717 + 40A > G | 3849 + 40A –> G | intron 22 | A to G at 3849 + 40 | Splicing |
| c.3717 + 5G > A | 3849 + 5G –> A | intron 22 | G to A at 3849 + 5 | mRNA splicing defect? |
| c.3717 + 4A > G | 3849 + 4A –> G | intron 22 | A to G at 3849 + 4 | mRNA splicing defect? |
| c.3717 + 1G > A | 3849 + 1G –> A | intron 22 | G to A at 3849 + 1 | mRNA splicing defect |
| c.3717G > A | 3849G –> A | exon 22 | G to A at 3849 | mRNA splicing defect? |
| c.3718 – 1G > A | 3850 – 1G –> A | intron 22 | G to A at 3850 – 1 | mRNA splicing defect |
| c.3718 – 3T > G | 3850 – 3T –> G | intron 22 | T to G at 3850 – 3 | mRNA splicing defect |
| c.3718 – 39a > G | | intron 22 | | |
| c.3873 + 33A > G | 4005 + 33A –> G | intron 23 | A to G at 4005 + 33 | Splicing |
| c.3873 + 29G > C | 4005 + 29G –> C | intron 23 | G to C at 4005 + 29 | Splicing |
| c.3873 + 3G > T | 4005 + 3G > T | intron 23 | 4005 + 3G > T | |
| c.3873 + 2T > C | 4005 + 2T –> C | intron 23 | T to C at 4005 + 2 | mRNA splicing defect |
| c.3873 + 1G > A | 4005 + 1G –> A | intron 23 | G to A at 4005 + 1 | mRNA splicing defect |

For treating or ameliorating the symptoms of CF one target is an ASO or siRNA to reduce the levels of the epithelial sodium channel (ENaC) may be used. ENaC plays a role in CF. Research is underway to find inhibitors of ENaC. See Martin et al. 2018 "Ion channels as targets to treat cystic fibrosis lung disease" J Cystic Fibrosis 17 S22-S2. Applicants methods using delivery directly to the lungs have advantages over existing and pre-clinical small molecule ENaC inhibitors which are administered systemically. The systemic inhibitors will also affect ENaC in the kidney with major side effects. Administration of antisense (ASO) or siRNA oligonucleotides via the airways and thus 'knock down' ENaC expression only in the lung. The oligo enhancing compounds disclosed herein like UNC2383 may improve effectiveness of airway-administered ASOs or siRNAs targeting ENaC.

In another embodiment, the oligonucleotide may be an antisense oligonucleotide or a modified miRNA that specifically targets miRNAs or mimics the activity of miRNA. More specifically, miR-9 (MicroRNA-9) is over expressed in CF cells and it down regulates the ANO1 chloride channel. See Sonneville et al. 2017 "MicroRNA-9 downregulates the ANO1 chloride channel and contributes to cystic fibrosis lung pathology" Nature Comm 8, 710 doi: 10.1038/s41467-017-00813-z. Hence an ASO targeting miR-9 in combination with the compounds disclosed herein, such as UNC2383, may be useful to treat or alleviate the symptoms of CF.

An ASO or siRNA targeting a mucin may be used to treat asthma, COPD or idiopathic pulmonary fibrosis (IPF). Airway mucin overexpression, particularly of MUC5AC or MUC5B, are postulated to play a role in cystic fibrosis, asthma, COPD and IPF. See Bronser and Erle, 2017 "Airway Mucus and Asthma: The Role of MUC5AC and MUC5B" J Clinical Medicine 6 112 doi:10.3390/jcm6120112 pp 1-17; and Kreda et al. Cold Spring Harb Perspect Med. 2012 Sep. 1; 2(9):a009589. doi: 10.1101/cshperspect.a009589. A therapeutic approach is to use siRNA or antisense (ASOs) to 'knock down' MUC5AC or MUC5B expression in airways. Studies suggest that for COPD, bronchial epithelial cells (HBEC) are central to the pathology and hence a therapy targeting HBEC. The oligo enhancing compounds like UNC2383 could potentially improve effects of airway-administered ASOs or siRNAs. Other diseases with pathogenic production of MUC5AC or MUC5B or when production of MUC5AC or MUC5B is associated with cancer.

Therapies either delivering miRNAs or oligonucleotides targeting miRNAs in combination with the small molecule compounds disclosed herein may be useful for treatments of disorders such as CF, asthma, COPD, IPF, lung cancer and other lung diseases.

Another aspect of the invention features, a method of treating a subject, e.g., a human, at risk for or afflicted with acute pain or chronic pain. The method comprises providing a ligand-conjugated oligonucleotide agent, wherein said ligand is an aromatic group and said oligonucleotide is homologous to and can silence, e.g., by cleavage, a gene which mediates the processing of pain; and administering a therapeutically effective dose of said ligand-conjugated oligonucleotide agent to a subject, preferably a human subject. In particularly preferred embodiments the oligonucleotide agent silences a component of an ion channel. In particularly preferred embodiments the oligonucleotide agent silences a neurotransmitter receptor or ligand.

Another aspect of the invention relates to a method of treating a subject, e.g., a human, at risk for or afflicted with a neurological disease or disorder. The method comprises providing a ligand-conjugated oligonucleotide agent, wherein said ligand is an aromatic group and said oligonucleotide is homologous to and can silence, e.g., by cleavage, a gene which mediates a neurological disease or disorder; and administering a therapeutically effective dose of said ligand-conjugated oligonucleotide agent to a subject, preferably a human. In a preferred embodiment the disease or disorder is Alzheimer Disease or Parkinson Disease. In particularly preferred embodiments the oligonucleotide agent silences an amyloid-family gene, e.g., APP; a presenilin gene, e.g., PSEN1 and PSEN2, or I-synuclein. In an embodiment the disease or disorder is a neurodegenerative trinucleotide repeat disorder, e.g., Huntington disease, dentatorubral pallidoluysian atrophy or a spinocerebellar ataxia, e.g., SCA1, SCA2, SCA3 (Machado-Joseph disease), SCA7 or SCA8.

In particularly preferred embodiments the oligonucleotide agent silences HD, DRPLA, SCA1, SCA2, MJD1, CACNL1A4, SCA7, SCA8.

The loss of heterozygosity (LOH) can result in hemizygosity for sequence, e.g., genes, in the area of LOH. This can result in a significant genetic difference between normal and disease-state cells, e.g., cancer cells, and provides a useful difference between normal and disease-state cells, e.g., cancer cells. This difference can arise because a gene or other sequence is heterozygous in euploid cells but is hemizygous in cells having LOH. The regions of LOH will often include a gene, the loss of which promotes unwanted proliferation, e.g., a tumor suppressor gene, and other sequences including, e.g., other genes, in some cases a gene which is essential for normal function, e.g., growth. Methods of the invention rely, in part, on the specific cleavage or silencing of one allele of an essential gene with a ligand-conjugated oligonucleotide agent of the invention. The oligonucleotide agent is selected such that it targets the single allele of the essential gene found in the cells having LOH but does not silence the other allele, which is present in cells which do not show LOH. In essence, it discriminates between the two alleles, preferentially silencing the selected allele. In essence polymorphisms, e.g., SNPs of essential genes that are affected by LOH, are used as a target for a disorder characterized by cells having LOH, e.g., cancer cells having LOH. E.g., one of ordinary skill in the art can identify essential genes which are in proximity to tumor suppressor genes, and which are within a LOH region which includes the tumor suppressor gene. The gene encoding the large subunit of human RNA polymerase II, POLR2A, a gene located in close proximity to the tumor suppressor gene p53, is such a gene. It frequently occurs within a region of LOH in cancer cells. Other genes that occur within LOH regions and are lost in many cancer cell types include the group comprising replication protein A 70-kDa subunit, replication protein A 32-kD, ribonucleotide reductase, thymidilate synthase, TATA associated factor 2H, ribosomal protein S14, eukaryotic initiation factor 5A, alanyl tRNA synthetase, cysteinyl tRNA synthetase, NaK ATPase, alpha-1 subunit, and transferrin receptor.

Accordingly, another aspect of the invention relates to a method of treating a disorder characterized by LOH, e.g., cancer. The method comprises optionally, determining the genotype of the allele of a gene in the region of LOH and preferably determining the genotype of both alleles of the gene in a normal cell; providing a ligand-conjugated oligonucleotide agent which preferentially cleaves or silences the allele found in the LOH cells; and administering a therapeutically effective dose of said ligand-conjugated oligonucleotide agent to the subject, preferably a human.

The invention also includes a ligand-conjugated oligonucleotide agent disclosed herein, e.g., an oligonucleotide agent which can preferentially silence, e.g., cleave, one allele of a polymorphic gene.

In another aspect, the invention provides a method of cleaving or silencing more than one gene with a ligand-conjugated oligonucleotide agent. In these embodiments the oligonucleotide agent is selected so that it has sufficient homology to a sequence found in more than one gene. For example, conserved sequences between mouse lamin B1, lamin B2, keratin complex 2-gene 1 and lamin A/C. Thus, an oligonucleotide agent targeted to this sequence would effectively silence the entire collection of genes.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

6. EXAMPLES

The pharmacological effectiveness of oligonucleotides has been hampered by their tendency to remain entrapped in endosomes thus limiting their access to cytosolic or nuclear targets. We have previously reported a group of small molecules that enhance the effects of oligonucleotides by causing their release from endosomes. Here we describe a second family of oligonucleotide enhancing compounds that is chemically distinct. We demonstrate that these molecules substantially augment the actions of splice switching oligonucleotides (SSOs) and antisense oligonucleotides (ASOs) in cell culture. We also find enhancement of SSO effects in a murine model. These new compounds act by increasing endosome permeability and cause partial release of entrapped oligonucleotides. While they also affect the permeability of lysosomes, they are clearly different from typical lysosomotropic agents.

6.1. Introduction

Investigators have sought to utilize the precise effects of siRNA, antisense oligonucleotides (ASOs), and splice switching oligonucleotides (SSOs) for the therapy of cancer and other diseases. (1, 2) However, even with massive investments in the medicinal chemistry and formulation of these molecules, (3, 4) and despite initial advances in the clinic, (5, 6) therapeutic use of oligonucleotides has thus far succeeded to only a limited degree. An important constraining factor is the ineffective delivery of oligonucleotides to their intracellular sites of action in the cytosol or nucleus, due in large part to trapping in endosomal compartments. (7-9)

Oligonucleotides enter cells by various endocytotic pathways. (10, 11) Initial uptake is followed by trafficking into multiple endomembrane compartments including early/sorting endosomes, late endosomes/multivesicular bodies, lysosomes, and the Golgi complex. (12, 13) During trafficking events, discontinuities in the lipid bilayer can occur, thus potentially allowing for partial escape of vesicle contents. (14, 15) Patterns of intracellular trafficking are regulated by a plethora of proteins that modulate the formation, movement and coalescence of membrane bound vesicles. (16, 17) Thus, it seems likely that small molecules could potentially regulate intracellular trafficking as well as the permeability properties of endomembrane vesicles. However, few such compounds have been described. (18, 19)

Recently, we conducted a high-throughput screen of multiple, diverse chemical libraries to identify small molecules that could enhance the pharmacological activities of oligonucleotides. We have previously reported a description of the screen as well as initial characterization of one group of oligonucleotide enhancing compounds (OECs) that act by partially releasing oligonucleotides from entrapment within endosomes. (20 Here, we describe a second family of compounds derived from a hit that emerged from that screen. As with the previously reported molecules, these compounds substantially enhance the effectiveness of oligonucleotides in the absence of any conventional transfection agents. The current compounds also act by increasing oligonucleotide release from endomembrane compartments. However, there is a relatively narrow gap between effective and toxic concentrations.

The original high throughput screen involved a HeLa cell line stably transfected with a luciferase reporter construct that is responsive to SSOs. Approximately 150 000 compounds were tested for their ability to enhance the luciferase induction effect of a SSO but not a mismatched oligonucleotide. The prototypical compound of the first family of small molecules discovered in the screen was termed UNC10217938 and has been described in detail elsewhere. (20)

UNC2383, which emerged as another preliminary hit from our high throughput screen, is chemically distinct from previously published oligonucleotide enhancing compounds (FIG. 1B). We tested UNC2383 for its ability to increase the effectiveness of a SSO using an assay that was similar to the initial high throughput screen. The cells were first incubated with the SSO followed by brief treatment with UNC2383; thereafter luciferase activity and cell protein were measured. As seen in FIG. 1C, exposure to increasing concentrations of UNC2383 resulted in progressive increases in luciferase induction. This result was highly specific since incubation with a mismatched oligonucleotide followed by UNC2383 had no effect. The onset of action of UNC2383 was quite rapid with effects first observed within 30 min and reaching a plateau by 120 min (FIG. 1D). The cytotoxicity of 2383 in two cell lines is depicted in FIG. 1E. As seen, the compound showed little toxicity at concentrations of 10 μM or less, but toxicity was evident at higher concentrations.

In an effort to improve the efficacy and reduce toxicity of UNC2383, we prepared several analogs. While some were inactive (namely, those resulting from modification to the ethylpyrrolidine side chain), several closely related analogs, which generally contain modifications to the substituents on the benzofuran and benzimidazole ring systems (see FIG. 2), displayed activity in enhancing SSO effects. Typical dose-response curves for luciferase induction and cytotoxicity are shown in FIG. 3. A summary of EC50 versus TC50 data for the analogs is given in Table 2. Interestingly, UNC4267 had somewhat reduced potency relative to UNC2383 but was also substantially less toxic. These results suggest that considerable alterations in effectiveness and toxicity may be possible through further modification. Chemical information regarding the synthesis of the various analogs is provided below.

TABLE 2

TC50/EC50 Ratios for 2383 Analogs[a]

| Compound | EC50 (μM) | TC50 (μM) | TC50/EC50 |
|---|---|---|---|
| UNC2383 | 2 | 15 | 7.5 |
| UNC4425 | 6 | 12.5 | 2.1 |
| UNC4426 | 3.5 | 13 | 3.7 |
| UNC4428 | 10 | 50 | 5 |
| UNC4251 | 2 | 7 | 3.5 |
| UNC4253 | 11 | 48 | 4.4 |
| UNC4258 | 13 | 65 | 5 |
| UNC4267 | 8 | 68 | 8.5 |

We also tested UNC2383 for its ability to affect ASOs rather than SSOs. The ASO was designed to inhibit expression of the MDR1 gene and its product the P-glycoprotein multidrug transporter. (21) Multidrug resistant NIH-3T3-MDR cells were incubated with ASOs with or without further treatment with UNC2383 (FIG. 4). One set of cells was treated with the ASO complexed with Lipofectamine 2000 as a positive control. Cell surface expression of P-glycoprotein was monitored using an Alexa 488 labeled anti-Pgp monoclonal antibody and flow cytometry. Treatment of the NIH-3T3-MDR cells with ASO alone had virtually no effect on Pgp levels, while treatment with ASO complexed with Lipofectamine 2000 caused a left shift of the flow cytometry profile indicating reduced Pgp expression. Similarly, incubation with ASO followed by treatment with UNC2383 resulted in a substantial reduction in Pgp expression, thus indicating that UNC2383 can strongly enhance effects of ASOs as well as SSOs.

Based on the above results, wherein UNC2383 enhanced the effects of both SSOs and ASOs, molecules which have completely distinct mechanisms of action, it seemed likely that UNC2383 affects the trafficking and delivery of the oligonucleotides rather than their molecular mechanisms. Accordingly, we tested UNC2383 for its ability to release material from endomembrane entrapment. Thus, cells were incubated with a highly fluorescent dextran that is taken up via pinocytosis, then rinsed and treated with UNC2383, followed by observation using confocal fluorescence microscopy. As seen in FIG. 5A panels a, b control cells displayed an abundance of distinct, highly fluorescent vesicles containing entrapped dextran. However, there was no visible fluorescence in the cytosol itself. In contrast, in cells exposed to UNC2383 (FIG. 5A panels c, d), the fluorescence intensity of vesicles was reduced, and there was clear evidence of a diffuse cytosolic fluorescence. This indicates that UNC2383 caused partial release of the dextran from vesicular entrapment. We also examined effects on the distribution of a SSO labeled with the fluorophore TAMRA. As seen in FIG. 5A panels e, f, treatment with UNC2383 caused a partial but substantial relocalization of the labeled oligonucleotide to the nucleus, which was delineated using a Hoechst dye. Quantitation of the increase in TAMRA fluorescence in the nucleus due to UNC2383 is shown in FIG. 5B. Thus, UNC2383 seems to act in a manner similar to previously described oligonucleotide enhancing compounds (18, 20) in that it increases the permeability of endomembranes, which allows oligonucleotides to have greater access to the cytosol and nucleus. Encouragingly, similar results on oligonucleotide redistribution to the nucleus were seen with other UNC2383 analogs (FIG. 6).

We also examined the effects of UNC2383 on the colocalization of the SSO with markers for specific endomembrane compartments by using baculovirus vectors that express GFP chimeras of marker proteins (FIG. 7A-7B). In control cells, there was substantial colocalization of the TAMRA-SSO with GFP-LAMP1, a lysosome marker (FIG. 7A panel a), and with GFP-Rab7, a late endosome marker (FIG. 7A panel c). Treatment with UNC2383 caused a partial relocalization of the TAMRA-SSO to the nucleus and affected its colocalization with marker proteins (FIG. 7A panel b, d). Additional examples of these effects are shown in FIG. 8. The extent of colocalization of oligonucleotides with the endomembrane marker proteins was quantitated using Manders' Correlation Coefficient (22) and is shown in FIG. 7B. Treatment with UNC2383 substantially reduced the degree of colocalization of the TAMRA-SSO with both late endosomes and lysosomes, as would be expected given the relocalization of oligonucleotide to the nucleus using this compound.

We also investigated the effects of our compounds on lysosomes since such interactions may have toxic consequences. The effects of our compounds on the integrity of lysosomes were evaluated using the fluorescent probe Lysotracker Red, which accumulates in low pH compartments, particularly lysosomes. Thus, perturbation of the integrity of the lysosome membrane would lead to leakage of protons, increased intralysosomal pH, and reduced lysotracker accumulation. As seen in FIG. 9A, low concentrations of UNC2383 or its analogs that were effective in luciferase induction, but nontoxic in the Alamar Blue cytotoxicity assay, had limited effects on lysotracker accumulation, while higher concentrations of the compounds strongly affected this parameter. For example, 2 μM UNC2383 or 10 μM UNC4267, UNC4258, or UNC4428, concentrations that quite strongly enhanced SSO actions (see FIG. 1C and FIG. 3), had little effect on lysotracker accumulation. This suggests that, at low compound concentrations, some oligonucleotide is released from higher pH endomembrane compartments that do not strongly accumulate lysotracker dye, while at high compound concentrations, low pH compartments such as lysosomes are also affected.

A plot of the concentration for 50% toxicity versus the concentration for 50% inhibition of lysotracker accumulation for 5 analogs showed an approximately linear relationship (FIG. 1B). Thus, part of the toxicity of these compounds may be ascribed to permeabilization of lysosomes, although other effects cannot be ruled out. There is an enormous amount of literature on the benzimidazole pharmacophore with various compounds described as having multiple therapeutic or toxic effects; (23) thus it is difficult to specify additional toxicities. Interestingly, substantial reductions in lysotracker accumulation were observed at compound concentrations that did not affect cell viability, indicating that some degree of permeabilization of lysosomes can be tolerated. This is also suggested by the slope of FIG. 9B that is less than 1 (~0.5). Importantly, although UNC2383 and its analogs affect lysosomes, they are not typical lysosomotropic compounds. This is clearly shown in FIG. 9C and FIG. 9D where we compare the effects of UNC2383 to those of chloroquine, a classic lysosomotrope. Chloroquine had little effect on SSO-mediated luciferase induction even at very high concentrations or long duration of exposure, whereas UNC2383 was very active at nontoxic concentrations.

We have also examined the effects of UNC2383 in vivo. We used a transgenic mouse model termed EGFP654 that incorporates an EGFP reporter whose coding sequence is interrupted by an intron that is aberrantly spliced, resulting in failure to produce mature EGFP mRNA and protein. (24) However, successful delivery of an appropriate SSO will correct splicing, leading to restoration of message and protein expression in tissues. (20) In these studies, we pretreated mice with the SSO and subsequently administered UNC2383. As seen in FIG. 10A-10E, treatment with the SSO plus the small molecule resulted in an increase in correctly spliced EGFP message above that provided by the SSO alone. Results are shown for liver, kidney, lung, and intestine, but splice correction was observed in other tissues as well. The magnitudes of the enhancing effects observed in vivo were much less than those observed in cell culture. However, this is not uncommon, and at this point nothing is known about the pharmacokinetics or biodistribution of these compounds; thus the route and schedule of administration may have been suboptimal.

We also examined correction at the protein level by using an anti-EGFP antibody. FIG. 10F shows that the epithelial cells of bronchi and intestinal crypts expressed EGFP in mice that received both SSO623 and UNC2383, as compared to control mice that received mismatched oligo plus UNC 2383, or SSO623 in the absence of the small molecule. In the intestine, the most proximal region of the crypt exhibited the highest expression probably due to the effect of epithelial regeneration in the time frame of treatment. As expected, the liver exhibited degrees of expression with all SSO treatments, but EGFP immunostaining was highest in mice treated both with the SSO and the small molecule.

Airways and intestines are difficult therapeutic targets for oligonucleotides in genetic disorders such as cystic fibrosis (25, 26) thus it is interesting that effects were observed in these tissues. In these experiments, toxicity was monitored by obtaining blood samples and analyzing parameters that reflect renal, hepatic, and hematotoxicity (Supporting Table 1). The only indication of toxicity was a moderately elevated level of the liver enzyme ALT, although this was not significant at the 5% level.

The experiments described above indicate that UNC2383 can substantially enhance the pharmacological effects of oligonucleotides in cell culture and provide in vivo enhancement as well, accompanied by limited toxicity. Our studies suggest that UNC2383 acts similarly to previously described OECs in that it increases the permeability of endomembrane compartments. (18, 20) This allows partial release of oligonucleotides from nonproductive endomembrane entrapment and provides access to targets in the cytosol or nucleus. While it is clear that UNC2383 and its closely related analogs act on endomembranes, we have not yet pursued the precise molecular target since the affinity of these compounds is likely too low to permit identification by proteomic or lipidomic techniques. Although higher concentrations of UNC2383 and various analogs can affect lysosomal pH, data presented here clearly show that their action is quite distinct from typical lysosomotropic compounds such as chloroquine. Thus, simple pH-driven drug accumulation and subsequent osmotic swelling of endomembranes cannot account for the oligonucleotide enhancing effects observed here. The observations of FIGS. 7A-7B and FIGS. 9A-9D suggest that low concentrations of UNC2383 and its analogs primarily affect endosomes, while higher concentrations can affect both endosomes and lysosomes. Although we have examined only SSOs and ASOs in this report, we anticipate that UNC2383 and related OECs will also affect the actions of siRNA, as well as various types of oligonucleotide conjugates, since these molecules are also restricted by endomembrane trapping. (27)

In comparing to previously described oligonucleotide enhancing compounds including Retro-1(18) and UNC10217938, (20) it seems that compound UNC2383 is far more effective than Retro-1 and approximately equivalent to UNC 10217938 in terms of actions in cells. However, the window between effective and toxic concentrations is narrower for UNC2383 than for UNC10217938. We hypothesize that UNC10217938 may be more selective for endosomes rather than lysosomes as compared to UNC2383, but this remains to be determined. The OECs described here are all closely related to the initial hit from a high throughput screen and are thus still far removed from being mature drug candidates. However, further analysis of structure-activity relationships may lead to the development of new compounds with greater efficacy and reduced toxicity. It is interesting to note that other groups have begun to describe oligonucleotide enhancing small molecules. (28, 29) The structures of those molecules are very different from ones described here or previously by us, (20) suggesting that there may be a variety of mechanisms by which small molecules can augment effects of oligonucleotides.

6.2. Lung Delivery and Cystic Fibrosis (CF)

Other diseases associated with genetic defects may also respond to oligonucleotide-based therapeutics. An important example is Cystic Fibrosis (CF). This relatively common autosomal recessive disease is caused by various mutations in CFTR, a cAMP regulated chloride channel that strongly influences epithelial salt and water transport. Defects in CFTR lead to a multi-organ disease typified by chronic pulmonary pathology as well as detrimental changes in the GI tract, pancreas, and male reproductive tract. Loss of CFTR function results in the formation of dehydrated, viscous mucous that retards clearance and sets the stage for chronic bacterial infections. Until recently only symptomatic therapies were available for CF. However, recent research led to several small molecules that, at the protein level, modulate the function of certain CFTR mutants. Thus, Ivactafor®/Kalydeco® potentiates CFTR channel function in patients harboring the G551D mutation. Despite this progress, CF patients harboring other types of CFTR mutations lack recourse to effective therapy. For example, ~11% of the ~75,000 CF patients worldwide are affected by splicing mutations, the most common being 3849+10 kbC-T (http://www.genet.sickkids.on.ca/app). Although Kalydeco® has been approved to use in these patients, it does not address the underlying molecular defect, and has no effect in patient-derived cell cultures. However, this patient cohort potentially could receive corrective treatment using appropriate SSOs, as suggested by our work with SSOs in cell models. This would allow substantial quality of life improvement and possibly decreased mortality.

Despite recent clinical successes there remain persistent obstacles to the therapeutic use of oligonucleotides. A main issue is the delivery problem. Oligonucleotides do not diffuse across cell membranes. Whether administered as 'free' molecules or associated with delivery agents such as lipid or polymer nanoparticles, oligonucleotides are taken up via endocytosis and then traffic to intracellular membrane compartments such as early and late endosomes and lysosomes. Within these compartments oligonucleotides are pharmacologically inert since they cannot access their molecular targets in the cytosol or nucleus. In the absence of a delivery moiety, oligonucleotides slowly leak into the cytosol and can then reach the nucleus. The currently approved oligonucleotide drugs all work this way. However, the slow leakage is rather inefficient; thus enormous efforts have been made to enhance oligonucleotide delivery. There are several major approaches to augmenting oligonucleotide delivery.

UNC2383 was published by Juliano, Kreda, et al in 2017 (Wang et al. 2017, ACS chemical biology, 12, 1999-2007, the contents of which are incorporated in its entirety) showing activity in vivo via systemic delivery of the free base compound. UNC2383 showed enhancing activity of the specific SSO (systemic delivery) targeting the EGFP splicing mutation in the liver (CF target), intestinal crypts (CF target), airways and submucosal glands (CF target), and muscle (CF and other genetic diseases) (FIG. 10A-10F). However, in vitro, the free base of this compound has negligible activity in human airway epithelial cells. We discovered that a salt/solubilized chemical form of UNC2383 (specifically the hydrochloride salt) has significant activity (10-20 times higher) than the free base (parental compound) in vitro in human airway epithelial cells and have significant activity in primary mouse airway cells. This chemical change reduced the effective dose, increasing the therapeutic index in vitro and increasing the apical activity, which was undetected with the free base compound (FIG. 12 and FIG. 13).

2—Target: UNC2383 salt has significant activity in primary airway epithelial cells derived from: (a) CF patient homozygous for the 3849+10 kbC-T CF splicing mutation (FIG. 12), and (b) Mouse tracheal cells derived from a mouse with a reporter EGFP encoding a splice mutation that can be corrected by SSO (correction results in green fluorescence expression, FIG. 13).

3—Delivery: UNC2383 salt enhancing activity on the specific SSOs in the primary cultures from CF patient airways and mouse tracheas is significant after apical delivery of UNC2383. Apical delivery mimics direct delivery into the airways, i.e., aerosolization; which can reduce putative systemic off effects and thus, increase therapeutic index for lung therapeutics (FIGS. 12 and 13.

4—Therapeutic applications: UNC2383 (solubilized form) has activity in human airway cells with CF splicing mutations using specific CFTR SSOs (FIG. 12), in mouse airway cells with EGFP encoding an artificial splicing mutation using a specific EGFP SSO (FIG. 13), in a human airway cell line using fluorescently-tagged SSOs (FIG. 14). The data indicate UNC2383 can enhance the activity of different SSOs with different targets; thus, we can assume that UNC2383 could be used in combination with different SSOs or oligonucleotides for therapeutic correction of other CF splicing mutations, or oligonucleotide-targeted mutations in other diseases with tissues responsive to UNC2383.

5—CF splicing mutations: ~11% of the ~75,000 CF patients worldwide and ~30,000 CF patients in the USA are affected by splicing mutations. Some of these mutations express severe CF phenotype and will be very difficult to be corrected with potentiator (Vertex-like) compounds because there is no protein expressed. Some of the splicing mutations are frequent in CF populations outside the USA (see map, below) and there are several international research groups actively pursuing therapeutic approaches for CF splicing mutations.

Moreover, as shown in FIG. 15A-15B, the combination of the benzimidazole oligonucleotide enhancing compounds disclosed herein and the compounds disclosed in US2017/0130222A (Juliano et al.) may be used with peptide-morpholino conjugates. See the figure descriptions for FIG. 15A-15B for the experimental details.

Summary

Splicing mutations result in the loss of functional CFTR in ~11% of CF patients, e.g., the 3849+10 kbC→T mutation is expressed in 0.2-5% of CF patients. Although Kalydeco® has been approved for use in these patients, it does not address the underlying molecular defect. This patient cohort could receive corrective treatment using splice switching oligonucleotides (SSOs). Clinically, SSOs have been tested successfully to modify splicing and reestablish lost functions in patients with genetic diseases, including Duchene muscular dystrophy and spinal muscular atrophy. However, a main therapeutic block in lung, intestine, and other tissues is inefficient intracellular delivery of SSOs, which are trapped in endosomes and rendered inactive. Thus, SSO-driven corrective CFTR strategies are currently suboptimal for clinical applications. We have implemented a novel approach to correct splicing defects in CF by using effective SSOs in combination with small molecules Oligonucleotide Enhancing Compounds (OECs), to overcome deficient intracellular trafficking of SSOs. The Objective of this project is to test the combined administration of SSOs & OECs for efficient splice mutation correction in CF relevant in vitro and in vivo models.

Results: In vitro studies were performed in well-differentiated HBEC cells derived from a homozygous 3849+10 kbC→T CF patient (CF HBEC) treated with one dose of a specific SSO (1 uM, 12 hs) followed by one dose of OEC (apical or basolateral delivery, 2-4 uM, 2-3 hs). A significant increase of forskolin-stimulated CFTR activity in Ussing chamber analyses was observed 24-96 hs after SSO+OEC treatment compared to SSO alone treatment or vehicle. OEC was efficacious delivered apically as well as basolaterally. Transepithelial resistance and microscopy tests were implemented to monitor cytotoxicity, which was negligible for both SSO and OEC (FIG. 12). In vivo studies were performed in a transgenic mouse model that has a SSO-inducible EGFP reporter. Proof of concept in vivo studies indicated that systemic, sequential administration of SSO and OEC effectively corrected EGFP splicing, rendering EGFP-expressing cells in CF relevant tissues: airway, colon, and liver, compared to administration of SSO alone or mismatched SSO+OEC. Systemic toxicity and lung morphology revealed negligible toxicity for SSO and OEC treatments (FIG. 10F).

SSOs (100 nM) were introduced in airway epithelial cells derived from a 3849+10 kbC-T homozygous CF patient in suspension by electroporation using the Neon system, program A4. Cells were differentiated for 2 weeks in culture on human collagen-coated permeable supports (Millipore) before being tested in Ussing chambers following methods described in Kreda et al. 2015 "Characterization of Wild-Type and ΔF508 Cystic Fibrosis Transmembrane Regulator in Human Respiratory Epithelia" Mol. Biol. Cell 16(5): 2154-2167 (100 uM Amiloride, Amil; 10 uM Forskolin, Fsk; 20 uM CFTR inhibitor 172). After Ussing chamber analysis, cells were lysed and assayed for RT-PCR as described in Wang et al 2017 (FIG. 11).

CFTR Sequences, SSO A=mG*mU*+C*mU*m*mU*mA*+C*mU*+C*mA*mC*+C*mA*mU*mU*mU*mU*+A (SEQ ID NO:1) with similar modifications on B (+C*mU*mU*mA*mC*+U*mC*mA*mC*mC*+A*mU*mU*mU*+U*mA*mA*mU) (SEQ ID NO:2), C (5'+G*mA*mG*mU*+C*mU*mU**mU*mA*+C*mU*mC*mA*mC*mC*+A*mU*mU*mU) (SEQ ID NO:3) (Locked Nucleic Acid (LNA)=+, PS=*, 2'OMe=m). In SSO sequences A, B, and C the underlined bases indicate oligo bases that match up to the bases in the mutated splice site in the 3849+10 kb C-T CFTR splicing mutation. MM623 or SSO623 sequences are described herein. The results are shown in FIG. 12. Methods: SSO A (1 uM from FIG. 11) was incubated basolaterally overnight in well-differentiated airway epithelial cells derived from a 3849+10 kbC-T homozygous CF patient; OEC2383 was administered apically or basolaterally (1-4 uM for 2-3 hs). Forty eight-seventy two hours later, Ussing chamber analysis was performed as described above and for FIG. 1B-1E. The results are shown in FIG. 12 which shows work with primary cultures of patient derived human bronchial airways cells (HBEC). These particular cells are from a patient homozygous for the 3849+10 kb C-T CFTR splicing mutation. Thus, the importance of this figure is that it shows that our SSOs plus enhancing compound (UNC2383) work in the cells of the ultimate therapeutic target.

Methods: SSO623 (1 uM) was incubated basolaterally overnight in well-differentiated primary tracheal epithelial cells (MTEC) derived from the EGFP654 mouse (Wang et al, 2017); OEC2383 was administered apically or basolaterally (1-4 uM for 2-3 hs). Twenty four hours to 21 days later cell cultures were imaged live on a confocal microscope Leica SP6 with a 63× glycerol immersion lens using xy and xz laser scanning. The results are shown in FIG. 13.

Conclusions: Our strategy of combined administration of SSOs and OEC dramatically increases the efficacy of SSOs in CF-relevant cell types using relatively low doses of SSO/OEC and revealing low toxicity in in vivo and in vitro studies. Restoring CFTR function to correct CF disease may require a variety of specific and individualized pharmacological approaches. While some mutations may be "corrected" with small molecules at the protein level, patients with the splicing mutation 3849+10 kbC-T may benefit from therapeutic gene editing. Our strategy can be applied to other CF splicing mutations by modifying the SSO specificity, signifying the translational potential of our combined SSO & OEC approach for CFTR corrective therapies.

6.3. General Methods

Cells and Culture Methods

HeLaLuc705 cells are stably transfected with a firefly luciferase reporter whose coding sequence is interrupted by an abnormal intron. Effective delivery of an appropriate SSO, such as the 2'-O Me phosphorothioate SSO623 (5'-GTTATTCTTTAGAATGGTGC-3')(SEQ ID NO: 4), to the nucleus of these cells will correct splicing and allow luciferase expression. NIH-3T3-MDR cells are stably transfected with a human MDR1 cDNA coding for the P-glycoprotein (Pgp). We have described the maintenance and use of these cell lines elsewhere. (18, 20)

Functional Assays in Cell Models

SSO-mediated luciferase induction assays were conducted as previously described. (18) In short, HeLaLuc705 cells in 24 well culture plates were preincubated with SSO623 followed by brief treatment with the small molecule; at intervals thereafter, luciferase activity and protein content were determined. ASO mediated inhibition of MDR1 gene expression utilized an Alexa 488 labeled anti-P-glycoprotein antibody and flow cytometry to measure Pgp expression as described. (20) The anti-MDR1 sequence is 5'-CCATCccgacctcgcGCTCC-3'(SEQ ID NO: 5) (all phosphorothioate with 2-O-Me residues in capitals). Cytotoxicity of 2383 was monitored using the Alamar Blue assay. (30)

Confocal Microscopy and Immunostaining

Effects of UNC2383 on endosome stability were monitored in cell culture models as previously described. (20) Briefly, HeLaLuc705 cells were preincubated overnight with Alexa 488 labeled dextran or with TAMRA-labeled SSO 623. Live cells were imaged by fluorescence confocal microscopy with or without treatment with UNC2383 or its analogs. In some cases, the location of the nucleus was delineated by treating the cells with Hoechst 33342 (ThermoFisher Scientific) at 5 ug/mL in PBS after exposure to analogs. In some cases, cells were transfected with baculovirus expression vectors (Cell Lights, Life Technologies) for GFP-Rab7a (late endosome marker) or GFP-LAMP-1 (lysosome marker). Live cell imaging utilized a Zeiss LSM710 confocal microscope with an environmental stage. Co-localization of TAMRA labeled SSO 623 with marker proteins was quantitated using Fiji (ImageJ) software and expressed as a Manders' Correlation Coefficient. (22) For the in vivo effects of UNC2383, EGFP protein expression was examined in formalin-fixed, paraffin embedded tissues harvested from treated or control mice. EGFP protein expression was monitored by immunostaining with an anti-EGFP antibody (Abcam) using techniques previously described. (3) EGFP immunostaining was analyzed using a Leica SP2 confocal microscope with acquisition parameters constant throughout the study: images were processed with Adobe Photoshop software.

Lysotracker Assays

The integrity of lysosomes was evaluated using the fluorescent probe Lysotracker Red (Thermo Fisher). Cells in 24 well culture plates were incubated with various concentrations of UNC2383 or its analogs for 60 min. At this point, 200 nM Lysotracker was added and the incubation continued for an additional 15 min. Cells were thoroughly rinsed in PBS, lysed in 0.2% TX 100, and centrifuged briefly at 4000 rpm, and 100 uL of the supernate was distributed to black 96 well plates for analysis of fluorescence using a FLUOstar Omega 96 well microplate reader.

In Vivo Studies

All animal procedures were conducted in compliance with guidelines of the UNC Laboratory Animal Medicine Department and with federal guidelines. The EGFP654 transgenic mouse contains a reporter gene comprised of the EGFP coding sequence interrupted by an aberrantly spliced intron. (24) Correct splicing and EGFP production can be restored by delivery of an appropriate SSO to the nucleus of tissue cells. (20, 32) EGFP654 mice were administered 35 mg/kg of SSO623 or mismatched oligonucleotide in buffer by intraperitoneal injection on two consecutive days. One day later, mice received either 5 mg/kg of UNC2383 in a 1:1 DMSO/PEG400 solution or only the diluent, via intraperitoneal injection. After 5 h, one cohort of mice was euthanized and tissue samples collected for RNA analysis. These were quick frozen on dry ice and RT-PCR performed as we have previously described (18, 20) (additional details in the Supporting Information). After 24 h, the second cohort was euthanized and tissue and cardiac blood samples were obtained. Tissues were fixed in 10% formalin and processed for EGFP antibody staining as described. (31) Blood samples were analyzed by the UNC Animal Clinical Chemistry Core facility.

TABLE 1

In Vivo Toxicity Parameters
Cardiac blood samples were collected at the termination of the experiment described in FIG. 10 (24 h after administration of the test compound). The UNCAnimal Clinical Chemistry Core analyzed the samples for the following parameters. Blood urea nitrogen (BUN); alanine aminotransferase (ALT); aspartate aminotransferase (AST); hemoglobin (Hb); platelet count. None of the differences between experimental and control were significant at the 5% level using the paired t-Test.

| Mice | BUN | ALT | AST | Hb | Platelets |
|---|---|---|---|---|---|
| Control | 22 +/− 3 | 53 +/− 8 | 84 +/− 18 | 13.2 +/− 0.7 | 838 +/− 15 |
| SSO623 only | 23 +/− 2 | 51 +/− 8 | 65 +/− 23 | 13.8 +/− 0.8 | 824 +/− 266 |
| SSO623 + 2383 | 25 +/− 11 | 116 +/− 59 | 62 +/− 5 | 10.0 +/− 2.6 | 770 +/− 587 |
| 2383 only | 20 +/− 4 | 106 +/− 32 | 76 +/− 15 | 11.8 +/− 0.4 | 711 +/− 85 |

Values are means +/− SE. N = 4.
Units: BUN mg/dl, ALT U/L, AST U/L, Hb g/dl, Platelet × $10^3$/ul

TABLE 2

Protein Content for Luciferase Assay in FIG. 1C.

| UNC2383 in uM | Protein Content in Luciferase Sample (ug) Mean Value (N = 3) | S.E. |
|---|---|---|
| 0 | 5.4 | 0.1 |
| 1 | 5.4 | 0.2 |
| 2 | 5.3 | 0.2 |
| 3 | 5.4 | 0.2 |
| 5 | 5.6 | 0.2 |
| 8 | 5.5 | 0.3 |
| 10 | 5.4 | 0.1 |
| 15 | 4.8 | 0.2 |

Additional Methods and Statistical Information:

PCR techniques. Total RNA was isolated using TriReagent (Molecular Research Center). Total RNA was normalized by measuring OD260 on a NanodropTMspectrophotometer and then converted into first-strand cDNA using an Enhanced Avian First Strand Synthesis Kit (Sigma). EGFP cDNA was amplified by PCR using forward (5'-CGTAAACGGCCACAAGTTCAGCG-3') (SEQ ID NO:6) and reverse (5'-GTGGTGCAGATGAACTTCAGGGTC-3') (SEQ ID NO:7) primers. The PCR products were separated on 1.5% agarose gels and bands were visualized by staining with Gel RedTMand quantitated using a Biorad ChemiDoc XRS+ scanner. Statistical Information. Confocal images were analyzed using the Fiji (Image J) software package. Overlap of red and green fluorescence was quantitated by calculation of the Manders Coefficient using the Jacop plug in. Quantitation of nuclear accumulation of TAMRA-labeled oligonucleotide was done by measuringgrey scale intensity in the red channel in an area previously outlined using Hoechst stain. Evaluations of the significance of differences between experimental samples and controls in confocal and PCR measurements were done using the paired T-test. Calculation of the R2 value for FIG. 9 panel b was done with Prism™ software.

6.4. Chemical Synthesis

General Information

Analytical LCMS data for all compounds were acquired using an Agilent 6110 series system with the UV detector set to 220 and 254 nm. Samples were injected (<10 μL) onto an Agilent Eclipse Plus 4.6×50 mm, 1.8 um, C18 column at room temperature. A mobile phase of A ($H_2O$+0.1% acetic acid) and B (MeOH+0.1% acetic acid) was used with a linear gradient from 10% to 100% B in 5.0 min, followed by a flush at 100% B for another 2 minutes with a flow rate of 1.0 mL/min. Mass spectra data were acquired in positive ion mode using an Agilent 6110 single quadrupole mass spectrometer with an electrospray ionization source. Nuclear Magnetic Resonance (NMR) spectra were recorded on a Varian Mercury spectrometer at 400 MHz for proton ($^1$HNMR), and 100 MHz for carbon ($^{13}$CNMR); chemical shifts are reported in ppm (δ). Analytical thin-layer chromatography (TLC) was performed with silica gel 60 F254, 0.25 mm pre-coated TLC plates, generally using a suitable MeOH in DCM solvent system. TLC plates were visualized using UV 254 nm, 12 impregnated silica gel, potassium permanganate with charring, and phosphomolybdic acid with charring. Reverse phase or normal phase chromatography was used to purify reaction mixtures to obtain intermediate products using a Teledyne Isco CombiFlash Rf 200 chromatography unit equipped with the UV detector set to 220 nm and 254 nm. Suitable variations in the purification method (flow rate, solvent system) were made as needed to achieve ideal separation for each compound. All compounds that were evaluated in biochemical and biophysical assays had >95% purity as determined by $^1$HNMR and LCMS.

Scheme 1: Synthesis of UNC2383

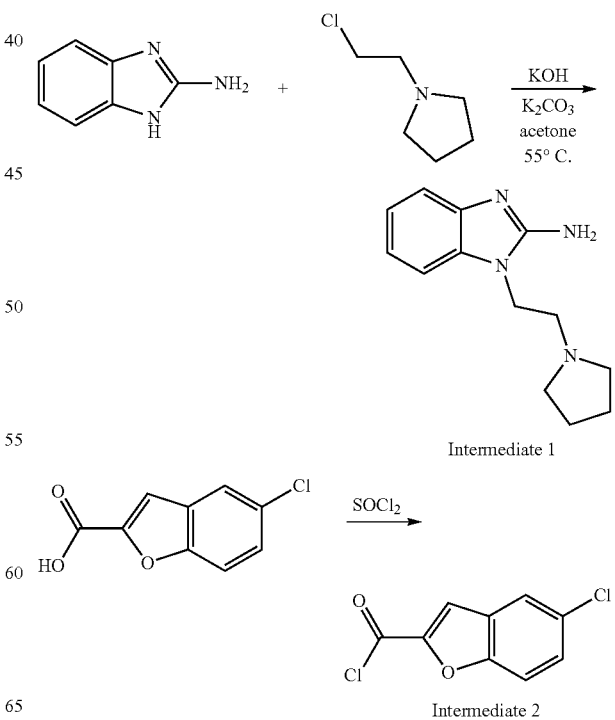

Intermediate 1

Intermediate 2

-continued

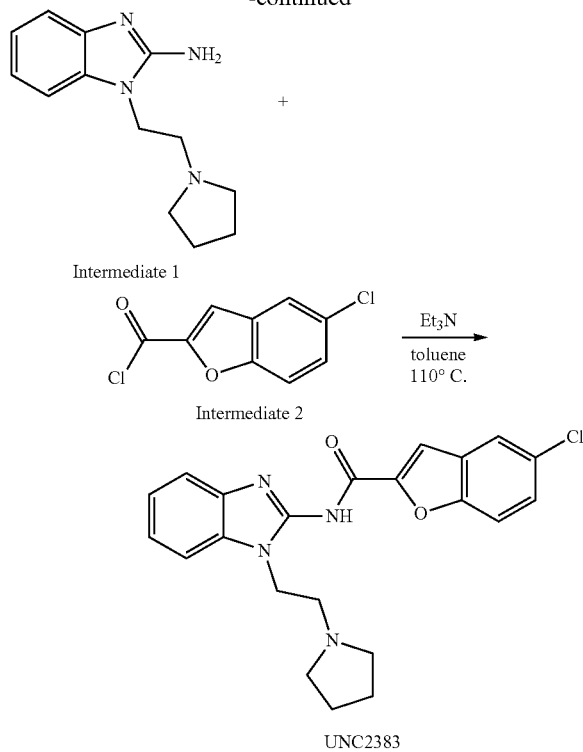

Synthesis of Intermediate 1

To a solution of 2-Aminobenzimidazole (500 mg, 3.75 mmol, 1.0 eq.) and 1-(2-chloroethyl)pyrrolidine hydrochloride (639 mg, 3.75 mmol, 1.0 eq.) in acetone (19 mL) was added powdered KOH (375 mg) and anhydrous $K_2CO_3$ (750 mg), and the reaction mixture was heated under reflux for 3 hours. Upon completion, solvent was removed under reduced pressure to obtain a pale yellow solid. The solid was dissolved in $CH_2Cl_2$ (30 mL) and washed with water (2×30 mL). The aqueous phase was extracted with $CH_2Cl_2$ (3×20 mL) and the organic layers were combined, washed with brine, dried over anhydrous $Na_2SO_4$, filtered, and concentrated under reduced pressure to obtain a pale yellow crude material. The crude material was adsorbed onto silica gel and purified by normal phase automated Teledyne Isco chromatography using $CH_2Cl_2$/MeOH/$NH_3$ solvent system. Intermediate 1 was obtained as a white solid (569 mg, 66%).

$^1$H NMR (400 MHz, DMSO-$d_6$) δ 7.15-7.09 (m, 2H), 6.89 (m, 2H), 4.07 (t, J=6.8 Hz, 2H), 2.68 (t, J=6.8 Hz, 2H), 2.52-2.49 (m, 4H), 1.70-1.61 (m, 4H).

LC-MS (λ=254 nm): 99%, $t_R$=0.6 min. MS (ESI+): 231 [M+H]$^+$

Synthesis of Intermediate 2

5-chlorobenzofuran-2-carboxylic acid (500 mg, 2.5 mmol) was added to thionyl chloride (5 mL) and heated under reflux for 2 hrs. Solvent was removed under reduced pressure to obtain a white solid, which then used in the next reaction without further purification (510 mg).

$^1$H NMR (400 MHz, Chloroform-d) δ 7.76 (d, J=0.9 Hz, 1H), 7.72 (dd, J=2.0, 0.7 Hz, 1H), 7.56-7.48 (m, 2H).

Synthesis of UNC2383

To a solution of intermediate 1 (300 mg, 1.3 mmol, 1.0 eq.) and intermediate 2 (280 mg, 1.3 mmol, 1.0 eq.) in toluene (2 mL) was added triethylamine (0.7 mL, 5.2 mmol, 4.0 eq.), and the reaction mixture was heated under reflux for 3 hours. Upon completion, the reaction was quenched with sat. aqueous $NaHCO_3$ solution (10 mL). The aqueous phase was separated and extracted with $CH_2Cl_2$ (3×10 mL). All combined organic layers were dried over anhydrous $Na_2SO_4$, filtered, and concentrated under reduced pressure to obtain a pale yellow crude material. The crude material was adsorbed onto silica gel and purified by normal phase automated Teledyne Isco chromatography using $CH_2C_{12}$/MeOH/$NH_3$ solvent system. UNC2383 was obtained as a white solid (276 mg, 52%).

$^1$H NMR (400 MHz, Chloroform-d) δ 12.12 (brs, 1H), 7.63 (d, J=2.0 Hz, 1H), 7.51 (d, J=8.8 Hz, 1H), 7.47 (d, J=1.0 Hz, 1H), 7.37 (dd, J=6.4, 2.5 Hz, 1H), 7.33-7.24 (m, 4H), 4.45-4.31 (m, 2H), 2.98-2.86 (m, 2H), 2.71-2.64 (m, 4H), 1.88-1.73 (m, 4H).

LC-MS (λ=254 nm): 99%, $t_R$=5.2 min. MS (ESI+): 409 [M+H]$^+$

Compounds UNC4425, UNC4426, UNC4428, UNC4253, UNC4258, and UNC4267 were prepared by a similar method as UNC2383.

Synthesis of UNC4425

Procedure for the synthesis of UNC2383 was followed to obtain a pale yellow solid.

$^1$H NMR (400 MHz, Chloroform-d) δ 12.14 (brs, 1H), 7.63 (d, J=2.1 Hz, 1H), 7.53-7.49 (m, 1H), 7.48 (d, J=0.9 Hz, 1H), 7.40-7.26 (m, 3H), 7.24-7.20 (m, 1H), 4.35 (q, J=7.0, 6.6 Hz, 2H), 2.92 (t, J=7.1 Hz, 2H), 2.68 (dd, J=7.4, 4.4 Hz, 4H), 1.81-1.77 (m, 4H).

LC-MS (λ=254 nm): 99%, $t_R$=5.6 min. MS (ESI+): 444 [M+H]$^+$

Synthesis of UNC4426

Procedure for the synthesis of UNC2383 was followed to obtain a pale yellow solid.

$^1$H NMR (400 MHz, DMSO-$d_6$) δ 9.44 (brs, 1H), 7.85 (d, J=2.2 Hz, 1H), 7.72 (d, J=8.8 Hz, 1H), 7.62 (d, J=0.9 Hz, 1H), 7.51-7.38 (m, 3H), 7.15-7.10 (m, 1H), 4.62 (t, J=5.5 Hz, 2H), 3.96-3.86 (m, 2H), 3.69-3.62 (m, 2H), 3.26-3.16 (m, 2H), 2.42 (d, J=10.8 Hz, 3H), 2.08-1.99 (m, 2H), 1.82-1.73 (m, 2H). LC-MS (λ=254 nm): 99%, $t_R$=5.7 min. MS (ESI+): 424 [M+H]$^+$ Synthesis of UNC4428

Procedure for the synthesis of UNC2383 was followed to obtain a white solid.

$^1$H NMR (400 MHz, Methanol-$d_4$) δ 7.84 (s, 1H), 7.76 (d, J=2.2 Hz, 1H), 7.71 (s, 1H), 7.63 (d, J=0.9 Hz, 1H), 7.57 (d, J=8.8 Hz, 1H), 7.44 (dd, J=8.8, 2.2 Hz, 1H), 4.70 (t, J=5.4 Hz, 2H), 3.73 (t, J=5.4 Hz, 2H), 3.32 (m, 4H, overlapped with Methanol-$d_4$), 2.12-2.06 (m, 4H). LC-MS (λ=254 nm): 99%, $t_R$=5.8 min. MS (ESI+): 478 [M+H]$^+$ Synthesis of UNC4253

Procedure for the synthesis of UNC2383 was followed to obtain a pale yellow solid.

$^1$H NMR (400 MHz, Chloroform-d) δ 12.20 (brs, 1H), 7.51 (d, J=0.8 Hz, 2H), 7.41-7.35 (m, 1H), 7.34-7.29 (m, 1H), 7.30-7.26 (m, 1H), 7.26-7.23 (m, 1H), 7.10 (d, J=2.6 Hz, 1H), 7.00 (dd, J=8.9, 2.6 Hz, 1H), 4.49-4.36 (m, 2H), 3.87 (s, 3H), 2.95 (t, J=7.4 Hz, 2H), 2.71 (t, J=5.2 Hz, 4H), 1.89-1.76 (m, 4H). LC-MS (λ=254 nm): 99%, $t_R$=4.5 min. MS (ESI+): 406 [M+H]$^+$ Synthesis of UNC4258

Procedure for the synthesis of UNC2383 was followed to obtain a pale yellow solid.

$^1$H NMR (400 MHz, Chloroform-d) δ 12.11 (brs, 1H), 7.63 (d, J=2.1 Hz, 1H), 7.56-7.46 (m, 1H), 7.46 (d, J=1.0 Hz, 1H), 7.42-7.33 (m, 1H), 7.35-7.27 (m, 2H), 7.32-7.23 (m, 2H), 4.40-4.22 (m, 2H), 3.04-3.09 (m, 1H), 2.31 (s, 3H), 2.28-2.03 (m, 4H), 1.93-1.76 (m, 2H), 1.78-1.58 (m, 2H). LC-MS (λ=254 nm): 99%, $t_R$=5.7 min. MS (ESI+): 424 [M+H]$^+$ Synthesis of UNC4267

Procedure for the synthesis of UNC2383 was followed to obtain a white solid.

$^1$H NMR (400 MHz, Chloroform-d) δ 12.16 (brs, 1H), 7.62 (dd, J=28.8, 8.1 Hz, 2H), 7.55 (s, 1H), 7.36 (td, J=7.3, 1.8 Hz, 2H), 7.34-7.22 (m, 4H), 4.40 (t, J=7.3 Hz, 2H), 2.94 (t, J=7.3 Hz, 2H), 2.71-2.67 (m, 4H), 1.88-1.71 (m, 4H).

6.5. Sequence Listing

INCORPORATION-BY-REFERENCE OF MATERIAL SUBMITTED ELECTRONICALLY

This application contains a sequence listing. It has been submitted electronically via EFS-Web as an ASCII text file entitled "150-29-UTIL_ST25.txt". The sequence listing is 6,369 bytes in size, and was created on May 10, 2019. It is hereby incorporated by reference in its entirety.

7. REFERENCES

1. Bennett, C. F. and Swayze, E. E. (2010) RNA targeting therapeutics: molecular mechanisms of antisense oligonucleotides as a therapeutic platform Annu. Rev. Pharmacol. Toxicol. 50, 259-293 DOI: 10.1146/annurev.pharmtox.010909.105654
2. Wu, S. Y., Lopez-Berestein, G., Calin, G. A., and Sood, A. K. (2014) RNAi Therapies: Drugging the Undruggable Sci. Transl. Med. 6, 240ps247 DOI: 10.1126/scitranslmed.3008362
3. Manoharan, M. (2004) RNA interference and chemically modified small interfering RNAs Curr. Opin. Chem. Biol. 8, 570-579 DOI: 10.1016/j.cbpa.2004.10.007
4. Watts, J. K. and Corey, D. R. (2012) Silencing disease genes in the laboratory and the clinic J. Pathol. 226, 365-379 DOI: 10.1002/path.2993
5. Tse, M. T. (2013) Regulatory watch: Antisense approval provides boost to field Nat. Rev. Drug Discovery 12, 179 DOI: 10.1038/nrd3963
6. Bennett, C. F., Baker, B. F., Pham, N., Swayze, E., and Geary, R. S. (2017) Pharmacology of Antisense Drugs Annu. Rev. Pharmacol. Toxicol. 57, 81-105 DOI: 10.1146/annurev-pharmtox-010716-104846
7. Juliano, R., Alam, M. R., Dixit, V., and Kang, H. (2008) Mechanisms and strategies for effective delivery of antisense and siRNA oligonucleotides Nucleic Acids Res. 36, 4158-4171 DOI: 10.1093/nar/gkn342
8. Juliano, R. L. (2016) The delivery of therapeutic oligonucleotides Nucleic Acids Res. 44, 6518-6548 DOI: 10.1093/nar/gkw236
9. Varkouhi, A. K., Scholte, M., Storm, G., and Haisma, H. J. (2011) Endosomal escape pathways for delivery of biologicals J. Controlled Release 151, 220-228 DOI: 10.1016/j.jconrel.2010.11.004
10. Juliano, R. L., Ming, X., and Nakagawa, O. (2012) Cellular uptake and intracellular trafficking of antisense and siRNA oligonucleotides Bioconjugate Chem. 23, 147-157 DOI: 10.1021/bc200377d
11. Xu, S., Olenyuk, B. Z., Okamoto, C. T., and Hamm-Alvarez, S. F. (2013) Targeting receptor-mediated endocytotic pathways with nanoparticles: rationale and advances Adv. Drug Delivery Rev. 65, 121-138 DOI: 10.1016/j.addr.2012.09.041
12. Doherty, G. J. and McMahon, H. T. (2009) Mechanisms of endocytosis Annu. Rev. Biochem. 78, 857-902 DOI: 10.1146/annurev.biochem.78.081307.110540
13. Mellman, I. and Emr, S. D. (2013) A Nobel Prize for membrane traffic: vesicles find their journey's end J. Cell Biol. 203, 559-561 DOI: 10.1083/jcb.201310134
14. Kummel, D. and Ungermann, C. (2014) Principles of membrane tethering and fusion in endosome and lysosome biogenesis Curr. Opin. Cell Biol. 29, 61-66 DOI: 10.1016/j.ceb.2014.04.007
15. Wang, T., Smith, E. A., Chapman, E. R., and Weisshaar, J. C. (2009) Lipid mixing and content release in single-vesicle, SNARE-driven fusion assay with 1-5 ms resolution Biophys. J. 96, 4122-4131 DOI: 10.1016/j.bpj.2009.02.050
16. Cai, H., Reinisch, K., and Ferro-Novick, S. (2007) Coats, tethers, Rabs, and SNAREs work together to mediate the intracellular destination of a transport vesicle Dev. Cell 12, 671-682 DOI: 10.1016/j.devcel.2007.04.005
17. Pfeffer, S. R. (2013) Rab GTPase regulation of membrane identity Curr. Opin. Cell Biol. 25, 414-419 DOI: 10.1016/j.ceb.2013.04.002
18. Ming, X., Carver, K., Fisher, M., Noel, R., Cintrat, J. C., Gillet, D., Barbier, J., Cao, C., Bauman, J., and Juliano, R. L. (2013) The small molecule Retro-1 enhances the pharmacological actions of antisense and splice switching oligonucleotides Nucleic Acids Res. 41, 3673-3687 DOI: 10.1093/nar/gkt066
19. von Kleist, L. and Haucke, V. (2012) At the crossroads of chemistry and cell biology: inhibiting membrane traffic by small molecules Traffic 13, 495-504 DOI: 10.1111/j.1600-0854.2011.01292.x
20. Yang, B., Ming, X., Cao, C., Laing, B., Yuan, A., Porter, M. A., Hull-Ryde, E. A., Maddry, J., Suto, M., Janzen, W. P., and Juliano, R. L. (2015) High-throughput screening identifies small molecules that enhance the pharmacological effects of oligonucleotides Nucleic Acids Res. 43, 1987-1996 DOI: 10.1093/nar/gkv060
21. Kang, H., Fisher, M. H., Xu, D., Miyamoto, Y. J., Marchand, A., Van Aerschot, A., Herdewijn, P., and Juliano, R. L. (2004) Inhibition of MDR1 gene expression by chimeric HNA antisense oligonucleotides Nucleic Acids Res. 32, 4411-4419 DOI: 10.1093/nar/gkh775
22. Dunn, K. W., Kamocka, M. M., and McDonald, J. H. (2011) A practical guide to evaluating colocalization in biological microscopy Am. J. Physiol. Cell Physiol. 300, C723-742 DOI: 10.1152/ajpcell.00462.2010
23. Keri, R. S., Hiremathad, A., Budagumpi, S., and Nagaraja, B. M. (2015) Comprehensive Review in Current Developments of Benzimidazole-Based Medicinal Chemistry Chem. Biol. Drug Des. 86, 19-65 DOI: 10.1111/cbdd.12462
24. Sazani, P., Gemignani, F., Kang, S. H., Maier, M. A., Manoharan, M., Persmark, M., Bortner, D., and Kole, R. (2002) Systemically delivered antisense oligomers upregulate gene expression in mouse tissues Nat. Biotechnol. 20, 1228-1233 DOI: 10.1038/nbt759
25. Kreda, S. M., Pickles, R. J., Lazarowski, E. R., and Boucher, R. C. (2000) G-protein-coupled receptors as targets for gene transfer vectors using natural small-molecule ligands Nat. Biotechnol. 18, 635-640 DOI: 10.1038/76479
26. Quon, B. S. and Rowe, S. M. (2016) New and emerging targeted therapies for cystic fibrosis BMJ. 352, i859 DOI: 10.1136/bmj.i859

27. Juliano, R. L., Ming, X., and Nakagawa, O. (2012) The chemistry and biology of oligonucleotide conjugates Acc. Chem. Res. 45, 1067-1076 DOI: 10.1021/ar2002123
28. Gilleron, J., Paramasivam, P., Zeigerer, A., Querbes, W., Marsico, G., Andree, C., Seifert, S., Amaya, P., Stoter, M., Koteliansky, V., Waldmann, H., Fitzgerald, K., Kalaidzidis, Y., Akinc, A., Maier, M. A., Manoharan, M., Bickle, M., and Zerial, M. (2015) Identification of siRNA delivery enhancers by a chemical library screen Nucleic Acids Res. 43, 7984-8001 DOI: 10.1093/nar/gkv762
29. Osborn, M. F., Alterman, J. F., Nikan, M., Cao, H., Didiot, M. C., Hassler, M. R., Coles, A. H., and Khvorova, A. (2015) Guanabenz (Wytensin) selectively enhances uptake and efficacy of hydrophobically modified siRNAs Nucleic Acids Res. 43, 8664-8672 DOI: 10.1093/nar/gkv942
30. Ming, X., Ju, W., Wu, H., Tidwell, R. R., Hall, J. E., and Thakker, D. R. (2009) Transport of dicationic drugs pentamidine and furamidine by human organic cation transporters Drug Metab. Dispos. 37, 424-430 DOI: 10.1124/dmd.108.024083
31. Kreda, S. M. and Gentzsch, M. (2011) Imaging CFTR protein localization in cultured cells and tissues Methods Mol. Biol. 742, 15-33 DOI: 10.1007/978-1-61779-120-8_2
32. Roberts, J., Palma, E., Sazani, P., Orum, H., Cho, M., and Kole, R. (2006) Efficient and persistent splice switching by systemically delivered LNA oligonucleotides in mice Mol. Ther. 14, 471-475 DOI: 10.1016/j.ymthe.2006.05.017

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world. It is to be understood that, while the disclosure has been described in conjunction with the detailed description, thereof, the foregoing description is intended to illustrate and not limit the scope. Other aspects, advantages, and modifications are within the scope of the claims set forth below. All publications, patents, and patent applications cited in this specification are herein incorporated by reference as if each individual publication or patent application were specifically and individually indicated to be incorporated by reference.

What is claimed is:

1. A compound having the Formula I:

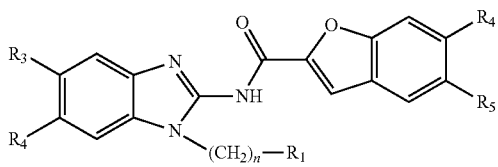

wherein:
$R_1$ is a pyrrolidine group;
$R_2$-$R_5$ are each independently $C_{1-8}$ alkyl, $C_{1-8}$ alkoxy, $C_{2-8}$ alkenyl, $C_{3-8}$ alkynyl, $C_{3-8}$ cycloalkyl, H or halogen;
n is an integer between 1 and 8;
or a pharmaceutically acceptable salt thereof.

2. The compound of claim 1, wherein n is 2-4 and $R_1$ is a pyrrolidine group.

3. The compound of claim 1, wherein n is 2-4 and $R_2$-$R_5$ are each independently $C_{1-4}$ alkyl, $C_{1-4}$ alkoxy, H or halogen.

4. The compound of claim 3, wherein the halogen is bromine or chorine.

5. A composition comprising the compound of claim 1, wherein the composition further comprises a compound having the Formula II:

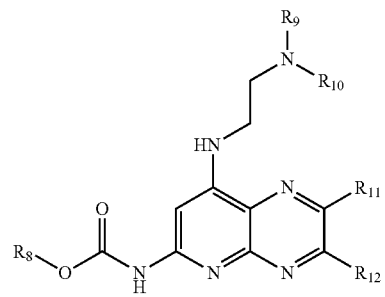

wherein:
$R_8$ is $C_{1-8}$ alkyl or a linking group;
$R_9$ is $C_{1-8}$ alkyl or a linking group;
$R_{10}$ is $C_{1-8}$ alkyl;
$R_{11}$ and $R_{12}$ are each independently aryl, $C_{1-8}$ alkyl, $C_{1-8}$ alkoxy, amino, H, halogen, or heteroaryl;
or a pharmaceutically acceptable salt thereof.

6. The composition of claim 5, wherein the compound of Formula II has the structure:

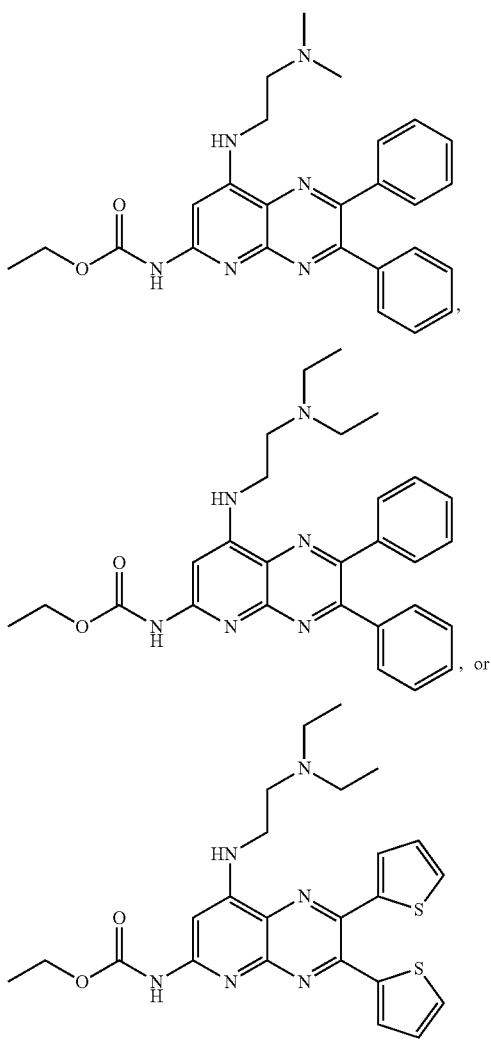

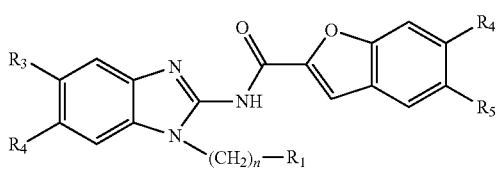

or a pharmaceutically acceptable salt thereof.

7. A composition comprising an oligonucleotide and a compound having the Formula I:

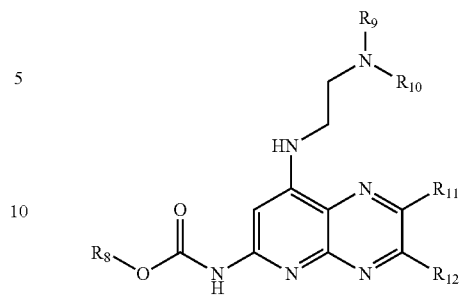

wherein:

R₁ is a pyrrolidine group;

R₂-R₅ are each independently C$_{1-8}$ alkyl, C$_{1-8}$ alkoxy, C$_{2-8}$ alkenyl, C$_{3-8}$ alkynyl, C$_{3-8}$ cycloalkyl, H or halogen;

n is an integer between 1 and 8; and a pharmaceutically acceptable carrier.

8. The composition of claim 7, wherein the composition further comprises a compound having the Formula II:

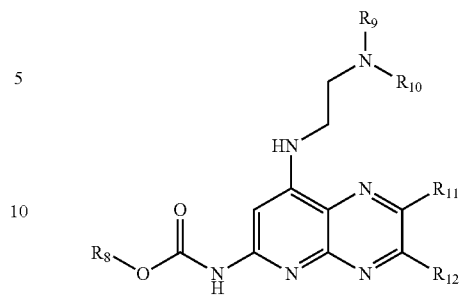

wherein:

R₈ is C$_{1-8}$ alkyl or a linking group;

R₉ is C$_{1-8}$ alkyl or a linking group;

R₁₀ is C$_{1-8}$ alkyl;

R₁₁ and R₁₂ are each independently aryl, C$_{1-8}$ alkyl, C$_{1-8}$ alkoxy, amino, H, halogen, or heteroaryl;

or a pharmaceutically acceptable salt thereof.

9. The composition of claim 8, wherein the compound of Formula II has the structure:

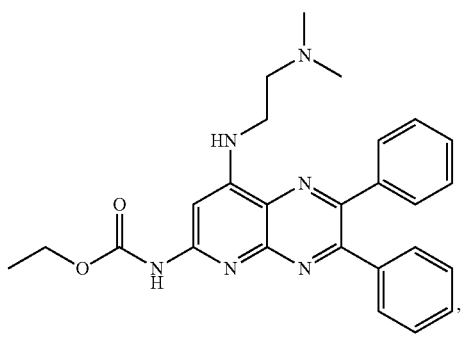

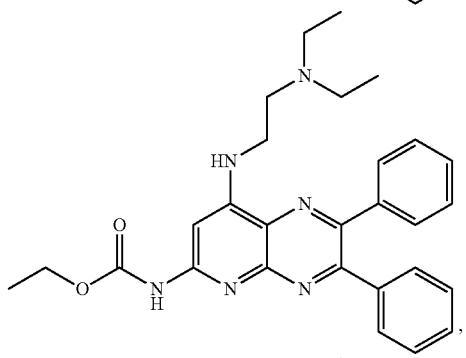

, or

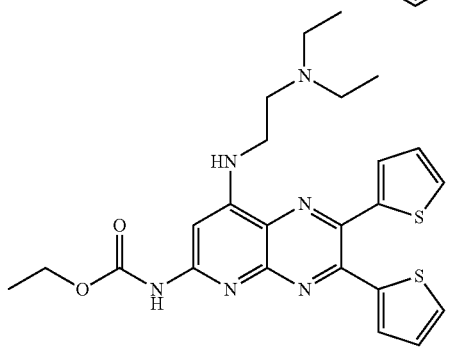

or a pharmaceutically acceptable salt thereof.

10. The composition of claim 1, wherein the oligonucleotide is a phosphorodiamidate morpholino oligomer (PMO).

11. A method of administering an oligonucleotide of interest to a cell which comprises administering to the cell the oligonucleotide and a compound of Formula I:

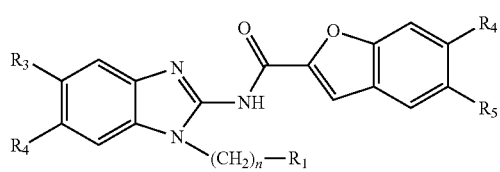

wherein:
$R_1$ is a pyrrolidine group;
$R_2$-$R_5$ are each independently $C_{1-8}$ alkyl, $C_{1-8}$ alkoxy, $C_{2-8}$ alkenyl, $C_{3-8}$ alkynyl, $C_{3-8}$ cycloalkyl, H or halogen;
n is an integer between 1 and 8;
or a pharmaceutically acceptable salt thereof.

12. The method of claim 11, further comprising administering to the cell a compound having the Formula II:

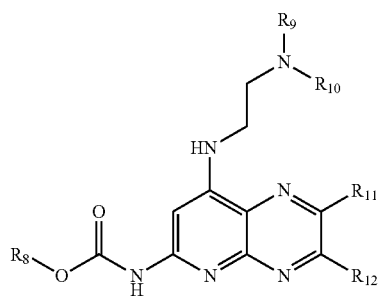

wherein:
$R_8$ is $C_{1-8}$ alkyl or a linking group;
$R_9$ is $C_{1-8}$ alkyl or a linking group;
$R_{10}$ is $C_{1-8}$ alkyl;
$R_{11}$ and Ria are each independently aryl, $C_{1-8}$ alkyl, $C_{1-8}$ alkoxy, amino, H, halogen, or heteroaryl;
or a pharmaceutically acceptable salt thereof.

13. The method of claim 11, wherein the oligonucleotide is a phosphorodiamidate morpholino oligomer (PMO).

14. The method of claim 11, wherein the method is carried out by administering the oligonucleotide to the cell, and concurrently administering the compound having formula I to the cell.

15. The method of claim 11, wherein the compound having formula I is administered after the oligonucleotide is administered to the cell.

16. The method of claim 11, wherein the oligonucleotide is an antisense oligonucleotide.

17. The method of claim 11, wherein the oligonucleotide is a splice switching oligonucleotide.

18. The method of claim 11, wherein the oligonucleotide is an siRNA.

19. The method of claim 11, wherein the cell is a lung cell or an airway cell.

20. The method of claim 19, wherein the lung cell is a human bronchial epithelial cell (HBEC), a human nasal epithelial cell (HNEC), a mouse tracheal epithelial cell (MTEC), a human alveolar type I or type II cell, a human lung submucosal gland cell, a human lung leucocyte, or a human lung inflammatory cell.

21. The compound of claim 1, wherein the compound of Formula I has the structure:

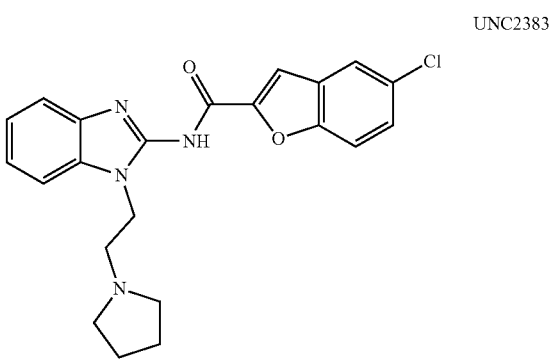

UNC2383

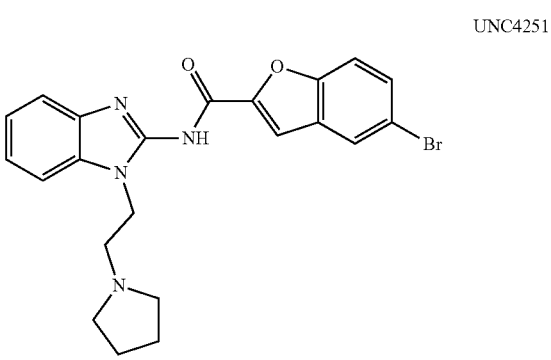

UNC4251

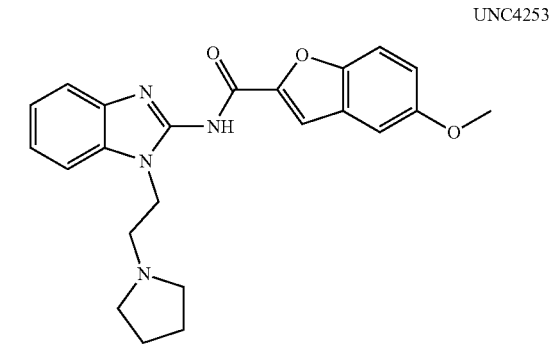

UNC4253

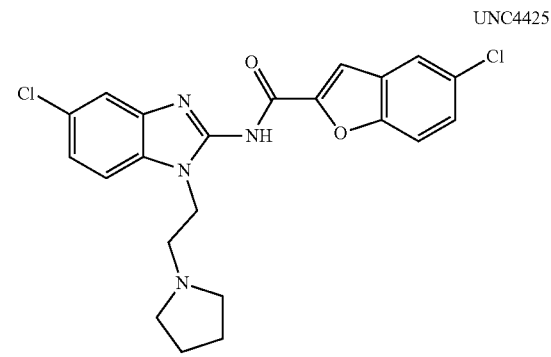

UNC4425

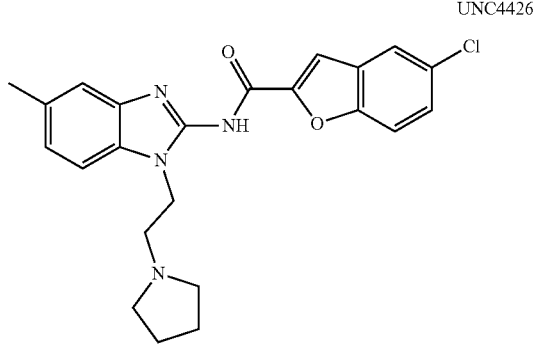
UNC4426
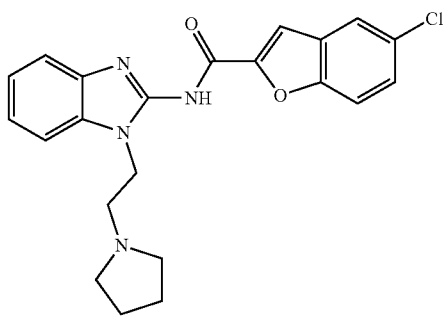
UNC2383
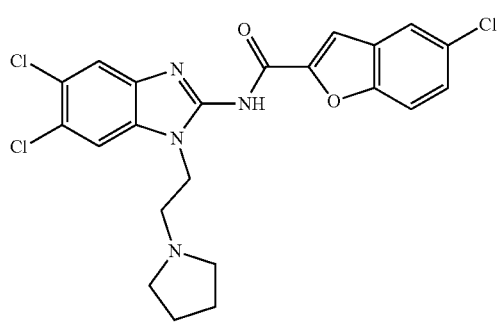
UNC4428
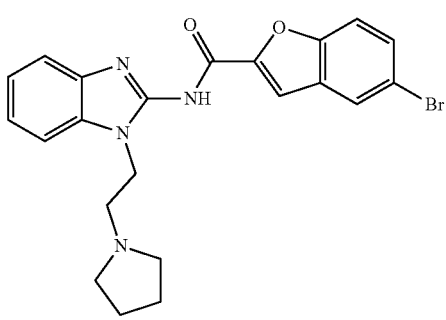
UNC4251
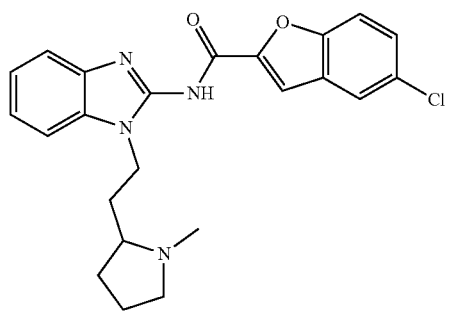
UNC4258
or
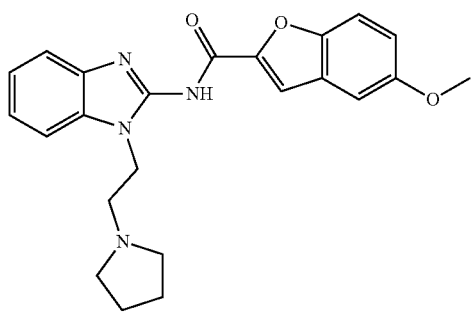
UNC4253
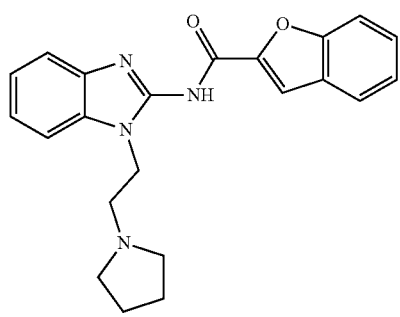
UNC4267
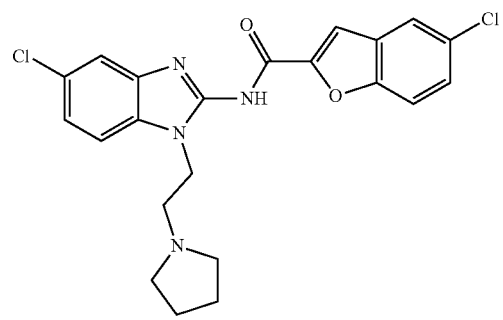
UNC4425
22. The composition of claim 7, wherein the compound of Formula I has the structure:

-continued
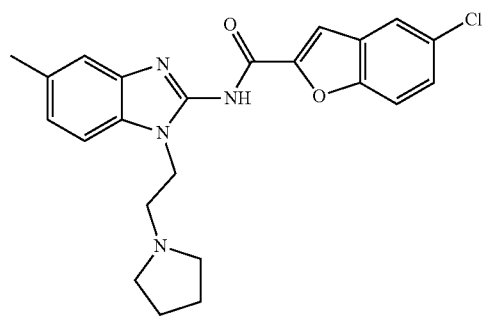
UNC4426
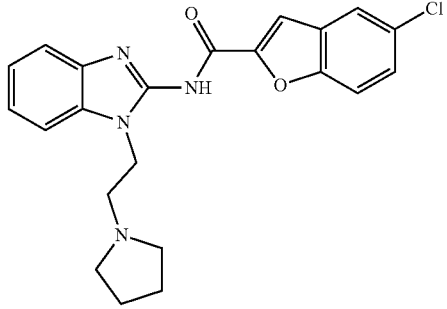
UNC2383
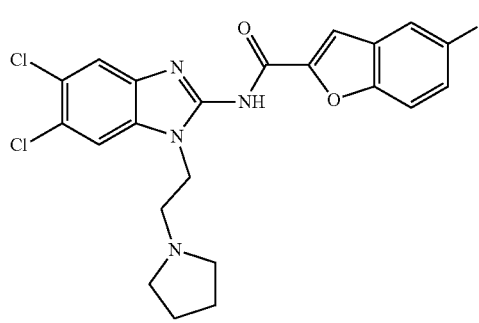
UNC4428
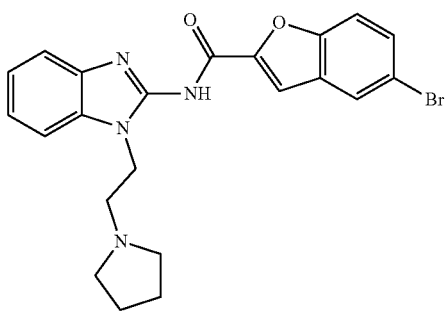
UNC4251
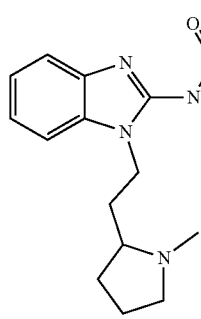
UNC4258
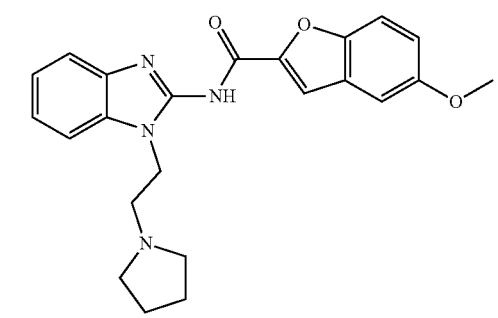
UNC4253
or
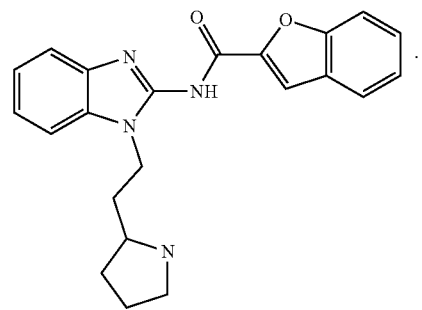
UNC4267
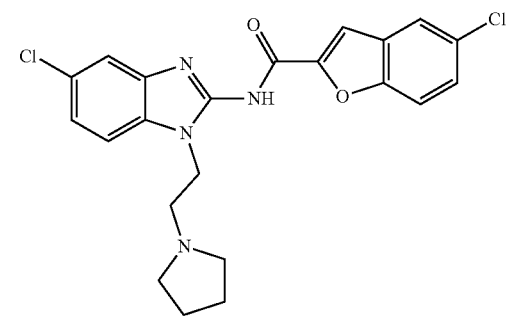
UNC4425
23. The method of claim 11, wherein the compound of Formula I has the structure:

-continued
UNC4426
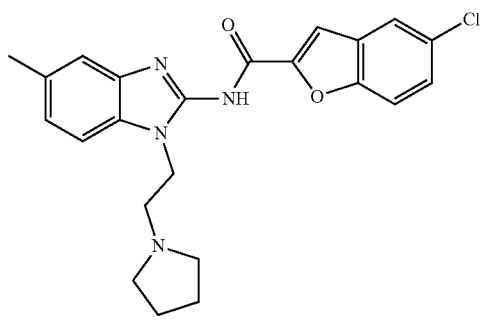
UNC4258
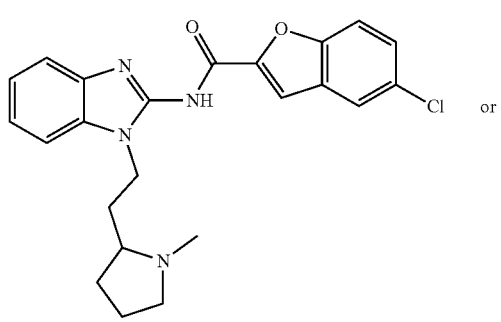
or
UNC4428
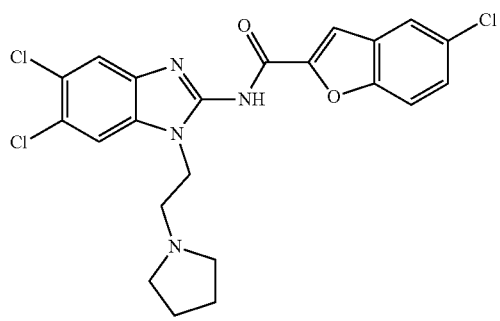
UNC4267
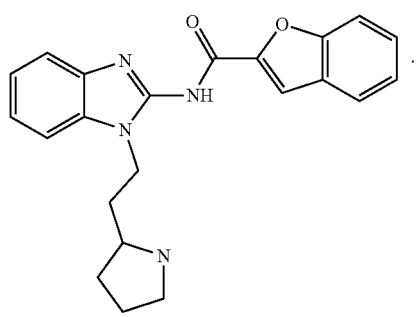
* * * * *

SEQUENCE LISTING

```
<160> NUMBER OF SEQ ID NOS: 7

<210> SEQ ID NO 1
<211> LENGTH: 19
<212> TYPE: DNA
<213> ORGANISM: artificial
<220> FEATURE:
<223> OTHER INFORMATION: synthetic sequence
<220> FEATURE:
<221> NAME/KEY: modified_base
<222> LOCATION: (1)..(1)
<223> OTHER INFORMATION: Locked nucleic acid (LNA)
<220> FEATURE:
<221> NAME/KEY: modified_base
<222> LOCATION: (2)..(2)
<223> OTHER INFORMATION: gm; Phosphorothiolate (PS)
<220> FEATURE:
<221> NAME/KEY: modified_base
<222> LOCATION: (3)..(3)
<223> OTHER INFORMATION: um; Phosphorothiolate (PS); Locked nucleic
       acid (LNA)
<220> FEATURE:
<221> NAME/KEY: modified_base
<222> LOCATION: (4)..(4)
<223> OTHER INFORMATION: Phosphorothiolate (PS)
<220> FEATURE:
<221> NAME/KEY: modified_base
<222> LOCATION: (5)..(5)
<223> OTHER INFORMATION: um; Phosphorothiolate (PS)
<220> FEATURE:
<221> NAME/KEY: modified_base
<222> LOCATION: (6)..(6)
<223> OTHER INFORMATION: um; Phosphorothiolate (PS)
<220> FEATURE:
```

```
<221> NAME/KEY: modified_base
<222> LOCATION: (7)..(7)
<223> OTHER INFORMATION: m2a; Locked nucleic acid (LNA);
      Phosphorothiolate (PS)
<220> FEATURE:
<221> NAME/KEY: modified_base
<222> LOCATION: (8)..(8)
<223> OTHER INFORMATION: Phosphorothiolate (PS)
<220> FEATURE:
<221> NAME/KEY: modified_base
<222> LOCATION: (9)..(9)
<223> OTHER INFORMATION: um; Locked nucleic acid (LNA);
      Phosphorothiolate (PS)
<220> FEATURE:
<221> NAME/KEY: modified_base
<222> LOCATION: (10)..(10)
<223> OTHER INFORMATION: Phosphorothiolate (PS)
<220> FEATURE:
<221> NAME/KEY: modified_base
<222> LOCATION: (11)..(11)
<223> OTHER INFORMATION: m2a; Phosphorothiolate (PS)
<220> FEATURE:
<221> NAME/KEY: modified_base
<222> LOCATION: (12)..(12)
<223> OTHER INFORMATION: cm; Phosphorothiolate (PS)
<220> FEATURE:
<221> NAME/KEY: modified_base
<222> LOCATION: (13)..(13)
<223> OTHER INFORMATION: Phosphorothiolate (PS)
<220> FEATURE:
<221> NAME/KEY: modified_base
<222> LOCATION: (14)..(14)
<223> OTHER INFORMATION: m2a; Phosphorothiolate (PS)
<220> FEATURE:
<221> NAME/KEY: modified_base
<222> LOCATION: (15)..(15)
<223> OTHER INFORMATION: um; Phosphorothiolate (PS)
<220> FEATURE:
<221> NAME/KEY: modified_base
<222> LOCATION: (16)..(16)
<223> OTHER INFORMATION: um; Phosphorothiolate (PS)
<220> FEATURE:
<221> NAME/KEY: modified_base
<222> LOCATION: (17)..(17)
<223> OTHER INFORMATION: um; Phosphorothiolate (PS)
<220> FEATURE:
<221> NAME/KEY: modified_base
<222> LOCATION: (18)..(18)
<223> OTHER INFORMATION: um; Phosphorothiolate (PS); Locked Nucleic
      Acid (LNA)

<400> SEQUENCE: 1
agucuuacuc accauuuua                                             19

<210> SEQ ID NO 2
<211> LENGTH: 18
<212> TYPE: DNA
<213> ORGANISM: artificial
<220> FEATURE:
<223> OTHER INFORMATION: synthetic sequence
<220> FEATURE:
<221> NAME/KEY: modified_base
<222> LOCATION: (1)..(1)
<223> OTHER INFORMATION: Phosphorothiolate (PS); Locked Nucleic Acid
      (LNA)
<220> FEATURE:
<221> NAME/KEY: modified_base
<222> LOCATION: (2)..(2)
<223> OTHER INFORMATION: um; Phosphorothiolate (PS)
<220> FEATURE:
<221> NAME/KEY: modified_base
<222> LOCATION: (3)..(3)
<223> OTHER INFORMATION: um; Phosphorothiolate (PS)
<220> FEATURE:
<221> NAME/KEY: modified_base
<222> LOCATION: (4)..(4)
<223> OTHER INFORMATION: m2a; Phosphorothiolate (PS)
```

```
<220> FEATURE:
<221> NAME/KEY: modified_base
<222> LOCATION: (5)..(5)
<223> OTHER INFORMATION: cm; Phosphorothiolate (PS); Locked Nucleic Acid
      (LNA)
<220> FEATURE:
<221> NAME/KEY: modified_base
<222> LOCATION: (6)..(6)
<223> OTHER INFORMATION: Phosphorothiolate (PS)
<220> FEATURE:
<221> NAME/KEY: modified_base
<222> LOCATION: (7)..(7)
<223> OTHER INFORMATION: cm; Phosphorothiolate (PS)
<220> FEATURE:
<221> NAME/KEY: modified_base
<222> LOCATION: (8)..(8)
<223> OTHER INFORMATION: a2m; Phosphorothiolate (PS)
<220> FEATURE:
<221> NAME/KEY: modified_base
<222> LOCATION: (9)..(9)
<223> OTHER INFORMATION: cm; Phosphorothiolate (PS)
<220> FEATURE:
<221> NAME/KEY: modified_base
<222> LOCATION: (10)..(10)
<223> OTHER INFORMATION: cm; Phosphorothiolate (PS)
<220> FEATURE:
<221> NAME/KEY: modified_base
<222> LOCATION: (11)..(11)
<223> OTHER INFORMATION: Phosphorothiolate (PS)
<220> FEATURE:
<221> NAME/KEY: modified_base
<222> LOCATION: (12)..(12)
<223> OTHER INFORMATION: um; Phosphorothiolate (PS)
<220> FEATURE:
<221> NAME/KEY: modified_base
<222> LOCATION: (13)..(13)
<223> OTHER INFORMATION: um; Phosphorothiolate (PS)
<220> FEATURE:
<221> NAME/KEY: modified_base
<222> LOCATION: (14)..(14)
<223> OTHER INFORMATION: um; Phosphorothiolate (PS)
<220> FEATURE:
<221> NAME/KEY: modified_base
<222> LOCATION: (15)..(15)
<223> OTHER INFORMATION: Phosphorothiolate (PS)
<220> FEATURE:
<221> NAME/KEY: modified_base
<222> LOCATION: (16)..(16)
<223> OTHER INFORMATION: m2a; Phosphorothiolate (PS)
<220> FEATURE:
<221> NAME/KEY: modified_base
<222> LOCATION: (17)..(17)
<223> OTHER INFORMATION: m2a; Phosphorothiolate (PS)
<220> FEATURE:
<221> NAME/KEY: modified_base
<222> LOCATION: (18)..(18)
<223> OTHER INFORMATION: um

<400> SEQUENCE: 2
cuuacucacc auuuuaau                                                   18

<210> SEQ ID NO 3
<211> LENGTH: 18
<212> TYPE: DNA
<213> ORGANISM: aritificial
<220> FEATURE:
<221> NAME/KEY: modified_base
<222> LOCATION: (1)..(1)
<223> OTHER INFORMATION: Locked nucleic acid (LNA); Phosphorothiolate
      (PS)
<220> FEATURE:
<221> NAME/KEY: modified_base
<222> LOCATION: (2)..(2)
<223> OTHER INFORMATION: m2a; Phosphorothiolate (PS)
<220> FEATURE:
<221> NAME/KEY: modified_base
<222> LOCATION: (3)..(3)
```

```
<223> OTHER INFORMATION: m2g; Phosphorothiolate (PS)
<220> FEATURE:
<221> NAME/KEY: modified_base
<222> LOCATION: (4)..(4)
<223> OTHER INFORMATION: um; Locked nucleic acid (LNA);
      Phosphorothiolate (PS)
<220> FEATURE:
<221> NAME/KEY: modified_base
<222> LOCATION: (5)..(5)
<223> OTHER INFORMATION: Phosphorothiolate (PS)
<220> FEATURE:
<221> NAME/KEY: modified_base
<222> LOCATION: (6)..(6)
<223> OTHER INFORMATION: um; Phosphorothiolate (PS)
<220> FEATURE:
<221> NAME/KEY: modified_base
<222> LOCATION: (7)..(7)
<223> OTHER INFORMATION: um; Phosphorothiolate (PS)
<220> FEATURE:
<221> NAME/KEY: modified_base
<222> LOCATION: (8)..(8)
<223> OTHER INFORMATION: m2a; Phosphorothiolate (PS)
<220> FEATURE:
<221> NAME/KEY: modified_base
<222> LOCATION: (9)..(9)
<223> OTHER INFORMATION: Phosphorothiolate (PS)
<220> FEATURE:
<221> NAME/KEY: modified_base
<222> LOCATION: (10)..(10)
<223> OTHER INFORMATION: um; Phosphorothiolate (PS)
<220> FEATURE:
<221> NAME/KEY: modified_base
<222> LOCATION: (11)..(11)
<223> OTHER INFORMATION: cm; Phosphorothiolate (PS)
<220> FEATURE:
<221> NAME/KEY: modified_base
<222> LOCATION: (12)..(12)
<223> OTHER INFORMATION: m2a; Phosphorothiolate (PS)
<220> FEATURE:
<221> NAME/KEY: modified_base
<222> LOCATION: (13)..(13)
<223> OTHER INFORMATION: cm; Phosphorothiolate (PS)
<220> FEATURE:
<221> NAME/KEY: modified_base
<222> LOCATION: (14)..(14)
<223> OTHER INFORMATION: cm; Locked nucleic acid (LNA);
      Phosphorothiolate (PS)
<220> FEATURE:
<221> NAME/KEY: modified_base
<222> LOCATION: (15)..(15)
<223> OTHER INFORMATION: Phosphorothiolate (PS)
<220> FEATURE:
<221> NAME/KEY: modified_base
<222> LOCATION: (16)..(18)
<223> OTHER INFORMATION: um; Phosphorothiolate (PS)

<400> SEQUENCE: 3
gagucuuacu cauuauuu                                                  18

<210> SEQ ID NO 4
<211> LENGTH: 20
<212> TYPE: DNA
<213> ORGANISM: artificial
<220> FEATURE:
<223> OTHER INFORMATION: synthetic sequence
<220> FEATURE:
<221> NAME/KEY: modified_base
<222> LOCATION: (1)..(20)
<223> OTHER INFORMATION: 2-Me; Phosphorothiolate (PS)

<400> SEQUENCE: 4
gttattcttt agaatggtgc                                                20

<210> SEQ ID NO 5
<211> LENGTH: 20
```

```
<212> TYPE: DNA
<213> ORGANISM: artificial
<220> FEATURE:
<223> OTHER INFORMATION: synthetic sequence
<220> FEATURE:
<221> NAME/KEY: modified_base
<222> LOCATION: (1)..(5)
<223> OTHER INFORMATION: 2-O-Me; Phosphorothiolate (PS)
<220> FEATURE:
<221> NAME/KEY: modified_base
<222> LOCATION: (6)..(15)
<223> OTHER INFORMATION: Phosphorothiolate (PS)
<220> FEATURE:
<221> NAME/KEY: modified_base
<222> LOCATION: (16)..(20)
<223> OTHER INFORMATION: 2-O-Me; Phosphorothiolate (PS)

<400> SEQUENCE: 5
ccatcccgac ctcgcgctcc                                          20

<210> SEQ ID NO 6
<211> LENGTH: 23
<212> TYPE: DNA
<213> ORGANISM: artificial
<220> FEATURE:
<223> OTHER INFORMATION: synthetic sequence

<400> SEQUENCE: 6
cgtaaacggc cacaagttca gcg                                      23

<210> SEQ ID NO 7
<211> LENGTH: 24
<212> TYPE: DNA
<213> ORGANISM: artificial
<220> FEATURE:
<223> OTHER INFORMATION: synthetic sequence

<400> SEQUENCE: 7
gtggtgcaga tgaacttcag ggtc                                     24
```